US009000028B2

(12) United States Patent
Kim et al.

(10) Patent No.: US 9,000,028 B2
(45) Date of Patent: Apr. 7, 2015

(54) INDOLE AND INDAZOLE COMPOUNDS AS AN INHIBITOR OF CELLULAR NECROSIS

(71) Applicant: LG Life Sciences Ltd., Seoul (KR)

(72) Inventors: Soon Ha Kim, Daejeon (KR); Hyoung Jin Kim, Daejeon (KR); Sun Young Koo, Daejeon (KR); Chul Woong Chung, Daejeon (KR); Sung Bae Lee, Daejeon (KR); Heui Sul Park, Daejeon (KR); Seung Hyun Yoon, Daejeon (KR); Hyo Shin Kwak, Daejeon (KR); Dong Ook Seo, Daejeong (KR); Eok Park, Daejeong (KR)

(73) Assignee: LG Life Sciences Ltd., Seoul (KR)

( * ) Notice: Subject to any disclaimer, the term of this patent is extended or adjusted under 35 U.S.C. 154(b) by 0 days.

(21) Appl. No.: 13/859,581

(22) Filed: Apr. 9, 2013

(65) Prior Publication Data

US 2013/0237532 A1    Sep. 12, 2013

Related U.S. Application Data

(62) Division of application No. 12/671,038, filed on Mar. 4, 2010, now Pat. No. 8,436,038.

(30) Foreign Application Priority Data

Aug. 17, 2007  (KR) .................. 10-2007-00882687

(51) Int. Cl.
| | | |
|---|---|---|
| A01N 43/38 | (2006.01) | |
| A61K 31/505 | (2006.01) | |
| C07D 417/06 | (2006.01) | |
| C07D 413/04 | (2006.01) | |
| C07D 413/14 | (2006.01) | |
| C07D 417/04 | (2006.01) | |
| C07D 417/14 | (2006.01) | |
| C07D 487/04 | (2006.01) | |
| C07F 9/6558 | (2006.01) | |
| A61K 31/404 | (2006.01) | |
| A61K 31/416 | (2006.01) | |
| A61K 31/427 | (2006.01) | |
| A61K 31/4439 | (2006.01) | |
| A61K 31/454 | (2006.01) | |
| A61K 31/4545 | (2006.01) | |
| A61K 31/496 | (2006.01) | |
| A61K 31/497 | (2006.01) | |
| A61K 31/5377 | (2006.01) | |
| A61K 31/541 | (2006.01) | |
| A61K 45/06 | (2006.01) | |
| A61K 31/445 | (2006.01) | |
| A61K 31/675 | (2006.01) | |

(52) U.S. Cl.
CPC ............ *C07D 417/06* (2013.01); *C07D 413/04* (2013.01); *C07D 413/14* (2013.01); *C07D 417/04* (2013.01); *C07D 417/14* (2013.01); *C07D 487/04* (2013.01); *C07F 9/65586* (2013.01); *A61K 31/404* (2013.01); *A61K 31/416* (2013.01); *A61K 31/427* (2013.01); *A61K 31/4439* (2013.01); *A61K 31/454* (2013.01); *A61K 31/4545* (2013.01); *A61K 31/496* (2013.01); *A61K 31/497* (2013.01); *A61K 31/5377* (2013.01); *A61K 31/541* (2013.01); *A61K 45/06* (2013.01); *A61K 31/445* (2013.01); *A61K 31/675* (2013.01); *C07F 9/65583* (2013.01)

(58) Field of Classification Search
USPC .................................. 548/490; 514/515, 415
See application file for complete search history.

(56) References Cited

U.S. PATENT DOCUMENTS

| | | | |
|---|---|---|---|
| 3,847,934 A | 11/1974 | Bern | |
| 4,086,353 A | 4/1978 | Neumann | |
| 5,721,246 A | 2/1998 | Yoshino et al. | |
| 8,222,414 B2 | 7/2012 | Kim et al. | |
| 2004/0102437 A1 | 5/2004 | Takami et al. | |
| 2010/0210647 A1 | 8/2010 | Kim et al. | |
| 2010/0267708 A1 | 10/2010 | Kim et al. | |
| 2010/0291533 A1 | 11/2010 | Kim et al. | |
| 2012/0088760 A1 | 4/2012 | Kim et al. | |

FOREIGN PATENT DOCUMENTS

| | | | |
|---|---|---|---|
| EP | 1 380 576 A1 | 1/2004 | |
| EP | 1 873 144 A1 | 1/2006 | |
| EP | 1 632 491 A1 | 3/2006 | |
| WO | WO 98/22457 A1 | 5/1998 | |
| WO | WO 02/18335 A1 | 3/2002 | |
| WO | WO 2004/009557 A1 | 1/2004 | |
| WO | WO 2005/035506 A1 | 4/2005 | |

(Continued)

OTHER PUBLICATIONS

L. Montebugnoli et al., 104 Oral and maxillofacial surgery, 473-477 (2007).*
A. Lipton, 38 Annual Review of Pharmacology and Toxicology, 159-177 (1998).*
H. Girouard et al., 100 Journal of Applied Physiology, 328-335, 332 (2006).*
R. S. Shah et al., 52 Biomedicine & Pharmacotherapy, 199-207 (2008).*
J.T. O'Brien et al., 2 The Lancet Neurology, 89-98, 96 (2003).*

(Continued)

*Primary Examiner* — Alexander R Pagano
(74) *Attorney, Agent, or Firm* — Birch, Stewart, Kolasch & Birch, LLP

(57) ABSTRACT

The present invention relates to indole or indazole compounds, pharmaceutically acceptable salts or isomers thereof which are useful for the prevention or treatment of cellular necrosis and necrosis-associated diseases. The present invention also relates to a method and a composition for the prevention or treatment of cellular necrosis and necrosis-associated diseases, comprising said indole or indazole compounds as an active ingredient.

3 Claims, No Drawings

(56) References Cited

FOREIGN PATENT DOCUMENTS

| WO | WO 2006/058338 A2 | 6/2006 |
| WO | WO 2006/112549 A1 | 10/2006 |

OTHER PUBLICATIONS

V.J. Desmet et al., 19 Hepatology, 1513-1520 (1994).*
S. Terai et al., 24 Stem Cells, 2292-2298 (2006).*
I. Collins, Current Signal Transduction Therapy, 1, 13-23, 13 (2006).*
F.F. Piccioitto et al., 46 Journal of Hepatology, 459-465 (2007).*
M. Buti et al., 47 Journal of Hepatology, 366-371 (2007).*
K. Weigand et al., 13 World Journal of Gastroenterology, 1897-1905 (2007).*
C-L Lai et al., 357 The New England Journal of Medicine, 2576-2588 (2007).*
J. Lehmann et al., 50 European Urology, 141-147, 143 (2006).*
Y. Nakayama et al., 161 Cancer Letters, 63-71 (2000).*
S. Ellenberg et al., 8 Statistics in Medicine, 405-413 (1989).*
D. Schuppan et al., 371 The Lancet, 838-851 (2008).*
R. Bataller et al., 115 The Journal of Clinical Investigation, 209-218 (2005).*
S. Erickson, 50 Journal of Lipid Research, s412-s416 (2009).*
J.R. Lewis et al., 55 Digestive Diseases and Sciences, 560-578 (2010).*
J.H. Poupaert, Drug Design: Basic Principles and Applications, in 2 Encyclopedia of Pharmaceutical Technology 1362-1369, 1367 (James Swarbrick ed., 3rd ed., 2007).*
L.I. Zon et al., Nature Reviews Drug Discovery 4, 35 (2005).*
B.A. Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).
Dai, W. et al, "Chemistry of aminophenols. Part 2: A general and efficient synthesis of indoles possessing a nitrogen substituent at the C4, C5, C6 and C7 positions," Tetrahedron Letters, 2002, vol. 43, pp. 7699-7702.
Huang et al., "4-Bromo-N-(2-phenyl-1H-indol-7-yl)-benzenesulfonamide", Acta Cryst., vol. E60, 2004 (Published online Mar. 6, 2004), pp. o488-o489.
Huang et al., "Crystal structures of p-methyl-N-(2-phenyl-1H-indol-7-yl)-benzene-sulfonamide, $C_{21}H_{18}N_2O_2S$, and p-methoxy-N-(2-phenyl-1H-indol-7-yl)-benzene-sulfonamide, $C_{21}H_{18}N_2O_3S$", Z. Kristallogr. NCS, vol. 220, 2005, pp. 258-260.

* cited by examiner

INDOLE AND INDAZOLE COMPOUNDS AS AN INHIBITOR OF CELLULAR NECROSIS

CROSS REFERENCE TO RELATED APPLICATIONS

This is a divisional application of U.S. application Ser. No. 12/671,038 filed on Jan. 28, 2010, which is the national phase of PCT International Application No. PCT/KR2008/004784 filed on Aug. 18, 2008, which claims the benefit of priority of KR 10-2007-0082687, filed on Aug. 17, 2007. The entire contents of each of the above-identified applications are hereby incorporated by reference.

TECHNICAL FIELD

The present invention relates to indole or indazole compounds of formula (1), pharmaceutically acceptable salts or isomers thereof, and method and composition for the prevention or treatment of cellular necrosis and necrosis-associated diseases comprising the same as an active ingredient.

BACKGROUND ART

Most researches associated with cell death have been concentrated on apoptosis of cells, also known as programmed cell death (PCD). With the discovery of the enzyme caspase, a number of pharmaceutical companies have promoted the development of drugs utilizing caspase inhibitors during the past 10 years. However, the current status is that there have hardly been any of these drugs approved by FDA. This is because the apoptosis of cells is a cell death which occurs under physiological circumstances and such a cell death may be probably due to the defense mechanism for maintaining homeostasis in the body. In contrast, necrosis is a cell death which mainly occurs under morbid circumstances, and in most cases it is characterized by accompanying the inflammatory response. Necrosis has been known as an uncontrolled cell death for a long time, but a recent research (Proskurykakov S Y et al. 2002, Biochemistry) reported the necrosis as an active/controlled cell death. Typical diseases caused by necrosis include ischemic (e.g. myocardial infarction, stroke, renal infarction), neurodegenerative, and inflammatory diseases. Since it is believed that Necrosis is an uncontrolled, accidental cell death under morbid circumstances, researches on the functional mechanism, molecular targets, signal transduction systems, etc. thereof have rarely been conducted. Thus, there arises a compelling need to discover and develop the necrosis-inhibiting substances for the treatment of ischemic, neurodegenerative, and inflammatory diseases which are caused by necrosis, and to elucidate the biological, pathological causes of necrosis.

The indole derivatives according to the present invention have very useful structures from a medical viewpoint and many publications have reported the research results with reference to these structures. Among the research results, the following are the most representative of all: the patent WO2006/112549 reported some indole derivatives having the activity for the glucokinase, the patent WO95/07276 reported those useful as anti-tumor agents and as inhibitors against the production of cardiovascular system, and the patent WO2004/018428 reported those useful as antibiotics.

DETAILED DESCRIPTION OF THE INVENTION

Technical Subject to be Solved

Thus, the present inventors have extensively studied under the above mentioned technical background to develop new compounds that exhibit an effect of prevention or treatment and amelioration for cellular necrosis and necrosis-associated diseases, particularly useful for the prevention or treatment of hepatic diseases. As a result thereof, they confirmed that the indole or indazole derivatives of formula (1) as explained below show a superior effect for the prevention and treatment of cellular necrosis and necrosis-associated diseases, whereby completed the present invention.

Therefore, it is an object of the present invention to provide new indole or indazole derivatives of formula (1).

It is another object of the present invention to provide a composition for the prevention or treatment of cellular necrosis and necrosis-associated diseases, in particular, for hepatoprotection, hepatic functional improvement, and prevention or treatment of acute/chronic hepatic diseases, which comprises as an active ingredient the compounds of formula (1), pharmaceutically acceptable salts or isomers thereof together with a pharmaceutically acceptable carrier or diluent, and process for preparing the same.

It is still another object of the present invention to provide a method for the prevention or treatment of cellular necrosis and associated diseases, in particular, for hepatoprotection, hepatic functional improvement, and prevention or treatment of acute/chronic hepatic diseases using said composition.

Means for Solving the Technical Subject

To accomplish the above objects, the present invention provides indole or indazole compounds of the following formula (1):

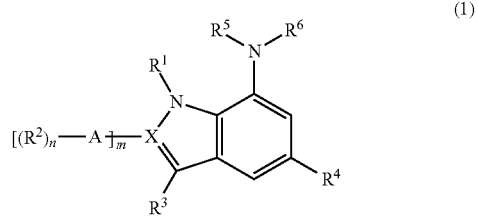

(1)

in which
n denotes a number of 1 to 3,
m denotes 0 or 1,
A represents a direct bond, represents phenyl, or represents 6 membered heteroaryl having 1 to 2 nitrogen atoms,
X represents C or N, with the proviso that m is 0 when X is N, and m is 1 when X is C,
$R^1$ represent hydrogen, alkyl, —$(CH_2)_r NR^7 R^8$, or —$(CH_2)_r CO_2 H$, wherein r denotes a number of 1 to 5, and $R^7$ and $R^8$ independently of one another represent hydrogen, alkyl or alkylcarbonyl, or may together form an optionally alkyl-substituted alkylene chain wherein optionally one methylene is replaced by N atom,
$R^2$ represents hydrogen, halogen, cyano, nitro, hydroxy, alkyl, alkoxy or trialkylsilyl, represents —$(CH_2)_p CO_2 R^7$, —$(CH_2)_p OR^7$, —$(CH_2)_p NR^7 R^8$, —$NHR^{10}$, —$N(H)S(O)_2 R^7$, —$NHC(O)R^{10}$, —$(CH_2)_p S(O)_2 R^7$ or —$(CH_2)_p$-heterocycle-$R^{10}$, wherein p denotes a number of 0 to 3, $R^7$ and $R^8$ are as defined above, $R^{10}$ represents hydrogen, oxo, alkylsulfonyl, alkylcarbonyl, alkyloxycarbonyl, alkylaminocarbonyl, alkoxy, alkyl or heterocycle,
$R^3$ represents hydrogen, cyano, halogen, alkyl or phenyl, or represents —$(CH_2)_n$-heterocycle or —$(CH_2)_n$-aryl, wherein n denotes a number of 0 to 3, R[4] represents —YR[11], wherein Y represents a direct bond or —(CR[7]R[8])$_p$Y'—, wherein p denotes a number of 0 to 3, R[7] and R[8] are defined as above, Y' is selected from the group consisting of —O—, —S—, —NR[12]—, —NR[12]C(O)—, —C(O)—, —C(O)O—, —C(O)NR[12]—, —S(O)$_q$—, and —S(O)$_q$NR[12]—, wherein R[12] represents hydrogen, alkyl, aryl or heteroaryl, q denotes a number of 0 to 2, R[11] is selected from the group consisting of hydrogen, cyano, halogen, hydroxy, thiol, carboxy, alkyl and —(CH$_2$)$_t$B—R[13], wherein t denotes a number of 0 to 3, B represents heterocycle, heteroaryl or aryl, R[13] represents hydrogen, cyano, halogen, hydroxy, oxo, thiol, carboxy, carboxyalkyl, alkylcarbonyloxy, alkyl, alkoxy, alkylthio, alkylcarbonyl or alkylsulfonyl, R[5] represents hydrogen, alkyl, cycloalkyl, heterocycle or heterocyclylalkyl, R[6] represents —(CR[7]R[8])$_p$—Z-D-W—R[14], wherein Z represents a direct bond, or is selected from the group consisting of —C(O)—, —C(O)O—, —C(O)NR[12]—, and —S(O)$_y$—, y denotes a number of 1 or 2, D represents a direct bond, or represents cycloalkyl, heteroaryl or heterocycle, W represents a direct bond, or represents —NR[7]—, —C(O)—, —C(O)O—, —C(O)NR[12]—, —S(O)$_y$—, —S(O)$_y$NR[12]— or NR[12]S(O)$_y$—, wherein R[14] represents hydrogen, hydroxy, alkyl, alkoxy, heterocycle, heteroaryl, aryl or aralkyl, R[5] and R[6] together represent alkylene chain, where alkyl, alkoxy, aryl, cycloalkyl, heterocycle and heteroaryl may be optionally substituted, and the substituents are one or more selected from the group consisting of hydroxy, halogen, nitrile, amino, alkylamino, dialkylamino, carboxy, alkyl, alkoxy, carboxyalkyl, alkylcarbonyloxy, alkylthio, alkyloxycarbonyl, alkylaminocarbonyl, arylalkoxy and oxo, and pharmaceutically acceptable salts or isomers thereof.

In the above definitions for the compounds of formula (1), the term 'alkyl' means an aliphatic hydrocarbon radical. Alkyl may be saturated alkyl that does not comprise alkenyl or alkynyl moiety, or unsaturated alkyl that comprises at least one alkenyl or alkynyl moiety. "Alkenyl" means a group containing at least one carbon-carbon double bond, and "alkynyl" means a group containing at least one carbon-carbon triple bond. Alkyl may be branched or straight-chain when used alone or in a composite form such as alkoxy.

Alkyl group may have 1 to 20 carbon atoms unless otherwise defined. Alkyl group may be a medium sized alkyl having 1 to 10 carbon atoms. Otherwise, alkyl group may be a lower alkyl having 1 to 6 carbon atoms. Typical examples thereof include, but not limited to, methyl, ethyl, propyl, isopropyl, butyl, isobutyl, t-butyl, pentyl, hexyl, ethenyl, propenyl, butenyl, etc. For example, $C_1$-$C_4$-alkyl has 1 to 4 carbon atoms in the alkyl chain, and is selected from the group consisting of methyl, ethyl, propyl, isopropyl, n-butyl, isobutyl, sec-butyl and t-butyl.

The term 'alkoxy' means an alkyloxy having 1 to 10 carbon atoms unless otherwise defined.

The term 'cycloalkyl' means a saturated aliphatic 3~10 membered cycle unless otherwise defined. Typical examples thereof include, but not limited to, cyclopropyl, cyclobutyl, cyclopentyl, cyclohexyl, etc.

The term 'aryl' include at least one ring having covalent π electron system, for example, monocyclic or fused polycyclic (i.e., cycles that share the adjacent carbon atom pairs) groups. In the present specification, aryl means an aromatic 4~10 membered, preferably 6~10 membered, monocyclic or multicyclic ring including phenyl, naphthyl, etc., unless otherwise defined.

The term 'heteroaryl' means an aromatic 3~10 membered, preferably 4~8 membered, more preferably 5~6 membered cycle that has 1 to 3 hetero atoms selected from N, O and S, and may be fused with benzo or $C_3$-$C_8$ cycloalkyl, unless otherwise defined. The monocyclic heteroaryl includes, but not limited to, thiazole, oxazole, thiophene, furan, pyrrole, imidazole, isoxazole, isothiazole, pyrazole, triazole, triazine, thiadiazole, tetrazole, oxadiazole, pyridine, pyridazine, pyrimidine, pyrazine and the like. The bicyclic heteroaryl includes, but not limited to, indole, indoline, benzothiophene, benzofuran, benzimidazole, benzoxazole, benzisoxazole, benzthiazole, benzthiadiazole, benztriazole, quinoline, isoquinoline, purine, puropyridine and the like.

The term 'heterocycle' means a 3~10 membered, preferably 4~8 membered, more preferably 5~6 membered cycle that has 1 to 3 hetero atoms selected from N, O and S, may be fused with benzo or $C_3$-$C_8$ cycloalkyl, and is saturated or contains 1 or 2 double bonds, unless otherwise defined. The heterocycle includes, but not limited to, pyrroline, pyrrolidine, imidazoline, imidazolidine, pyrazoline, pyrazolidine, pyran, piperidine, morpholine, thiomorpholine, piperazine, hydrofuran and the like.

Other terms and abbreviations in the present specification may be understood to have the meaning conventionally used in this field by a skilled artisan, unless otherwise defined.

Preferred compounds among the compounds of formula (1) above are those wherein n denotes a number of 1 to 3, m denotes 0 or 1, A represents a direct bond, represents phenyl, or represents 6 membered heteroaryl having 1 to 2 nitrogen atoms, X represents C or N, with the proviso that m is 0 when X is N, and m is 1 when X is C, R[1] represents hydrogen, $C_1$-$C_6$-alkyl or —(CH$_2$)$_r$NR[7]R[8], wherein r denotes a number of 2 to 3, and R[7] and R[8] independently of one another represent hydrogen or $C_1$-$C_3$-alkyl, or may together form $C_2$-$C_6$-alkylene chain which is optionally substituted by $C_1$-$C_6$-alkyl and optionally one methylene is replaced by N atom, R[2] represents hydrogen, halogen, $C_1$-$C_6$-alkyl, —(CH$_2$)$_p$CO$_2$R[7], —(CH$_2$)$_p$OR[7], —(CH$_2$)$_p$NR[7]R[8], —NHR[10], —N(H)S(O)$_2$R[7], —NHC(O)R[10], —(CH$_2$)$_p$S(O)$_2$R[7] or —(CH$_2$)$_p$-heterocycle-R[10], p denotes a number of 0 to 3, R[10] represents hydrogen, oxo, $C_1$-$C_6$-alkylsulfonyl, $C_1$-$C_6$-alkylcarbonyl, $C_1$-$C_6$-alkyloxycarbonyl, $C_1$-$C_6$-alkylaminocarbonyl, $C_1$-$C_6$-alkoxy, $C_1$-$C_6$-alkyl or hydroxy-$C_1$-$C_6$-alkyl, or represents 5~6 membered heterocycle which has 1 or 2 nitrogen atoms as the hetero atom, and is optionally substituted by $C_1$-$C_3$-alkyl, R[3] represents hydrogen, halogen or $C_1$-$C_6$-alkyl, represents phenyl optionally substituted by $C_1$-$C_6$-alkoxy, or represents heterocyclyl-$C_1$-$C_5$-alkyl wherein the heterocycle is 5~6 membered, has 1 or 2 hetero atoms selected from N and O, and is optionally substituted by 1 or 2 oxo groups, R[4] represents —YR[11], wherein Y represents a direct bond or —(CR[7]R[8])$_p$Y'—, wherein Y' is selected from the group consisting of —O—, —C(O)—, —C(O)O—, —NHC(O)—, —NR[12]—, —C(O)NR[12]—, —S(O)$_q$—, and —S(O)$_q$NR[12]—, R[12] represents hydrogen or $C_1$-$C_3$-alkyl, q denotes a number of 0 to 2, R[11] is selected from the group consisting of hydrogen, halogen, hydroxy, thiol, carboxy, $C_1$-$C_6$-alkyl, hydroxy-$C_1$-$C_6$-alkyl and —(CH$_2$)$_t$B—R[13], t denotes a number of 0 to 3, B represents $C_6$-$C_{10}$-aryl, represents 5~6 membered heterocycle having 1 or 2 hetero atoms selected from N, O and S, or represents 5~6 membered heteroaryl having 1 or 2 N atoms, R[13] represents hydrogen, halogen, hydroxy, oxo, thiol, carboxy, carboxy-$C_1$-$C_6$-alkyl, $C_1$-$C_6$-alkylcarbonyloxy, $C_1$-$C_6$-alkyl, $C_1$-$C_6$-alkoxy, $C_1$-$C_6$-alkylthio, $C_1$-$C_6$-halogenoalkyl, $C_1$-$C_6$-alkylcarbonyl or $C_1$-$C_6$-alkylsulfonyl, $R^5$ represents hydrogen, $C_1$-$C_6$-alkyl, $C_3$-$C_6$-cycloalkyl, heterocycle or heterocyclyl-$C_1$-$C_6$-alkyl, wherein the heterocycle is a 3~8 membered ring which has 1 to 3 hetero atoms selected from N and O, and is optionally substituted by 1 or 2 oxo groups, $R^6$ represents —$(CR^7R^8)_p$—Z-D-W—$R^{14}$, Z represents a direct bond, or is selected from the group consisting of —C(O)—, —C(O)O—, —C(O)$NR^{12}$—, and —$S(O)_y$—, wherein y denotes a number of 1 to 2, D represents $C_4$-$C_6$-cycloalkyl, or represents 5~6 membered heterocycle which has 1 or 2 hetero atoms selected from N, O and S, and optionally contains an oxo group, W represents a direct bond, or represents —$NR^7$—, —C(O)—, —C(O)O—, —C(O)$NR^{12}$—, —$S(O)_y$—, —$S(O)_yNR^{12}$— or —$NR^{12}S(O)_y$—, $R^{14}$ represents hydrogen, hydroxy, $C_1$-$C_6$-alkyl, hydroxy-$C_1$-$C_6$-alkyl, carboxy-$C_1$-$C_6$-alkyl, $C_6$-$C_{10}$-aryl or $C_6$-$C_{10}$-ar-$C_1$-$C_6$-alkyl, represents 5~6 membered heterocycle which has 1 to 3 hetero atoms selected from N, O and S, and is optionally substituted by 1 or 2 oxo groups, or represents 5~6 membered heteroaryl which has 1 to 3 hetero atoms selected from N, O and S, and is optionally substituted by $C_1$-$C_6$-alkyl, or $R^5$ and $R^6$ together represent $C_2$-$C_6$-alkylene chain.

In the compounds of formula (1) according to the present invention, X is C or N, and the structure for each case may be depicted by the following formula (1a) or (1b).

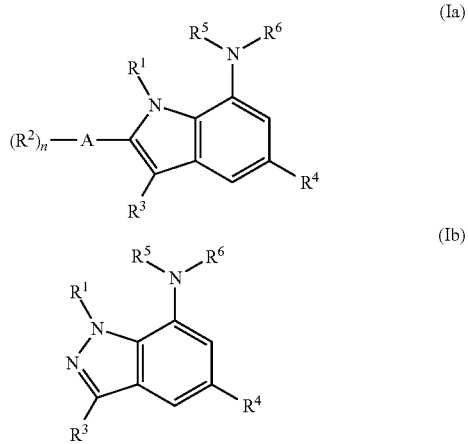

In the compounds of formula (1) of the present invention, the substituent A more preferably represents phenyl, pyridine or 1,4-pyrazine.

The substituent $R^1$ more preferably represents hydrogen, $C_1$-$C_6$-alkyl or di($C_1$-$C_3$-alkyl)amino-$C_2$-$C_3$-alkyl, and most preferably represents hydrogen, methyl or (dimethylamino) ethyl.

The substituent $R^2$ more preferably represents hydrogen, amino, halogen, $C_1$-$C_3$-alkyl, carboxy, carboxy-$C_1$-$C_3$-alkyl, $C_1$-$C_3$-alkoxycarbonyl, $C_1$-$C_3$-alkoxycarbonyl-$C_1$-$C_3$-alkyl, hydroxy-$C_1$-$C_3$-alkyl, $C_1$-$C_3$-alkoxy, —$(CH_2)_pNR^7R^8$, —$NHR^{10}$, —$N(H)S(P)_2R^7$, —$NHC(O)R^{10}$ or —$(CH_2)_p$-heterocycle-$R^{10}$, wherein p, $R^7$, $R^8$ and $R^{10}$ are as defined in the above preferable scope. Most preferably, $R^2$ is selected from the group consisting of hydrogen, methyl, methoxy, fluoro, —$NH_2$, —NHAc, —$NHSO_2Me$, —NHBOC, —NH(1-methyl-piperidine), 1-oxo-2-hydroxy-ethyl, dimethylaminomethyl, hydroxymethyl, hydroxyethyl, carboxy, carboxymethyl, carboxyethyl, —$CH_2$-(2-oxo)piperazine, —$CH_2$-piperazine, —$CH_2$-morpholine, —$CH_2$-[1,1-dioxo-thiomorpholin-4-yl], and —$CH_2$-[4-acetyl-piperazin-1-yl].

The substituent $R^3$ more preferably represents hydrogen, methyl or bromo, represents phenyl optionally substituted by $C_1$-$C_3$-alkoxy, or represents heterocyclyl-$C_1$-$C_3$-alkyl wherein the heterocycle is 5~6 membered, has 1 or 2 hetero atoms selected from N and O, and is optionally substituted by 1 or 2 oxo groups. Most preferably, $R^3$ is selected from the group consisting of hydrogen, methyl, bromo, phenyl, 4-MeO-phenyl, —$CH_2$-(2-oxo-piperazin-4-yl), and —$CH_2$— (morpholin-4-yl).

The substituent $R^4$ more preferably represents —$YR^{11}$, wherein Y is selected from the group consisting of a direct bond, —O—, —C(O)—, —NH—, —CONH—, —$SO_2NH$—, —NHC(O)—, —$CH_2CONH$—, —$CH_2C(O)$—, and —$CH_2SO_2$—. Most preferably, Y is selected from the group consisting of a direct bond, —O—, —C(O)—, —$CH_2C(O)$— and —NHC(O)—. Further, $R^{11}$ is selected from the group consisting of hydrogen, halogen, hydroxy, $C_1$-$C_6$-alkyl and —$(CH_2)_tB$—$R^{13}$, wherein t, B and $R^{13}$ are as defined in the above preferable scope. Most preferably, $R^{11}$ is selected from the group consisting of hydrogen, methyl, ethyl, phenyl, fluoro, chloro, hydroxy, 2-carboxy-pyrrolidin-1-yl, pyrrolidin-1-yl, 4-acetic acid-1,3-thiazolin-2-yl, —$CH_2$-(1,1-dioxo-thiomorpholin-4-yl), and —$CH_2$-(2-oxopiperazin-4-yl).

The substituent $R^5$ more preferably represents hydrogen, $C_1$-$C_6$-alkyl, $C_3$-$C_6$-cycloalkyl, heterocycle or heterocyclyl-$C_1$-$C_6$-alkyl, wherein the heterocycle is a 5~6 membered ring which has 1 or 2 hetero atoms selected from N and O, and is optionally substituted by 1 or 2 oxo groups. Most preferably, $R^5$ is selected from the group consisting of hydrogen, methyl, cyclopentyl, tetrahydropyran-4-yl and $CH_2$— (tetrahydropyran-4-yl).

The substituent $R^6$ more preferably represents —$(CR^7R^8)_p$—Z-D-W—$R^{14}$, wherein Z represents a direct bond, or represents —C(O)—, —C(O)O—, —C(O)NH— or —$S(O)_2$—. D is more preferably selected from the group consisting of cyclopentyl, cyclohexyl, pyrrolidine, tetrahydropyran, tetrahydrofuran and piperidine. W more preferably represents a direct bond, or represents —$SO_2$—, —CO—, —C(O)O— or —$CONR^{12}$—, wherein $R^{12}$ is as defined in the above preferable scope. Most preferably, W is selected from the group consisting of —$SO_2$—, —CO—, —C(O)O—, —CON (Me)—, and —CONH—. $R^{14}$ more preferably represents hydrogen, hydroxy, $C_1$-$C_6$-alkyl, hydroxy-$C_1$-$C_6$-alkyl, $C_6$-$C_{10}$-aryl or $C_6$-$C_{10}$-ar-$C_1$-$C_3$-alkyl, represents 5~6 membered heterocycle which has O or S, and is optionally substituted by 1 or 2 oxo groups, or represents 5~6 membered heteroaryl which has 1 or 2 hetero atoms selected from N, O and S, and is optionally substituted by $C_1$-$C_3$-alkyl. Most preferably, $R^{14}$ is selected from the group consisting of hydrogen, hydroxy, methyl, ethyl, isobutyl, hydroxymethyl, hydroxyethyl, phenyl, benzyl, thiophene, tetrahydrofuran, tetrahydropyran, 1,1-dioxo-tetrahydro-thiopyran, furan, pyridine and 5-methyl-pyridine.

Furthermore, $R^5$ and $R^6$ together with the N atom to which they are attached may more preferably form piperidine.

The compounds of formula (1) according to the present invention can also form a pharmaceutically acceptable salt. Such a "pharmaceutically acceptable salt" includes non-toxic acid addition salt containing pharmaceutically acceptable anion, for example, a salt with inorganic acids such as sulfuric acid, hydrochloric acid, nitric acid, phosphoric acid, hydrobromic acid, hydriodic acid, etc.; a salt with organic carboxylic acids such as tartaric acid, formic acid, citric acid, acetic acid, trichloroacetic acid, trifluoroacetic acid, gluconic acid, benzoic acid, lactic acid, fumaric acid, maleic acid, salicylic acid, etc.; or a salt with sulfonic acids such as methanesulfonic acid, ethanesulfonic acid, benzenesulfonic acid, p-toluenesulfonic acid, naphthalenesulfonic acid, etc. The compounds of formula (I) can also form a pharmaceutically acceptable base addition salt, for example, a salt with alkali metals or alkaline earth metals such as lithium, sodium, potassium, calcium, magnesium, etc.; a salt with amino acids such as lysine, arginine, guanidine, etc.; or an organic salt with dicyclohexylamine, N-methyl-D-glucamine, tris(hydroxymethyl)methylamine, diethanolamine, choline, triethylamine, etc. The compounds of formula (I) of the present invention may be converted to their salts according to any of the conventional methods, and the salt formation can be easily carried out by a skilled artisan based on the structure of formula (1) without additional explanations thereon.

The term 'isomer' in the present specification means those having the same chemical or molecular formula as, but optically or sterically different from, the compounds of formula (1), or salts thereof. The compounds of formula (1) of the present invention may have an asymmetric carbon center(s) in the structure, and so may exist in the form of optical isomer (R or S isomer), racemate, mixture of diastereomers, or individual diastereomer, etc. When the compounds have a double bond, they may exist in the form of geometric isomer (trans or cis isomer). All the isomers and their mixtures are also covered by the present invention.

Hereinafter, the compounds of formula (1) include pharmaceutically acceptable salts and isomers thereof, unless otherwise explained. The salts and isomers should be construed to be covered by the present invention. For the sake of convenience, the present specification briefly expresses them as the compounds of formula (1).

Typical compounds among the compounds of formula (1) are those selected from the following:
Cyclopentyl-[5-methyl-2-(pyridin-2-yl)-1H-indol-7-yl]-amine;
Cyclopentyl-[5-methyl-2-phenyl-1H-indol-7-yl]-amine;
5-Chloro-2-(pyridin-2-yl)-1H-indol-7-yl]-amine;
(Tetrahydropyran-4-yl)-[5-methyl-2-(pyridin-2-yl)-1H-indol-7-yl]-amine;
Cyclopentyl-[2-(pyrazin-2-yl)-1H-indol-7-yl]-amine;
Cyclopentyl-[5-methyl-2-(pyrazin-2-yl)-1H-indol-7-yl]-amine;
Cyclopentyl-[2-(pyridin-2-yl)-1H-indol-7-yl]amine;
(Tetrahydropyran-4-yl)-[2-(pyridin-2-yl)-1H-indol-7-yl]-amine;
Cyclopentyl-[5-phenoxy-2-(pyridin-2-yl)-1H-indol-7-yl]-amine;
Cyclopentyl-[5-ethoxy-2-(pyridin-2-yl)-1H-indol-7-yl]-amine;
Cyclohexyl-[5-methyl-2-(pyridin-2-yl)-1H-indol-7-yl]-amine;
1-[4-[(5-Methyl-2-(pyridin-2-yl)-1H-indol-7-yl)-amino]piperidin-1-yl]ethanone;
(1-Methylpiperidin-4-yl)-[5-methyl-2-(pyridin-2-yl)-1H-indol-7-yl]-amine;
(1-Benzylpyrrolidin-3-yl)[5-methyl-2-(pyridin-2-yl)-1H-indol-7-yl]-amine;
Cyclopentylmethyl-[5-methyl-2-(pyridin-2-yl)-1H-indol-7-yl]-amine;
5-Methyl-(7-piperidin-1-yl)amino-2-(pyridin-2-yl)-1H-indole;
Dimethyl-[5-methyl-2-(pyridin-2-yl)-1H-indol-7-yl]-amine;
Cyclopentyl-[1,5-dimethyl-2-(pyridin-2-yl)-indol-7-yl]-amine;
Cyclopentyl-[5-methyl-2-(6-methylpyridin-2-yl)-1H-indol-7-yl]-amine;
(1-Cyclohexanon-4-yl)-[5-methyl-2-(pyridin-2-yl)-1H-indol-7-yl]-amine;
4-[(5-Chloro-2-phenyl-1H-indol-7-yl)amino]-cyclohexan-1-one;
N-(5-Methyl-2-(pyridin-2-yl)-1H-indol-7-yl)-benzamide;
1-Ethyl-3-[5-methyl-2-(pyridin-2-yl)-1H-indol-7-yl]-urea;
1-Phenyl-3-[5-methyl-2-(pyridin-2-yl)-1H-indol-7-yl]-urea;
Thiophene-2-sulfonic acid (2-pyridin-2-yl-1H-indol-7-yl)-amide;
Thiophene-2-sulfonic acid [5-methyl-2-(pyridin-2-yl)-1H-indol-7-yl]-amide;
Cyclopentyl-methyl-[5-methyl-2-(pyridin-2-yl)-1H-indol-7-yl]-amine;
7-(Cyclopentyl)amino-2-phenyl-1H-indole-5-carboxylic acid ethyl ester;
Cyclopentyl-[5-hydroxymethyl-2-phenyl-1H-indol-7-yl]-amine;
7-(Cyclopentyl)amino-2-phenyl-1H-indole-5-carboxylic acid;
2-[7-(Cyclopentyl)amino-2-phenyl-1H-indol-5-yl]acetic acid ethyl ester;
2-[7-(Cyclopentylamino)-2-phenyl-1H-indol-5-yl]ethanol;
2-[7-(Cyclopentyl)amino-2-phenyl-1H-indol-5-yl]acetic acid;
2-[2-Phenyl-7-(tetrahydropyran-4-yl)amino-1H-indol-5-yl]acetic acid;
2-[2-Phenyl-7-(1,1-dioxo-tetrahydro-thiopyran-4-yl)amino-1H-indol-5-yl]-acetic acid;
(Tetrahydropyran-4-yl)-[2-phenyl-5-(1,1-dioxo-thiomorpholin-4-yl)methyl-1H-indol-7-yl]amine;
(Tetrahydropyran-4-yl)-[2-phenyl-5-(2-oxo-piperazin-4-yl)methyl-1H-indol-7-yl]amine;
Cyclopentyl-[2-(3-fluoro)phenyl-5-(2-oxo-piperazin-4-yl)methyl-1H-indol-7-yl]amine;
(Tetrahydropyran-4-yl)-[2-(4-methoxy)phenyl-5-(1,1-dioxo-thiomorpholin-4-yl)methyl-1H-indol-7-yl]amine;
Cyclopentyl-[3,5-dimethyl-2-phenyl-1H-indol-7-yl]-amine;
(Tetrahydropyran-4-yl)-(5-methyl-2-phenyl-1H-indol-7-yl)-amine;
Cyclopentylmethyl-(5-methyl-2-phenyl-1H-indol-7-yl)-amine;
(Tetrahydropyran-4-yl)-(5-methyl-2-phenyl-1H-indol-7-yl)-amine;
(1-Methylpiperidin-4-yl)-(5-methyl-2-phenyl-1H-indol-7-yl)-amine;
1-[-4-[(5-Methyl-2-phenyl-1H-indol-7-yl)amino]piperidin-1-yl]ethanone;
Cyclopentyl-(5-chloro-2-phenyl-1H-indol-7-yl)-amine;
Cyclohexyl-(5-chloro-2-phenyl-1H-indol-7-yl)-amine;
(Tetrahydropyran-4-yl)-(5-chloro-2-phenyl-1H-indol-7-yl)-amine;
Cyclopentylmethyl-(5-chloro-2-phenyl-1H-indol-7-yl)-amine;
(Tetrahydropyran-4-ylmethyl)-(5-chloro-2-phenyl-1H-indol-7-yl)-amine;
(1-Benzylpyrrolidin-3-yl)-(5-chloro-2-phenyl-1H-indol-7-yl)-amine;
(1-Methylpiperidin-4-yl)-(5-chloro-2-phenyl-1H-indol-7-yl)-amine;
(1,4-Dioxaspiro[4.5]decan-8-yl)-(5-chloro-2-phenyl-1H-indol-7-yl)-amine;
2-[(5-Chloro-2-phenyl-1H-indol-7-yl)amino]propan-1,3-diol;
(Tetrahydropyran-4-yl)-(5-methyl-2-phenyl-1H-indol-7-yl)-methyl-amine;

(Tetrahydropyran-4-ylmethyl)-[2-phenyl-5-(1,1-dioxo-thiomorpholin-4-yl)methyl-1H-indol-7-yl]amine;
Di(tetrahydropyran-4-ylmethyl)-[2-phenyl-5-(1,1-dioxothiomorpholin-4-yl)methyl-1H-indol-7-yl]amine;
Di(tetrahydropyran-4-yl)-[2-phenyl-5-(1,1-dioxo-thiomorpholin-4-yl)methyl-1H-indol-7-yl]amine;
(1-Methyl-piperidinemethyl-4-yl)-[5-fluoro-2-phenyl-1H-indol-7-yl]amine;
2-[4-[(5-Fluoro-2-phenyl-1H-indol-7-yl)amino]piperidin-1-yl]ethanol;
[1-(Tetrahydropyran-4-yl)piperidin-4-yl]-(5-fluoro-2-phenyl-1H-indol-7-yl)amine;
(Tetrahydropyran-4-yl)-(5-phenoxy-2-phenyl-1H-indol-7-yl)-amine;
(Tetrahydropyran-4-ylmethyl)-[2-phenyl-5-(2-oxo-piperazin-4-yl)methyl-1H-indol-7-yl]amine;
(Tetrahydropyran-4-yl)-[5-chloro-1-(2-diethylaminoethyl)-2-phenyl-1H-indol-7-yl]amine;
Dimethyl-(5-chloro-1-methyl-2-phenyl-1H-indol-7-yl)amine;
(Tetrahydropyran-4-yl)-(5-chloro-1-methyl-2-phenyl-1H-indol-7-yl)-methylamine;
(Tetrahydropyran-4-yl)-(5-chloro-3-phenyl-1H-indol-7-yl)-amine;
Cyclopentyl-(5-chloro-3-phenyl-1H-indol-7-yl)-amine;
(Tetrahydropyran-4-ylmethyl)-(5-chloro-3-phenyl-1H-indol-7-yl)-amine;
Cyclopentyl-(5-chloro-3-(morpholin-4-yl)methyl-2-phenyl-1H-indol-7-yl)-amine;
(Tetrahydropyran-4-yl)-(5-chloro-3-(morpholin-4-yl)methyl-2-phenyl-1H-indol-7-yl)-amine;
(Tetrahydropyran-4-yl)-(5-chloro-3-(2-oxo-piperazin-4-yl)methyl-2-phenyl-1H-indol-7-yl)-amine;
Cyclopentyl-(5-chloro-3-(2-oxo-piperazin-4-yl)methyl-2-phenyl-1H-indol-7-yl)-amine;
(Tetrahydropyran-4-ylmethyl)-(5-chloro-3-(2-oxo-piperazin-4-yl)methyl-2-phenyl-1H-indol-7-yl)-amine;
(Tetrahydropyran-4-yl)-(3-bromo-5-(1,1-dioxo-thiomorpholin-4-yl)methyl-2-phenyl-1H-indol-7-yl)-amine;
Cyclopentyl-(3-bromo-5-(1,1-dioxo-thiomorpholin-4-yl)methyl-2-phenyl-1H-indol-7-yl)-amine;
(Tetrahydropyran-4-ylmethyl)-(3-bromo-5-(1,1-dioxo-thiomorpholin-4-yl)methyl-2-phenyl-1H-indol-7-yl)-amine;
(Tetrahydropyran-4-yl)-(5-(1,1-dioxo-thiomorpholin-4-yl)methyl-2-(3-fluorophenyl)-1H-indol-7-yl)-amine;
(Tetrahydropyran-4-yl)-(5-chloro-3-phenyl-1H-indol-7-yl)-amine;
(3-Methylbutyl)-[5-(1,1-dioxo-thiomorpholin-4-yl)methyl-2-(4-methoxyphenyl)-1H-indol-7-yl]-amine;
t-Butyl N-[4-[5-chloro-7-(cyclopentylamino)-1H-indol-2-yl]phenyl]carbamate;
Cyclopentyl-[2-(4-aminophenyl)-5-chloro-1H-indol-7-yl]-amine;
Cyclopentyl-{5-chloro-2-[4-(1-methyl-piperidin-4-yl)aminophenyl]-1H-indol-7-yl}-amine;
N-[4-(5-chloro-7-cyclopentylamino-1H-indol-2-yl)-phenyl]-methanesulfonamide;
Cyclopentyl-{5-(1,1-dioxo-thiomorpholin-4-yl)methyl-2-[4-(acetyl)aminophenyl]-1H-indol-7-yl}-amine;
Dicyclopentyl-{5-(1,1-dioxo-thiomorpholin-4-yl)-2-[4-(acetyl)aminophenyl]-1H-indol-7-yl}-amine;
(Tetrahydropyran-4-yl)methyl-{5-(1,1-dioxo-thiomorpholin-4-yl)-2-[4-(acetyl)aminophenyl]-1H-indol-7-yl}-amine;
Di(tetrahydropyran-4-yl)methyl-{5-(1,1-dioxo-thiomorpholin-4-yl)-2-[4-(acetyl)aminophenyl]-1H-indol-7-yl}-amine;
(Tetrahydropyran-4-yl)-{5-(1,1-dioxo-thiomorpholin-4-yl)-2-[4-(acetyl)aminophenyl]-1H-indol-7-yl}-amine;
(5-Methyl-2-phenyl-1H-indol-7-yl)-piperidin-4-yl-amine;
[1-(Methanesulfonyl)piperidin-4-yl]-(5-methyl-2-phenyl-1H-indol-7-yl)-amine;
2-Hydroxy-1-[4-(5-methyl-2-phenyl-1H-indol-7-yl)aminopiperidin-1-yl]-ethanone;
(5-Chloro-2-phenyl-1H-indol-7-yl)-piperidin-4-yl-amine;
4-(5-Chloro-2-phenyl-1H-indol-7-yl)amino-piperidin-1-yl-carboxylic acid phenylamide;
1-[4-(5-Chloro-2-phenyl-1H-indol-7-yl)amino-piperidin-1-yl]-2-dimethylamino-ethanone;
[5-(1,1-Dioxo-thiomorpholin-4-yl)methyl-2-phenyl-1H-indol-7-yl]-(piperidin-4-yl)methyl-amine;
(5-(1,1-Dioxo-thiomorpholin-4-yl)methyl-2-phenyl-1H-indol-7-yl)-(1-methanesulfonyl-piperidin-4-yl)-amine;
{4-[5-(1,1-Dioxo-thiomorpholin-4-yl)methyl-2-phenyl-1H-indol-7-yl]amino-piperidin-1-yl}-(tetrahydrofuran-2-yl)-methanone;
(5-Fluoro-2-phenyl-1H-indol-7-yl)-[1-(1,1-dioxo-tetrahydrothiopyran-4-yl)-piperidin-4-yl]-amine;
N-(5-Chloro-2-phenyl-1H-indol-7-yl)-N',N'-dimethyl-cyclohexane-1,4-diamine;
N-(5-Chloro-2-phenyl-1H-indol-7-yl)-N'-methyl-cyclohexane-1,4-diamine;
4-(5-Chloro-2-phenyl-1H-indol-7-yl)amino-cyclohexane-1-carboxylic acid;
4-(5-Methyl-2-phenyl-1H-indol-7-yl)amino-cyclohexane-1-carboxylic acid;
4-(5-Chloro-2-phenyl-1H-indol-7-yl)amino-cyclohexane-1-carboxylic acid amide;
4-(5-Chloro-2-phenyl-1H-indol-7-yl)amino-cyclohexanecarboxylic acid methylamide;
(2-(5-Fluoro-2-phenyl-1H-indol-7-yl)amino-acetic acid methyl ester;
2-(5-Fluoro-2-phenyl-1H-indol-7-yl)amino-acetic acid;
2-(5-Phenoxy-2-phenyl-1H-indol-7-yl)amino-acetic acid methyl ester;
2-[(5-Phenoxy-2-phenyl-1H-indol-7-yl)amino]-acetic acid;
2-[(5-Phenoxy-2-phenyl-1H-indol-7-yl)amino]-propionic acid methyl ester;
2-(5-Phenoxy-2-phenyl-1H-indol-7-yl)amino-propionic acid;
2-(5-Chloro-2-phenyl-1H-indol-7-yl)amino-propionic acid;
(5-Chloro-2-phenyl-1H-indol-7-yl)-pyridin-2-yl-amine;
(5-Chloro-2-phenyl-1H-indol-7-yl)-5-methyl-pyridin-2-yl-amine;
(5-Chloro-3-phenyl-1H-indol-7-yl)-(5-methyl-pyridin-2-yl)-amine;
(2S)-1-(7-cyclopentylamino-2-phenyl-1H-indole-5-carbonyl)-pyrrolidine-2-carboxylic acid methyl ester;
(2S)-1-(7-cyclopentylamino-2-phenyl-1H-indole-5-carbonyl)-pyrrolidine-2-carboxylic acid;
(2S)-1-[2-phenyl-7-(tetrahydropyran-4-yl)amino-1H-indole-5-carbonyl]-pyrrolidine-2-carboxylic acid;
2-(7-Cyclopentylamino-2-phenyl-1H-indol-5-yl]-1-pyrrolidin-1-yl-ethanone;
Cyclopentyl-[2-phenyl-5-(2-pyrrolidin-1-yl-ethyl)-1H-indol-7-yl]-amine;
2-[(R)-2-(7-cyclopentylamino-2-phenyl-1H-indol-5-yl)-4,5-dihydro-thiazol-4-yl]-acetic acid;
2-[(R)-2-(2-phenyl-7-(tetrahydropyran-4-yl)methylamino-1H-indol-5-yl)-4,5-dihydro-thiazol-4-yl]-acetic acid;
3-(7-Cyclopentylamino-5-chloro-1H-indol-2-yl)-benzoic acid methyl ester;
3-(7-Cyclopentylamino-5-chloro-1H-indol-2-yl)-benzoic acid;

[3-(5-Chloro-7-cyclopentylamino-1H-indol-2-yl)-phenyl]-methanol;
{3-[5-Chloro-7-(tetrahydropyran-4-yl)amino-1H-indol-2-yl]-phenyl}-methanol;
2-{3-[5-Chloro-7-(tetrahydropyran-4-ylmethyl)amino-1H-indol-2-yl]-phenyl}-acetic acid;
2-[3-(5-Chloro-7-cyclopentylamino-1-H-indol-2-yl)-phenyl]-acetic acid;
2-{3-[5-Chloro-7-(tetrahydropyran-4-yl)amino-1H-indol-2-yl]-phenyl}-acetic acid;
2-{3-[5-Chloro-7-(tetrahydropyran-4-ylmethyl)amino-1H-indol-2-yl]-phenyl}-acetic acid methyl ester;
2-[3-(5-Chloro-7-cyclopentylamino-1H-indol-2-yl)-phenyl]-acetic acid methyl ester;
2-{3-[5-Chloro-7-(tetrahydropyran-4-yl)amino)-1H-indol-2-yl]-phenyl}-acetic acid methyl ester;
[2-(5-Chloro-7-cyclopentylamino-1H-indol-2-yl)-phenyl]-methanol;
2-(5-Chloro-7-cyclopentylamino-1H-indol-2-yl)-benzoic acid;
2-(5-Chloro-7-cyclopentylamino-1H-indol-2-yl)-benzoic acid methyl ester;
[4-(5-Chloro-7-cyclopentylamino-1H-indol-2-yl)-phenyl]-methanol;
2-{4-[5-Chloro-7-(tetrahydropyran-4-yl)amino-1H-indol-2-yl]phenyl}-ethanol;
4-(5-Chloro-7-cyclopentylamino-1H-indol-2-yl)-benzoic acid;
2-{4-[5-Chloro-7-(tetrahydropyran-4-ylmethyl)amino-1H-indol-2-yl]phenyl}-acetic acid;
2-[4-(5-Chloro-7-cyclopentylamino-1H-indol-2-yl)phenyl]-acetic acid;
2-{4-[5-Chloro-7-(tetrahydropyran-4-yl)amino-1H-indol-2-yl]phenyl}-acetic acid;
4-(5-Chloro-7-cyclopentylamino-1H-indol-2-yl)benzoic acid methyl ester;
4-(7-Cyclopentylamino-5-methyl-1H-indol-2-yl)benzoic acid methyl ester;
2-{4-[5-Chloro-7-(tetrahydropyran-4-ylmethyl)amino-1H-indol-2-yl]phenyl}-acetic acid methyl ester;
2-[4-(5-Chloro-7-cyclopentylamino-1H-indol-2-yl)phenyl]acetic acid methyl ester;
2-{4-[5-Chloro-7-(tetrahydropyran-4-yl)amino-1H-indol-2-yl]phenyl}-acetic acid methyl ester;
[5-Chloro-2-(3-dimethylaminoethylphenyl)-1H-indol-7-yl]-(tetrahydropyran-4-yl)-amine;
[5-Chloro-2-(3-morpholin-4-ylmethylphenyl)-1H-indol-7-yl]-(tetrahydropyran-4-yl)-amine;
[5-Chloro-2-(3-pyrrolidin-4-ylmethylphenyl)-1H-indol-7-yl]-(tetrahydropyran-4-yl)-amine;
1-{4-[3-(5-Chloro-7-tetrahydropyran-4-ylamino-1H-indol-2-yl)-benzyl]-piperazin-1-yl}-ethanone;
{5-Chloro-2-[3-(2-oxo-piperazin-4-yl)ethylphenyl]-1H-indol-7-yl}-(tetrahydropyran-4-yl)-amine;
{5-Chloro-2-[3-(1,1-dioxo-thiomorpholin-4-yl)ethylphenyl]-1H-indol-7-yl}-(tetrahydropyran-4-yl)-amine;
Cyclopentyl-(1H-indazol-7-yl)-amine;
(Tetrahydropyran-4-yl)-(1H-indazol-7-yl)-amine;
Cyclopentyl-(5-methyl-1H-indazol-7-yl)-amine;
(5-Methyl-1H-indazol-7-yl)-(tetrahydropyran-4-yl)-amine;
Cyclopentyl-[3-(4-methoxyphenyl)-1H-indazol-7-yl]-amine;
[3-(4-Methoxyphenyl)-1H-indazol-7-yl)]-(tetrahydropyran-4-yl)-amine;
[3-(4-Methoxyphenyl)-1H-indazol-7-yl)-(tetrahydropyran-4-ylmethyl)-amine;
(Tetrahydropyran-4-yl)-[5-(1,1-dioxo-thiomorpholin-4-yl)methyl-3-phenyl-2-trimethylsilyl-1H-indol-7-yl)-amine;
(Tetrahydropyran-4-yl)-[5-(1,1-dioxo-thiomorpholin-4-yl)methyl-3-phenyl-1H-indol-7-yl)-amine; and
(Tetrahydropyran-4-yl)-[3-bromo-5-(morpholin-4-yl)methyl-2-phenyl-1H-indol-7-yl]-amine.

The present invention also provides processes for preparing the compounds of formula (1). Hereinafter, the processes for preparing the compounds of formula (1) are illustrated by exemplary reaction schemes for the purpose of better understanding. However, a skilled artisan in the field to which the present invention pertains may prepare the compounds of formula (1) via various routes according to their structures, and such processes should be construed to fall under the scope of the present invention. In other words, the compounds of formula (1) may be prepared by optionally combining various synthetic methods which are described in the present specification or disclosed in the prior arts. The processes for preparing the compounds of formula (1) cover even such processes, and are not limited to those explained below.

First, the compounds of formula (1) may be prepared according to the following Reaction Scheme (1) by reducing the nitro group of the compound (2) to produce the amine compound (3), and by carrying out a reductive amination reaction or coupling reaction in the presence of a base on the compound (3) with compound (4) or compound (5).

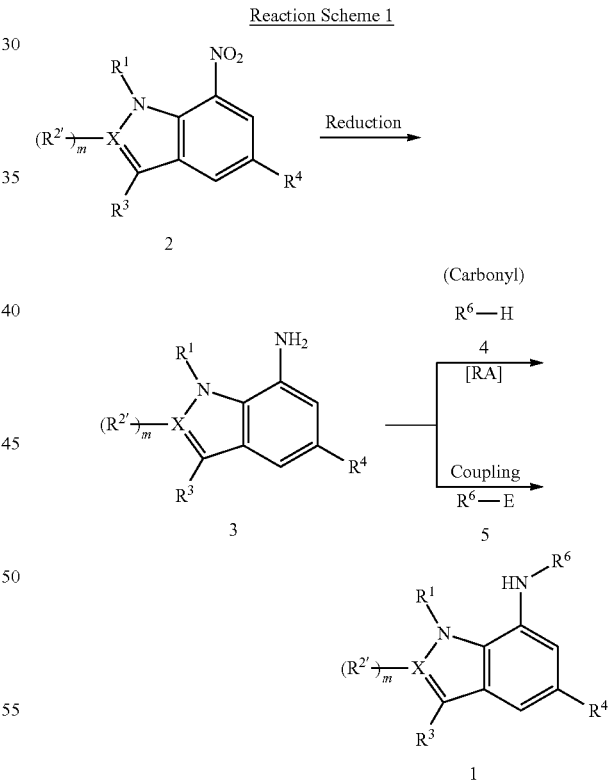

in the above Reaction Scheme (1),
m, X, $R^1$, $R^3$, $R^4$ and $R^6$ are as defined above,
$R^{2'}$ represents $(R^2)_n$-A-, and
E represents a leaving group or linker, preferably may be chloro, bromo or iodo, a form of mixed anhydride, isocyanate or isothiocyanate.

In Reaction Scheme (1), the reduction may be conducted using an acid catalyst and a metal, or a metallic catalyst in the presence of hydrogen gas. Iron, zinc, lithium, sodium, or tin (usually, tin chloride) may be used as the metal, and inorganic acid such as hydrochloric acid, sulfuric acid, nitric acid, phosphoric acid, etc.; organic carboxylic acid such as acetic acid, trifluoroacetic acid, etc.; or ammonium chloride, etc. may be used as the acid catalyst. Also in the reduction reaction using a metallic catalyst in the presence of hydrogen gas, palladium, nickel, platinum, ruthenium, rhodium etc. may be mentioned as the metallic catalyst, where the conventional hydrogen gas pressure ranges 1~3 atm.

$R^6$ in the formula (4) includes a carbonyl group, where the carbonyl group means an aldehyde or a ketone. The reductive amination (RA) reaction may use sodium triacetoxyborohydride {$NaBH(OAc)_3$} or sodium cyanoborohydride ($NaBH_3CN$), etc.

The coupling reaction may be carried out by reacting the compound (3) with the compound (5) using a base such as $Et_3N$, $EtN(iPr)_2$, DBU, N-methyl-morpholine, methyl-pyrrolidine, $K_2CO_3$, etc.

In the case of an indole compound wherein X is C, those having a simple substituent (7-nitro-indole, 2,3-dimethyl-7-nitro-indole, etc.) may be commercially available, and most of them may be synthesized by cyclizing the acetylene intermediate such as the compound (8) in the following Reaction Scheme (2). Further, the compound (8) may be obtained via a coupling reaction of halobenzene compound (6) with acetylene compound (7).

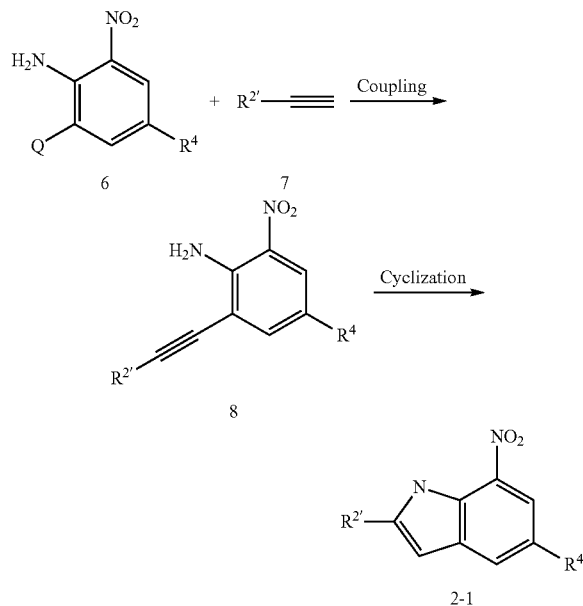

Reaction Scheme 2 in the above Reaction Scheme (2), $R^{2'}$ and $R^4$ are as defined above, and

Q represents iodo or bromo.

The compound (2-1) may be prepared by a cyclization reaction of the acetylene compound (8) in the presence of a base selected from $KOBu^t$, $K_2CO_3$, DBU, etc. or a metallic catalyst selected from CuI, Pd(II), etc.

The preparation of acetylene compound (8) may be carried out by adding a base in the presence of a metallic catalyst, where Pd(II), Cu(I), etc. are used as the metallic catalyst, and $Et_3N$, $Et_2N(iPr)$, DBU, N-methyl-morpholine, methyl-pyrrolidine, $K_2CO_3$, etc. are used as the base.

The acetylene compound (7) is usually commercially available, or may be prepared by a coupling reaction of acetylene in the presence of Pd(II) or Cu(I) and a base according to an art-known method [Synthesis, 2004 5961; Bioorganic & Medicinal Chemistry, 13, 2005, 197~209; Journal of Organic Chemistry, 71, 2006, 167~175]. The acetylene being used is trimethylsilylacetylene or 2-methyl-3-butyn-2-ol, and the base being used is diethylamine, triethylamine, diisopropylethylamine, etc.

The halobenzene compound (6) may be obtained from a nitroaniline compound (13) using iodine or bromine as depicted in the following Reaction Scheme (3).

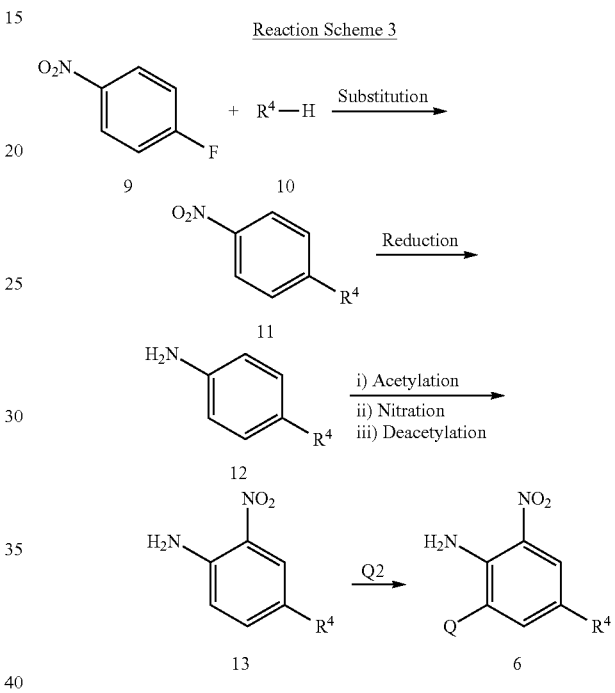

Reaction Scheme 3 in the above Reaction Scheme (3), $R^4$ and Q are as defined above.

The nitroaniline compound (13) is commercially available, or may be prepared via acetylation, nitration and deacetylation from commercially available nitro compound (11) or aniline compound (12). The aniline compound (12) that is not easy to obtain commercially can be prepared from the nitro compound (11). Likewise, the nitro compound (11) can also be commercially available, or prepared from 4-fluoro-nitrobenzene compound (9). In the Reaction Scheme (3), the compound (10) of formula $R^4$—H means commercially available alcohols and amines.

The halogenating material for preparing the compound (6) may be selected from iodine, bromine, iodomonobromide and iodomonochloride, which may be used along with a silver ion such as silver nitrate ($AgNO_3$), silver carbonate ($AgCO_3$), silver sulfate ($Ag_2SO_4$), etc.

Conventional acetylation and nitration reactions are used for obtaining the compound (13) from the compound (12). The nitration reaction may be carried out using undiluted nitric acid under a low temperature (−15 to 0° C.), or various solvents such as dichloroethane or dichloromethane may be used together. The reduction reaction of nitro group may also be carried out in the same manner as the process for preparing the compound (3) in Reaction Scheme (1) above.

As depicted in the following Reaction Scheme (4), the indole compound may be obtained by directly reacting the trifluoroacetyl-substituted compound (6-1) with the acetylene compound (7).

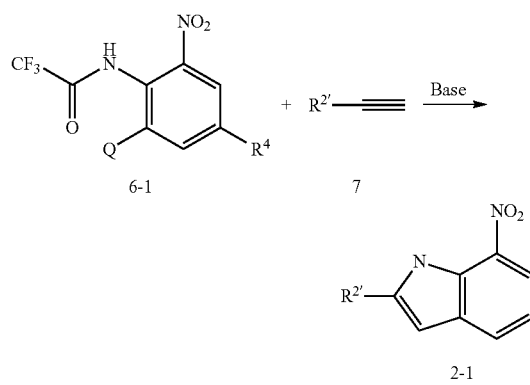

In the meantime, the indole compound (2-2) may be obtained from the nitroaniline compound (13) according to Fisher indole synthesis, as depicted in the following Reaction Scheme (5).

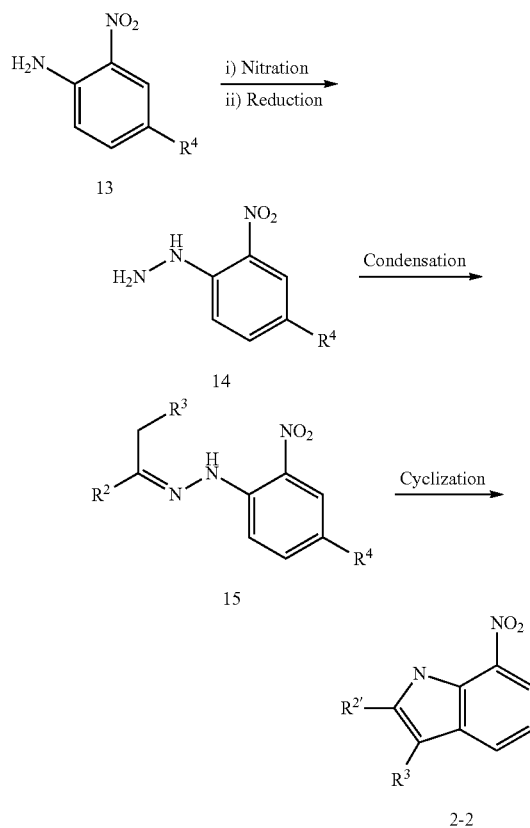

in the above Reaction Scheme (5), $R^{2'}$, $R^3$ and $R^4$ are as defined above.

The compound (14) is commercially available, or may be prepared by modifying the amine group of the compound (13) to hydrazine group according to the art-known method [Journal of the America Chemical Society, 198(48), 15374~75, 2006].

Hydrazine may be formed by reacting amine group with $NaNO_2$ in the presence of hydrochloric acid to introduce nitro group, and by reducing the nitro group using $SnCl_2$, where the reaction is made using hydrochloric acid solution having a concentration of 1 to 12N, preferably 4 to 8N.

The hydrazone compound (15) may be prepared via condensation of the hydrazine compound (14) with the ketone compound in the presence of a base. As the base, metal hydroxides such as sodium hydroxide, lithium hydroxide, etc., metal carbonates such as sodium bicarbonate, potassium carbonate, etc., metal acetates such as sodium acetate, etc., organic bases such as triethylamine, pyridine, etc., preferably sodium acetate, sodium bicarbonate, etc. may be mentioned.

The preparation of the compound (2-2) through a cyclization may be carried out in the presence of an acid catalyst, where the acid may be polyphosphoric acid, hydrochloric acid, p-toluenesulfonic acid, sulfuric acid, acetic acid, etc., preferably polyphosphoric acid. Polyphosphoric acid may be used either alone or in the state of being mixed with aromatic hydrocarbons such as benzene, toluene, etc. The reaction temperature ranges between 25 and 150□, and the reaction time ranges usually between 5 min and 60 h, preferably 5 min and 12 h.

The compound (2-3) having a substituent at 3-position of the indole ring may be prepared via a cyclization of the TMS-substituted acetylene compound (18) together with the compound (6), as depicted in the following Reaction Scheme (6).

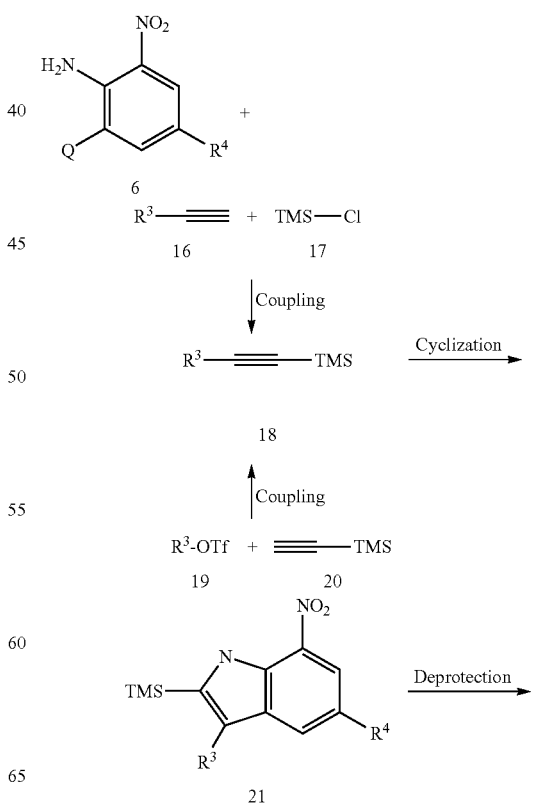

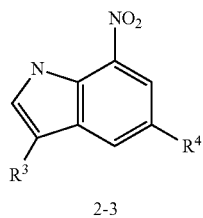

in the above Reaction Scheme (6), $R^3$ and $R^4$ are as defined above.

The compounds (16), (17) and (20) are commercially available, and the compound (19) may be obtained by a conventional tosylation reaction from an alcohol or phenol. Preparations of the TMS compound (18) or the compound (21) are the same as the process for preparing the compound (2-1) in Reaction Scheme (2) above. The compound (2-3) may be obtained by removing TMS group, where TBNF (tetrabutylammoniumfluoride) and a base can be used.

The compound (2-4) wherein 3-position of the indole ring is substituted may be prepared by introducing formyl group to the indole compound (22) to give the aldehyde compound (23), and by carrying out reductive amination reaction.

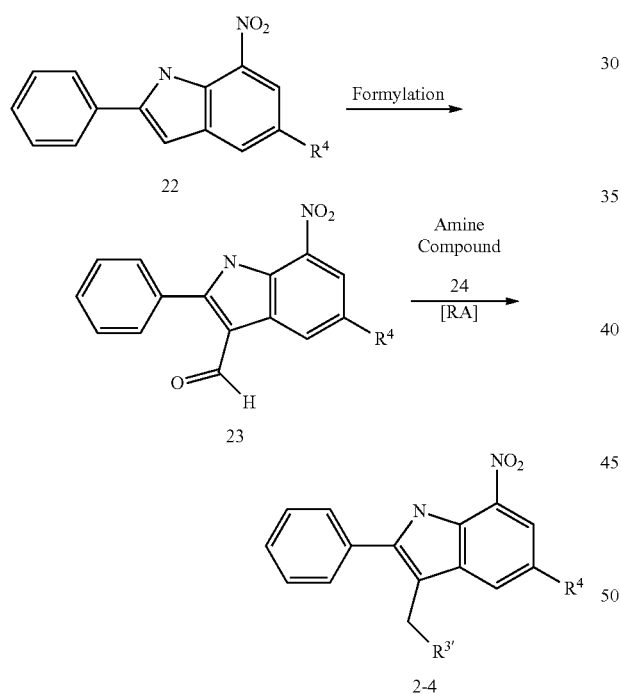

in the above Reaction Scheme (7),
$R^4$ is as defined above, and
$R^{3'}$ represents heterocycle containing amine.

Formylation reaction may be carried out using DMF in the presence of a base, where as the base, n-butyllithium, t-butyllithium, LDA (lithiumdiisopropylamine), KHMDS (potassiumhexamethyldisilane), etc. can be mentioned. Reductive amination reaction may be carried out in the same manner as the process for preparing the compound (1) in Reaction Scheme (1) above.

The indazole compound (27) or (33) may be prepared as depicted in the following Reaction Scheme (8). First, the indazole ring itself can be easily obtained by heating the nitroaniline compound in the presence of acetic acid according to the conventional manner. The compound (33) wherein 3-position of the indazole ring is substituted may be obtained via a substitution reaction using the iodo compound.

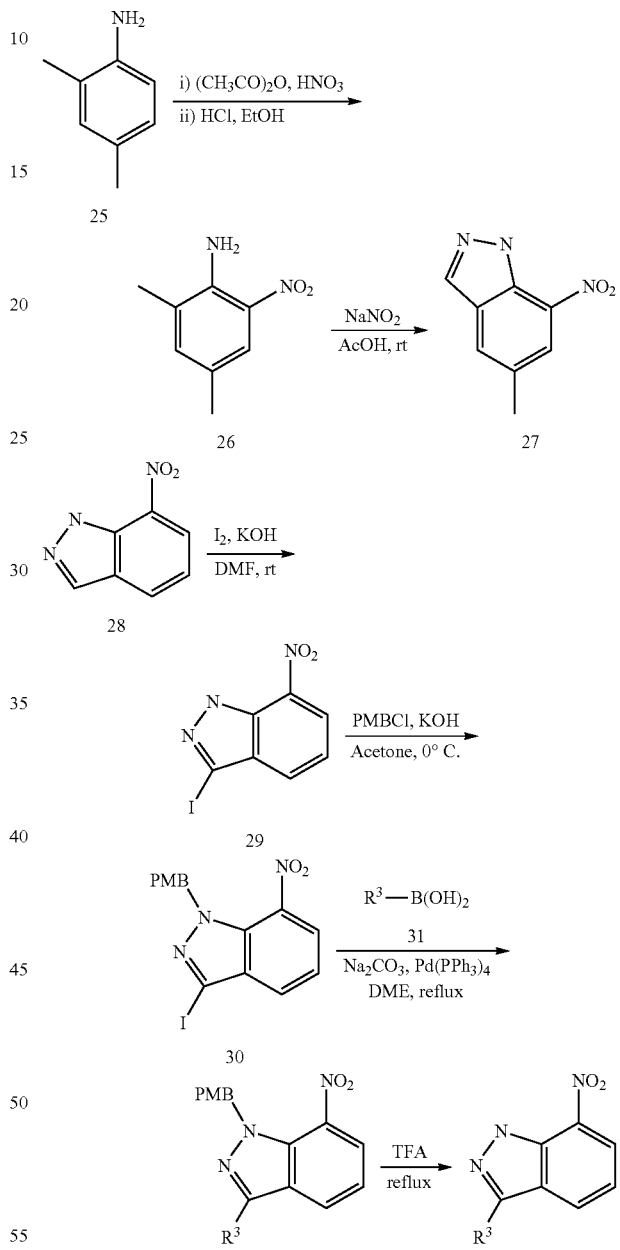

The compounds whose preparation methods are not specifically explained in the present specification are known per se, or those that can be prepared from a known compound according to a known process or a similar process thereto.

In the processes according to the present invention, mixtures are conventionally separated by column chromatography. In the case of a final product, it can be separated after completion of reaction by recrystallization or normal or reverse-phased HPLC (Waters, Delta Pack, 300×50 mmI.D., C18 5 μm, 100 A). When the product is purified through recrystallization or HPLC, the compound may be obtained in the form of a salt with trifluoroacetic acid. When a salt with hydrochloric acid is desirable, ion exchange resin can be used.

As explained above, the compounds according to the present invention, starting materials, intermediates, etc. for the preparation thereof may be obtained by various processes, and such processes for preparing the compounds of formula (1) should be construed to fall under the scope of the present invention.

Effect

The present invention further provides a composition for the prevention or treatment of necrosis and associated diseases, which comprises therapeutically effective amount of the compounds of formula (1), pharmaceutically acceptable salts or isomers thereof as an active ingredient together with pharmaceutically acceptable carriers or diluents.

The present invention further provides a method for the prevention or treatment of necrosis and associated diseases using the above described composition.

Necrosis and associated diseases which can be treated and/or prevented according to the present invention include acute/chronic hepatic disease (e.g. hepatitis, hepatic fibrosis, hepatocirrhosis), neurodegenerative disease (e.g. dementia, Parkinson's disease, Huntington's disease), ischemic cardiac disease, reperfusion injury, ischemic stroke or ischemic injury, pancreatitis, bacterial/viral sepsis, diabetes mellitus or diabetic complications, diabetic vascular disease [in particular, these diabetes are caused by pancreatic cell destroying substances, and mediated by virus, hyperglycemia, fatty acid, diet, toxin, streptozotocin and the like], necrotizing procolitis, cystic fibrosis, rheumatoid arthritis, degenerative arthritis, nephropathy, bacterial infection, viral infection (e.g. HIV), multiple sclerosis, leukemia, lymphoma, neonatal respiratory distress syndrome, asphyxia, tuberculosis, endometriosis, angiasthenia, psoriasis, chilblain, steroid treatment complications, gangrene, pressure sores, hemoglobinuria, burns, hyperthermia, Crohn's disease, celiac disease, compartment syndrome, spiral cord injury, glomerulonephritis, muscular dystrophy, metabolic inherited disease, mycoplasmal disease, anthrax, Andersen's disease, congenital mitochondrial disease, phenylketonuria, placental infarction, syphilis, aseptic necrosis etc. In addition, necrosis and associated diseases caused by drugs and toxic substances are selected from the group consisting of the necrosis associated with alcoholism, the exposure to, and/or administration and/or self-administration of, cocaine, drugs (e.g., paracetamol), antibiotics, anti-cancer agent, adriamycin, puromycin, bleomycin, NSAID, cyclosporine, chemical toxins (e.g., carbon tetrachloride, cyanide, methanol, ethylene glycol), poison gas, agrochemicals, heavy metals (e.g., lead, mercury, cadmium), or injury due to the exposure to radioactivity/UV and associated necrosis thereof.

In particular, the composition according to the present invention exhibits not only the effects for hepatoprotection and hepatic functional improvement, but also shows the prophylactic and therapeutic effects on the chronic hepatic disease such as fatty liver, hepatic fibrosis, hepatocirrhosis, etc. and acute/chronic hepatic disease such as hepatitis, etc. caused by virus or drugs. Consequently, complications of hepatic disease including, but not limited to, portal hypertension also may be prevented or treated. More particularly, the medical composition according to the present invention is also effective for the treatment or prevention of the hepatic disease selected from liver transplantation, alcoholic or non-alcoholic fatty liver, hepatic fibrosis, hepatocirrhoisis and hepatitis caused by virus or drugs, and is effective for alcoholic acute/chronic hepatic disease.

Further, the composition according to the present invention is effective for the treatment or prevention of fatty acid-induced fatty liver or acute/chronic hepatic disease derived from fatty liver.

As used herein, "treatment" means the interrupting or delaying the progress of the disease when applied to the subject showing the onset of disease symptoms, and "prevention" means the interrupting or delaying the sign of the onset of disease when applied to the subject that does not show, but is at risk of, the onset of disease symptoms.

The above-mentioned "pharmaceutical composition" may comprise pharmaceutically acceptable carriers, diluents, excipients, or their combinations, if needed, together with the compounds of the present invention. Pharmaceutical composition facilitates the administration of the compound into a living organism. There exist a number of techniques to administer the compound, and they include, but not limited to, oral, injectable, aerosol, parenteral and topical administration.

As used herein, "carrier" means a substance which facilitates the incorporation of the compound into the cells or tissues. For example, dimethylsulfoxide (DMSO) is a typical carrier which is used to facilitate the introduction of various organic compounds into the cells or tissues of living organisms.

As used herein, "diluent" is defined as a substance that is diluted in water which dissolves the compound, as well as stabilizes the biologically active form of the subject compound. The salts dissolved in buffer solution are utilized as diluents in the art. Typically used buffer solution is phosphate buffered saline which mimics the salt form of human solution. Buffer diluents rarely alter the biological activities of the compound, as the buffer salts can control the pH of solution at low concentration.

As used herein, "pharmaceutically acceptable" means the property that does not impair the biological activities and physical properties of the compound.

The compounds of the present invention can be formulated as various pharmaceutical dosage forms according to the desired purpose. For the preparation of the pharmaceutical composition of the present invention, active ingredient, specifically, the compounds of formula (1), pharmaceutically acceptable salt or isomer thereof is mixed together with various pharmaceutically acceptable carriers which can be selected according to the formulation to be prepared. For example, the pharmaceutical composition of the present invention can be formulated as injectable preparation, oral preparation, etc., according to the desired purpose.

The compounds of the present invention can be formulated by the methods known in the art, which utilize pharmaceutical carriers and excipients known in the art, and be incorporated into the containers of unit dose form or mult-dose form. The form of the preparation can be solutions, suspensions or emulsions in oily or aqueous media, and contain typical dispersing agents, suspending agents or stabilizers. Further, for example, it can be a form of dry powder which is intended to be reconstructed by dissolving in sterile, pyrogen-free water prior to use. The compounds of the present invention also can be formulated into suppository forms utilizing typical suppository base such as cocoa butter or other glycerides. As solid dosage forms for oral administration, capsules, tablets, pills, powder and granule can be prepared, and capsules and tablets are especially useful. Preferably, tablets and pills are prepared as enteric coated forms. Solid dosage forms can be prepared by mixing the compounds of the present invention together with carriers such as one or more inert diluents such as sucrose, lactose, starch, etc., lubricants such as magnesium stearate, disintegrant, binder, etc.

If needed, the compounds of the present invention or the pharmaceutical compositions containing the same can also be administered in combination with other active agents including cytoprotective agents with various action mechanisms of different types, especially the existing agents utilized for hepatoprotection, hepatic functional improvement, and prevention or treatment of hepatic disease—hepatocyte regeneration promoters, hepatic functional adjuvants, anti-viral agents, immunosuppressants, fibrosis inhibitors, etc.

The compounds of the present invention or the pharmaceutical compositions containing the same can be co-administered with prophylactic or therapeutic agents for any drug-derived necrosis and associated diseases. These drugs include the drugs for any disease group such as antibiotics, anti-cancer agents, anti-viral agents, anti-infectives, anti-inflammatory agents, anti-coagulants, lipid-improving agents, cell death inhibitors, anti-hypertensive agents, anti-diabetic/anti-obesity agents, therapeutic agents for cardiovascular disease, therapeutic agents for neurodegenerative disease, anti-aging agents, therapeutic agents for metabolic disease, etc.

The compounds of the present invention or the pharmaceutical compositions containing the same can be used for the prevention of the cell injury and subsequent necrosis and associated diseases derived by various causes such as toxins, and these causes include reactive oxygen species (ROS), heavy metals, alcohol, food, supplement, radiation, diet, etc.

The dosage of the compounds of formula (1) depends on the prescription of a physician, taking into account such factors as body weight, sex, age, condition of health, and diet of the patient, specific nature of the disease, administration time of the agent, administration method, mixing ratio of agents, and severity of the disease, etc. However, dosage needed for the treatment of an adult is typically from about 1.0 mg to 2,000 mg per day, depending on the intensity and frequency of the administration. When administered to an adult via intramuscular or intravenous routes, total dosage typically from about 1.0 mg to 300 mg per day will be sufficient when separately administered in a single dosage, but for some patients a higher daily dosage may be desirable.

The present invention further provides a method of preparing the composition for the prevention or treatment of necrosis and associated diseases, which comprises the step of mixing the compounds of formula (1), pharmaceutically acceptable salts or isomers thereof as an active ingredient together with pharmaceutically acceptable carriers or diluents.

BEST MODE FOR CARRYING OUT THE INVENTION

The present invention will be more specifically explained by the following preparations and examples. However, it should be understand that they are intended to illustrate the present invention but not in any manner to limit the scope of the present invention. In the following preparations and examples, M means molar concentration, and N means normal concentration.

The following Preparations explain more in detail preparations of intermediates that are required for syntheses of Example compounds. The abbreviations used in the following Preparations and Examples are as follows.

Ac: acetyl
BOC: t-butoxycarbonyl
Bu: butyl
Bn: benzyl
c-Pen: cyclopentyl
c-Hex: cyclohexyl
DME: dimethoxyethane
DCM: dichloromethane
DIPEA: diisopropylethylamine
DMAP: 4-dimethylaminopyridine
DMF: N,N-dimethylformamide
EDC: 1-(3-dimethylaminopropyl)-3-ethylcarbodiimide, hydrochloride
Et: ethyl
Hex: n-hexane
HOBT: hydroxybenzotriazole
HBTU: 2-(1H-benzotriazol-1-yl)-1,1,3,3-tetramethyluronium hexafluorophosphate
i-Pr: isopropyl
i-Pen: isopentyl
KHMDS: potassium bis(trimethylsilyl)amide
LDA: lithium diisopropylamine
Me: methyl
Ph: phenyl
Pid: piperidine
Piz: piperazine
Pyd: pyrrolidine
Pro: proline
PMB: paramethoxybenzyl
TEA: triethylamine
TFA: trifluoroacetic acid
THF: tetrahydropyran
THP: tetrahydropyran
TMS: trimethylsilyl
TBNF: tetrabutylammoniumfluoride Preparation 1: 2-Nitro-4-phenoxy-phenylamine Step A: N-(4-phenoxy-phenyl)-acetamide Commercial available 4-phenoxy-aniline (4.16 g, 20.8 mmol) was dissolved in dichloromethane (100 mL), and triethylamine (3.05 g, 31.1 mmol) and acetic anhydride (2.22 g, 20.8 mmol) were added in drops. The mixture was stirred for 1 h at 0° C. to room temperature. After completion of the reaction, the mixture was filtered using dichloromethane and crystallized to give the title compound (4.50 g, 18.6 mmol)

Step B: N-(2-nitro-4-phenoxy-phenyl)acetamide

N-(4-phenoxy-phenyl)-acetamide (1.00 g, 4.03 mmol) prepared in Step A was dissolved in fuming nitric acid (2 mL), and the mixture was stirred for 2 h at −15° C. After completion of the reaction, the reaction mixture was poured into 100 mL of ice water, which was then extracted with ethyl acetate. The extracted organic solution was dried over anhydrous magnesium sulfate, the solvent was removed under reduced pressure, and the residue was purified by column chromatography to give the title compound (0.67 g, 2.33 mmol).

Step C: 2-Nitro-4-phenoxy-phenylamine

N-(2-nitro-4-phenoxy-phenyl)acetamide (0.67 g, 2.33 mmol) prepared in Step B was dissolved in methanol (5 mL), 6.0N sodium hydroxide (1.5 mL) was added thereto, and the mixture was stirred for 18 h at room temperature. After completion of the reaction, 6.0N aqueous hydrochloric acid solution (1.3 mL) and ammonium chloride solution (100 mL) were added thereto. The reaction mixture was extracted with ethyl acetate, dried over magnesium sulfate, and recrystallized from dichloromethane and hexane to give the title compound (521 mg, 2.12 mmol).

Mass [M+H]=230

Preparations 2 to 7

Commercially available anilines were reacted according to the same procedure as Preparation 1 to synthesize the Preparation Compounds in the following table.

| Preparation | $R^4$ | Mass [M + 1] |
|---|---|---|
| 2 | chloro | 172 |
| 3 | ethoxy | 182 |
| 4 | fluoro | 156 |
| 5 | $CO_2Et$ | 196 |
| 6 | $CH_2$—$CO_2Et$ | 210 |
| 7 | methoxy | 168 |

Preparation 8: 5-Methyl-2-(pyridin-2-yl)-7-nitro-1H-indole

Step A: (2-Nitro-4-methyl-phenyl)-hydrazine hydrochloride

The commercially available 4-methyl-2-nitro-phenylamine (40 g, 0.23 mol) was dissolved in 12N-hydrochloric acid (100 mL), to which sodium nitrite (16 g, 0.23 mol) dissolved in water (50 mL) was slowly added in drops at 0° C. The reaction mixture was stirred for 30 min at 0° C. After lowering the temperature of the reaction mixture to 0° C., tin (II) chloride (132 g, 0.70 mol) dissolved in 100 mL of 12N-hydrochloric acid was slowly added in drops thereto. The reaction mixture was stirred for 3 h at 0° C. to room temperature. The resulting yellow solid was filtered, washed with a small amount of 6N—HCl, and dried to give the title compound (30 g, Yield 63%).

$^1$H-NMR (400 HMz, DMSO-$d_6$); δ 9.21 (s, 1H), 7.98 (d, J=2.4 Hz, 1H), 7.66 (d, J=9.6 Hz, 1H), 7.55 (dd, J=2.4, 9.6 Hz, 1H), 4.74 (br s, 2H)

Step B: N-[(4-methyl-2-nitro-phenyl)-N'-[1-(pyridin-2-yl)-ethylidene]hydrazine hydrochloride (2-Nitro-4-methyl-phenyl)-hydrazine hydrochloride (30 g, 0.14 mol) prepared in Step A and pyridinemethylketone (14.4 mL, 0.16 mol) were dissolved in methanol (300 mL), and sodium acetate (14.2 g, 0.17 mol) was added thereto. The reaction mixture was stirred for 8 h at room temperature. The resulting yellow solid was filtered, washed with water and methanol, and dried to give the title compound (30 g, Yield 82%).

Step C: 5-Methyl-2-(pyridin-2-yl)-7-nitro-1H-indole

To N-[(4-methyl-2-nitro-phenyl)-N'-[1-(pyridin-2-yl)-ethylidene]hydrazine hydrochloride (13 g, 46 mmol) prepared in Step B was added polyphosphoric acid (100 mL), which was then heated for 4 h at 100° C. After completion of the reaction, water was added to the reaction mixture, and the water insoluble solid was collected. This solid was washed with water and dried to give the title compound (6.0 g, Yield 49%).

Mass [M+H]=253

Preparations 9 to 15

Commercially available nitroanilines, the compound prepared in Preparation 3, pyridine, pyrazineketone, etc. were reacted according to the same procedure as Preparation 8 to synthesize the Preparation Compounds in the following table.

| Preparation | $R^2$—A | $R^4$ | $R^3$ | Mass [M + 1] |
|---|---|---|---|---|
| 9 | pyridin-2-yl | H | H | 239 |
| 10 | pyrazin-2-yl | Me | H | 254 |
| 11 | pyrazin-2-yl | H | H | 240 |
| 12 | 5-methyl-pyridin-2-yl | H | H | 253 |
| 13 | pyridin-2-yl | ethoxy | H | 283 |
| 14 | pyridin-2-yl | phenoxy | H | 331 |
| 15 | phenyl | Me | Me | 266 |

Preparation 16:
2-Bromo-6-nitro-4-phenoxy-phenylamine

2-Nitro-4-phenoxy-phenylamine (2.3 g, 10 mmol) prepared in Preparation 1 was dissolved in DCM (30 mL), $Br_2$ (720 ul, 35%) was added thereto at 0° C., and the mixture was stirred for 2 h. After completion of the reaction, saturated aqueous sodium thiosulfate solution was added. The resulting mixture was extracted with EtOAc, and dried over $MgSO_4$. The solvent was removed under reduced pressure, and the residue was purified by column chromatography to give the title compound (2.84 g, Yield 92%).

Mass [M+H]=309

Preparation 17:
2-Amino-5-methyl-3-nitro-phenyliodide

Commercially available 4-methyl-2-nitro-phenylamine (20 g, 131.5 mmol) was dissolved in ethanol (300 mL), silver nitrate (27 g, 157.7 mmol) and iodine (40 g, 157.7 mmol) were added thereto, and the mixture was stirred for 8 h at room temperature. After completion of the reaction, the reaction mixture was filtered through a cellite, washed with 100 mL of ethyl acetate, and concentrated. Water was added to the residue, which was then extracted with ethyl acetate, washed with saturated sodium chloride solution, and dried over anhydrous magnesium sulfate to give the title compound (29 g, Yield 69%).

$^1$H-NM (500 MHz, $CDCl_3$); δ 7.94 (s, 1H), 7.75 (s, 1H), 6.48 (br s, 2H), 2.23 (s, 3H)

Preparations 18 to 22

Commercially available nitroanilines and the compounds prepared in Preparations 1 to 7 were reacted according to the same procedure as Preparation 17 to synthesize the Preparation Compounds in the following table.

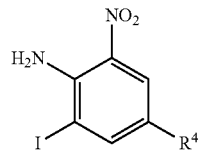

| Preparation | R⁴ | Mass [M + 1] |
| --- | --- | --- |
| 18 | H | 264 |
| 19 | Cl | 298 |
| 20 | CO₂Et | 336 |
| 21 | F | 282 |
| 22 | CH₂CO₂Et | 350 |

Preparation 23: p-(BOC-amino)-phenyl-acetylene p-Aminophenyl-acetylene (1.17 g, 10 mmol) was added to DCM (30 mL), and Et₃N (2.8 mL, 20 mmol) was added thereto. (BOC)₂O (2.3 g, 10 mmol) was added, and the mixture was stirred for 2 h at room temperature. After completion of the reaction, 1N HCl was added, which was then extracted with EtOAc and dried over anhydrous magnesium sulfate. After filtration, the solvent was removed under reduced pressure, and the residue was purified by column chromatography to give the title compound.
Mass [M+H]=117

Preparation 24:
5-Methyl-7-nitro-2-phenyl-1H-indole

Step A:
4-Methyl-2-nitro-6-(phenylacetylene)-phenylamine

2-Amino-5-methyl-3-nitro-phenyliodide (7 g, 25.2 mmol) prepared in Preparation 17 and phenylacetylene (3.3 mL, 30.22 mmol) were dissolved in tetrahydrofuran (100 mL). Triethylamine (11 mL, 75.5 mmol), dichloro(bistriphenylphosphine)palladium (II) (1.8 g, 2.52 mmol) and cupper (I) iodide (0.48 g, 2.52 mmol) were added thereto, and the mixture was stirred for 8 h at room temperature. After completion of the reaction, the reaction mixture was diluted with water, extracted with ethyl acetate, washed with saturated aqueous sodium chloride solution, dried over anhydrous magnesium sulfate, and filtered. The solvent was removed under reduced pressure, and the residue was purified by column chromatography to give the title compound (4.5 g, Yield 71%).
¹H-NMR (400 HMz, CDCl₃); δ 7.93 (s, 1H), 7.53 (m, 2H), 7.46 (s, 1H), 7.39 (m, 3H), 6.62 (br s, 2H), 2.26 (s, 3H)

Step B: 5-Methyl-7-nitro-2-phenyl-1H-indole

4-Methyl-2-nitro-6-(phenylacetylene)-phenylamine (4.5 g, 17.8 mmol) prepared in Step A was dissolved in tetrahydrofuran (120 mL) and N-methyl-pyrrolidinone (30 mL). Potassium t-butoxide (4 g, 35.7 mmol) was added, and the mixture was stirred for 3 h at room temperature. After completion of the reaction, the reaction mixture was diluted with water, extracted with ethyl acetate, washed with saturated aqueous sodium chloride solution, dried over anhydrous magnesium sulfate, and filtered. The solvent was removed under reduced pressure, and the residue was purified by column chromatography to give the title compound (1.0 g, Yield 22%).
¹H-NMR (400 HMz, CDCl₃); δ 11.53 (br s, 1H), 8.02 (d, J=7.6 Hz, 1H), 7.94 (s, 1H), 7.87 (s, 1H), 7.50 (m, 2H), 7.41 (m, 1H), 7.09 (m, J=2.0 Hz, 1H), 2.49 (s, 3H)

Preparations 25 to 40

The compounds prepared in Preparations 16, 18 to 22, commercially available acetylene compounds, and the compound prepared in Preparation 23 were reacted according to the same procedure as Preparation 24 to synthesize the Preparation Compounds in the following table.

| Preparation | R²—A | R⁴ | Mass [M + 1] |
| --- | --- | --- | --- |
| 25 | Ph— | F | 256 |
| 26 | Ph— | Cl | 272 |
| 27 | Ph— | OPh | 330 |
| 28 | Ph— | CO₂H | 282 |
| 29 | Ph— | CH₂CO₂H | 296 |
| 30 | p-HO₂C—Ph— | Me | 296 |
| 31 | p-HO₂C—Ph— | Cl | 316 |
| 32 | m-HO₂C—Ph— | Cl | 316 |
| 33 | o-HO₂C—Ph— | Cl | 316 |
| 34 | p-HO₂CCH₂—Ph— | Cl | 330 |
| 35 | m-HO₂CCH₂—Ph— | Cl | 330 |
| 36 | p-MeO—Ph— | Cl | 302 |
| 37 | m-F—Ph— | CO₂H | 300 |
| 38 | p-MeO—Ph— | CO₂H | 312 |
| 39 | BOC—NH—Ph— | Cl | 287 |
| 40 | BOC—NH—Ph— | CO₂H | 297 |

Preparation 41: 5-Chloro-3-phenyl-7-nitro-1H-indole

Step A: 5-Chloro-7-nitro-3-phenyl-2-trimethylsilyl-1H-indole

2-Amino-5-chloro-3-nitro-phenyliodide (1.5 g, 4.90 mmol) prepared in Preparation 19 and 1-phenyl-2-trimethylsilylacetylene (4.3 g, 24.50 mmol) were dissolved in DMF (50 mL). Palladium acetate (0.11 g, 0.5 mmol), lithium chloride (0.21 g, 4.90 mmol) and triethylamine (2.48 g, 24.50 mmol) were added thereto, and the mixture was stirred under heating for 3 h to 100□. After completion of the reaction, water was added to the reaction mixture, which was then extracted with ethyl acetate, washed with saturated aqueous sodium chloride solution, dried over anhydrous magnesium sulfate, and filtered. The solvent was removed under reduced pressure, and the residue was purified by column chromatography to give the title compound (1.05 g, Yield 87%).
¹H-NMR (400 HMz, CDCl₃); δ 9.78 (br s, 1H), 8.15 (s, 1H), 7.78 (s, 1H), 7.38~7.48 (m, 5H), 0.26 (s, 9H)

Step B: 5-Chloro-3-phenyl-7-nitro-1H-indole

5-Chloro-7-nitro-3-phenyl-2-trimethylsilyl-1H-indole (1.5 g, 4.35 mmol) prepared in Step A was dissolved in tetrahydrofuran (30 mL), and tetrabutylammonium fluoride 1M solution (5.2 mL, 5.2 mmol) was added in drops thereto at 0° C. After completion of the reaction, the reaction mixture was diluted with water, extracted with ethyl acetate, washed with saturated aqueous sodium chloride solution, dried over anhydrous magnesium sulfate, and filtered. The solvent was removed under reduced pressure, and the residue was purified by column chromatography to give the title compound (1.2 g, Yield 100%).

$^1$H-NMR (400 HMz, CDCl$_3$); δ 10.03 (br s, 1H), 8.24 (d, J=8 Hz, 2H), 7.62 (m, 3H), 7.55 (m, 2H), 7.43 (m, 1H)

Preparation 42:
[3-Phenyl-7-nitro-1H-indol-5-yl]-carboxylic acid

3-Iodo-4-amino-5-nitro-1-benzoic acid ethyl ester prepared in Preparation 20 was reacted according to the same procedure as Steps A and B of Preparation 41 to give the title compound.

$^1$H-NMR (400 HMz, CDCl$_3$); δ 9.94 (br s, 1H), 8.86 (s, 1H), 8.52 (s, 1H), 7.48 (m, 5H), 4.42 (q, 2H), 1.43 (t, 3H), 0.27 (s, 9H)

Preparation 43: 5-Chloro-7-nitro-3-(2-oxo-piperazin-4-yl)methyl-2-phenyl-1H-indole Step A:
5-Chloro-3-formyl-7-nitro-2-phenyl-1H-indole 7-Nitro-5-chloro-2-phenyl-1H-indole (1.0 g, 3.67 mmol) prepared in Preparation 26 was dissolved in dichloromethane (20 mL). Phosphoryloxychloride (0.84 g, 5.50 mmol) and DMF (0.80 g, 11.01 mmol) were added in drops thereto at 0° C., and the mixture was stirred for 6 h at room temperature. After completion of the reaction, the reaction was quenched by saturated aqueous sodium hydrogen carbonate solution. The reaction mixture was extracted with ethyl acetate, washed with saturated aqueous sodium chloride solution, dried over anhydrous magnesium sulfate, and filtered. The solvent was removed under reduced pressure, and the residue was purified by column chromatography to give the title compound (0.5 g, Yield 45%).

$^1$H-NMR (400 HMz, DMSO-d$_6$); δ 9.89 (s, 1H), 8.46 (s, 1H), 7.93 (s, 1H), 7.81 (d, J=9.2 Hz, 2H), 7.53 (m, 3H)

Step B: 5-Chloro-7-nitro-3-(2-oxo-piperazin-4-yl)methyl-2-phenyl-1H-indole

5-Chloro-3-formyl-7-nitro-2-phenyl-1H-indole (0.5 g, 1.66 mmol) prepared in Step A was dissolved in dichloroethane (20 mL). Acetic acid (0.10 g, 1.66 mmol), 2-oxopiperazine (0.3 g, 3.32 mmol) and sodium triacetoxyborohydride (0.71 g, 3.32 mmol) were added in drops thereto, and the mixture was stirred for 4 h at room temperature. After completion of the reaction, the reaction mixture was diluted with water, extracted with dichloromethane, washed with saturated aqueous sodium chloride solution, dried over anhydrous magnesium sulfate, and filtered. The solvent was removed under reduced pressure, and the residue was purified by column chromatography to give the title compound (0.55 g, Yield 86%).

$^1$H-NMR (400 HMz, DMSO-d$_6$); δ 9.89 (s, 1H), 8.46 (s, 1H), 7.93 (s, 1H), 7.81 (d, J=9.2 Hz, 2H), 7.53 (m, 3H)

Preparation 44: 5-Chloro-3-(morpholin-4-yl)methyl-7-nitro-2-phenyl-1H-indole

5-Chloro-3-formyl-7-nitro-2-phenyl-1H-indole prepared in Step A of Preparation 43 and morpholine were reacted according to the same procedure as Step B of Preparation 43 to give the title compound.

$^1$H-NMR (400 HMz, CDCl$_3$); δ 9.86 (br s, 1H), 8.23 (s, 1H), 8.14 (s, 1H), 7.77 (d, J=12 Hz, 2H), 7.47~7.56 (m, 3H), 3.70 (m, 4H+2H), 2.49 (m, 4H)

Preparation 45: 5-Methyl-7-nitro-1H-indazole

Step A: 4,6-Dimethyl-2-nitro-phenylamine 2,4-Dimethylaniline (8.0 g, 66.0 mmol) was dissolved in acetic anhydride (50 mL), and nitric acid (5 mL) was slowly added in drops thereto at 0° C. After stirring for 30 min, the mixture was diluted with ice water (200 mL). Conc. hydrochloric acid (10 mL) was added in drops thereto, and the resulting mixture was stirred under reflux for 4 h. After the reaction mixture was cooled to room temperature, the solvent was removed under reduced pressure. The residue was diluted with aqueous ammonium hydroxide solution. The resulting orange solid was filtered and dried to give the title compound (10.6 g, Yield 97%).

Step B: 5-Methyl-7-nitro-1H-indazole 4,6-Dimethyl-2-nitro-phenylamine (10.6 g, 64.08 mmol) prepared in Step A was dissolved in acetic acid (150 mL). Sodium nitrite (5.3 g, 76.90 mmol) was added in drops thereto, and the mixture was stirred for 12 h. After completion of the reaction, the reaction mixture was diluted with ammonium hydroxide, extracted with dichloromethane, washed with saturated aqueous sodium chloride solution, dried over anhydrous magnesium sulfate, and filtered. The solvent was removed under reduced pressure, and the residue was purified by column chromatography to give the title compound (1.0 g, Yield 9%).

$^1$H-NMR (400 HMz, CDCl$_3$); δ 11.29 (br s, 1H), 8.18 (d, J=8 Hz, 2H), 7.93 (s, 1H), 2.58 (s, 3H)

Preparation 46: 3-(4-Methoxy-phenyl-1-yl)-7-nitro-1H-indazole

Step A: 3-Iodo-7-nitro-1H-indazole

7-Nitroindazole (1.60 g, 9.80 mmol) was dissolved in DMF (100 mL), and potassium hydroxide (2.20 g, 39.20 mmol) and iodine (4.98 g, 19.61 mmol) were added in drops thereto. After stirring for 2 h, the reaction mixture was diluted with 10% aqueous sodium bisulfite solution. The resulting solid was collected and dried to give the title compound (2.50 g, Yield 88%).

$^1$H-NMR (400 HMz, CDCl$_3$); δ 11.49 (br s, 1H), 8.45 (d, J=8 Hz, 1H), 7.94 (d, J=8 Hz, 1H), 7.41 (t, 1H)

Step B:
3-Iodo-7-nitro-1-(4-methoxybenzyl)-1H-indazole

3-Iodo-7-nitro-1H-indazole (2.50 g, 8.65 mmol) prepared in Step A was dissolved in acetone (50 mL). Potassium hydroxide (0.73 g, 12.97 mmol) and 4-methoxybenzylchloride (1.63 g, 10.38 mmol) were added in drops thereto at 0° C., and the mixture was stirred for 2 h. After completion of the reaction, the reaction mixture was diluted with water, extracted with ethyl acetate, washed with saturated aqueous sodium chloride solution, dried over anhydrous magnesium sulfate, and filtered. The solvent was removed under reduced pressure, and the residue was purified by column chromatography to give the title compound (3.2 g, Yield 91%).

¹H-NMR (400 HMz, CDCl₃); δ 8.08 (d, J=8 Hz, 1H), 7.83 (d, J=8 Hz, 1H), 7.28 (m, 1H), 6.97 (d, J=8 Hz, 1H), 6.75 (d, J=8 Hz, 1H), 5.83 (s, 2H), 3.72 (s, 3H)

Step C: 3-(4-Methoxy-phenyl-1-yl)-7-nitro-1H-indazole

3-Iodo-7-nitro-1-(4-methoxybenzyl)-1H-indazole (1.50 g, 3.67 mmol) prepared in Step B was dissolved in dimethoxyethane (20 mL). Sodium carbonate (1.17 g, 11.01 mmol), 4-methoxyphenylboronic acid (0.84 g, 5.50 mmol) and tetrakis(triphenylphosphine)palladium (0) (0.43 g, 0.37 mmol) were added in drops thereto, and the mixture was stirred under reflux for 2 h. After the reaction solution was cooled, it was diluted with water, extracted with ethyl acetate, washed with saturated aqueous sodium chloride solution, dried over anhydrous magnesium sulfate, and filtered. The solvent was removed under reduced pressure, and the residue was dissolved in trifluoroacetic acid (20 mL). After the mixture was stirred under reflux for 5 h, the solvent was removed under reduced pressure. The residue was diluted with water, extracted with ethyl acetate, washed with saturated aqueous sodium chloride solution, dried over anhydrous magnesium sulfate, and filtered. The solvent was removed under reduced pressure, and the residue was purified by column chromatography to give the title compound (0.85 g, Yield 86%).

¹H-NMR (400 HMz, CDCl₃); δ 11.33 (br s, 1H), 8.39 (t, 2H), 7.90 (d, J=8 Hz, 2H), 7.36 (t, 1H), 7.08 (d, J=8 Hz, 2H), 3.91 (s, 3H)

Preparation 47: 4-[(3-Bromo-7-nitro-2-phenyl-1H-indol-5-yl)methyl]-piperazin-2-one

Step A: 1-BOC-5-methyl-7-nitro-2-phenyl-indole

5-Methyl-7-nitro-2-phenyl-1H-indole prepared in Preparation 24, (BOC)₂O and DMAP were reacted according to the same procedure as Preparation 23 to give the title compound.

Step B: 1-BOC-3-bromo-5-bromomethyl-7-nitro-2-phenyl-indole

1-BOC-5-methyl-7-nitro-2-phenyl-indole (3.5 g, 10 mmol) prepared in Step A was dissolved in carbon tetrachloride (30 mL). N-bromosuccinimide (NBS, 2.3 g, 13 mmol) and benzoyl peroxide (100 mg) were added thereto, and the mixture was stirred under reflux for 4 h at 80° C. After filtration, the solid moiety was removed. Water was added, and the mixture was extracted with DCM. The solvent was removed under reduced pressure, and the residue was purified by column chromatography to give the title compound (2.3 g, Yield 46%).

Step C: 4-[(1-BOC-3-bromo-7-nitro-2-phenyl-1H-indol-5-yl)methyl]-piperazin-2-one 1-BOC-3-bromo-5-bromomethyl-7-nitro-2-phenyl-indole prepared in Step B (1.0 g, 2 mmol) was dissolved in DCM (10 mL). Et₃N (560 uL, 4 mmol) was added, 2-oxo-piperazine (300 mg, 3 mmol) was added, and the mixture was stirred for 12 h at room temperature. After completion of the reaction, saturated aqueous NH₄Cl solution was added, and the reaction mixture was extracted with DCM. After drying, the solvent was removed under reduced pressure. The residue was purified by column chromatography to give the title compound (825 mg, Yield 78%).

Step D: [(3-Bromo-7-nitro-2-phenyl-1H-indol-5-yl)methyl]-piperazin-2-one

4-[(1-BOC-3-bromo-7-nitro-2-phenyl-1H-indol-5-yl)methyl]-piperazin-2-one (825 mg, 1.6 mmol) prepared in Step C was dissolved in diethylester (5 mL). HCl (4 M dioxane solution, 5 mL) was added, and the mixture was stirred for 2 h at room temperature. After completion of the reaction, the solvent was removed under reduced pressure. The residue was dried, and used in the next reaction.

Mass [M+H]=429

Preparation 48: 4-[(3-Bromo-7-nitro-2-phenyl-1H-indol-5-yl)methyl]-morpholine 1-BOC-3-bromo-5-bromomethyl-7-nitro-2-phenyl-indole prepared in Step B of Preparation 47 and morpholine were reacted according to the same procedures as Steps C and D of Preparation 47 to give the title compound.

Mass [M+H]=416

EXAMPLE 1

Cyclopentyl-[5-methyl-2-(pyridin-2-yl)-1H-indol-7-yl]-amine

Step A: 7-Amino-5-methyl-2-(pyridin-2-yl)-1H-indole

5-Methyl-7-nitro-2-(pyridin-2-yl)-1H-indole (6.9 g, 27.3 mmol) prepared in Preparation 8 was dissolved in a solvent mixture of tetrahydrofuran (130 mL), methanol (1 mL) and water (130 mL), and NH₄Cl (14.6 g, 27.3 mmol) was added thereto. The reaction mixture was warmed to 60° C., iron powder (15.2 g, 273 mmol) was added thereto, and the mixture was stirred for 30 min. After completion of the reaction, the reaction mixture was filtered through a cellite to remove the solid. Certain amount of the solvent was removed under reduced pressure from the resulting solution, which was then extracted with EtOAc. The extracted organic material was dried over MgSO₄, and the solvent was removed under reduced pressure to give the title compound (5.0 g, Yield 40%).

Step B: Cyclopentyl-[5-methyl-2-(pyridin-2-yl)-1H-indol-7-yl]amine

7-Amino-5-methyl-2-(pyridin-2-yl)-1H-indole (5 g, 22.4 mmol) prepared in Step A and cyclopentanone (1.88 g, 22.4 mmol) were added to dichloroethane (50 mL). NaBH(OAc)₃ (9.5 g, 44.8 mmol) was added thereto, and the mixture was stirred for 12 h at room temperature. After completion of the reaction, the reaction mixture was diluted with saturated aqueous NaHCO₃ solution, and extracted with dichloromethane and EtOAc. The extracted organic material was washed with water and aqueous NaCl solution, and dried over MgSO₄. The solvent was removed under reduced pressure, and the residue was purified by column chromatography (eluent EtOAc/n-Hex=1/5) to give the title compound (3.77 g, Yield 58%).

¹H-NMR (400 HMz, CDCl₃); δ 9.73 (br s, 1H), 8.53 (d, J=4.8 Hz, 1H), 7.78 (d, J=8.0 Hz, 1H), 7.70 (m, 1H), 7.13 (m, 1H), 6.91 (d, J=2.0 Hz, 1H), 6.87 (s, 1H), 6.32 (s, 1H), 3.91 (m, 1H), 3.60 (br s, 1H), 2.41 (s, 3H), 2.00 (m, 2H), 1.65 (m, 4H), 1.51 (m, 2H)

EXAMPLE 2

Cyclopentyl-[5-methyl-2-phenyl-1H-indol-7-yl]amine

5-Methyl-7-nitro-2-phenyl-1H-indole prepared in Preparation 24 was reacted according to the same procedures as Steps A and B of Example 1 to give the title compound.

$^1$H-NMR (500 MHz, DMSO-$d_6$); δ 10.91 (brs, 1H), 7.75 (m, 2H), 7.65 (m, 1H), 7.41 (m, 2H), 7.26 (m, 1H), 6.64 (s, 1H), 6.53 (s, 1H), 6.02 (s, 1H), 5.20 (m, 1H), 3.57 (m, 2H), 3.51 (m, 5H), 3.14 (m, 2H), 2.29 (m, 4H), 2.24 (s, 3H), 1.87 (m, 2H), 1.78 (m, 2H), 1.68 (m, 2H), 1.53 (m, 2H)

EXAMPLE 3

[5-Chloro-2-phenyl-1H-indol-7-yl]amine

5-Chloro-7-nitro-2-phenyl-1H-indole prepared in Preparation 26 was reacted according to the same procedure as Step A of Example 1 to give the title compound.

$^1$H-NMR (500 MHz, DMSO-$d_6$); δ 10.96 (brs, 1H), 7.76 (d, 2H), 7.46 (t, 2H), 7.30 (t, 1H), 6.75 (s, 1H), 6.72 (s, 1H), 6.19 (s, 1H), 5.13 (s, 2H)

EXAMPLE 4

(Tetrahydropyran-4-yl)-[5-methyl-2-(pyridin-2-yl)-1H-indol-7-yl]-amine

7-Amino-5-methyl-2-(pyridin-2-yl)-1H-indole prepared in Step A of Example 1 and 4-oxo-tetrahydropyran were reacted according to the same procedure as Step B of Example 1 to give the title compound (25 mg, Yield 36%).

$^1$H-NMR (400 HMz, CDCl$_3$); δ 10.65 (br s, 1H), 8.49 (d, J=4.8 Hz, 1H), 7.81 (d, J=8.0 Hz, 1H) 7.72 (m, 1H), 7.13 (m, 1H), 6.92 (d, J=2.0 Hz, 1H), 6.88 (s, 1H), 6.27 (s, 1H), 3.92 (m, 1H), 3.49 (m, 3H), 2.39 (s, 3H), 1.95 (m, 2H), 1.30 (m, 2H)

EXAMPLES 5 to 19

The compounds prepared in Preparations 8 to 15 and commercially available ketone or aldehyde were reacted according to the same procedure as Example 1 to synthesize the Example Compounds in the following table.

| Example | R$^1$ | L | R$^2$ | R$^4$ | R$^5$ | R$^6$ |
|---|---|---|---|---|---|---|
| | | | H$^1$ NMR | | | |
| 5 | H | N | H | H | H | c-Pen |
| | (400 MHz, CDCl$_3$); δ 9.72 (br s, 1H), 9.08 (d, 1H), 8.40 (m, 1H), 8.37 (m, 1H), 7.12 (m, 2H), 7.03 (t, 1H), 6.56 (d, 1H), 4.94 (m, 1H), 2.02 (m, 2H), 1.77~1.48 (m, 6H) | | | | | |
| 6 | H | N | H | Me | H | c-Pen |
| | (400 MHz, CDCl$_3$); δ 9.55 (br s, 1H), 9.06 (s, 1H), 8.41 (d, J = 4.0 Hz, 1H), 8.26 (s, 1H), 7.03 (s, 1H), 6.90 (s, 1H), 6.38 (s, 1H), 3.95 (m, 1H), 2.41 (s, 3H), 2.06 (m, 2H) 1.71~1.49 (m, 6H) | | | | | |
| 7 | H | C | H | H | H | c-Pen |
| | (400 MHz, CDCl$_3$); δ 8.48 (m, 1H), 7.81 (d, 1H), 7.72 (m, 1H), 7.12 (m, 1H), 7.08 (d, 1H), 7.01 (s, 1H), 6.97 (t, 1H), 6.44 (d, 1H), 3.81 (m, 1H), 1.89 (m, 2H), 1.50 (m, 4H), 1.27 (m, 2H) | | | | | |
| 8 | H | C | H | H | H | THP |
| | (400 MHz, MeOH-$d_4$/CDCl$_3$); δ 10.91 (br s, 1H), 8.51 (m, 1H), 7.85 (d, 1H), 7.75 (m, 1H), 7.16 (m, 1H), 7.09 (d, 1H), 7.02 (d, 1H), 6.98 (t, 1H), 6.42 (d, 1H), 3.89 (m, 2H) 3.52 (m, 1H), 3.44 (m, 2H), 1.89 (m, 2H), 1.88 (m, 2H_ | | | | | |
| 9 | H | C | H | OPh | H | c-Pen |
| | (400 MHz, CDCl$_3$); δ 10.07 (br s, 1H), 8.55 (d, J = 4.0 Hz, 1H), 7.74 (m, 2H), 7.29 (m, 2H), 7.18 (m, 1H), 7.01 (m, 3H), 6.93 (d, J = 4.0 Hz, 1H), 6.69 (d, J = 4.0 Hz, 1H), 6.27 (s, 1H), 3.81 (m, 1H), 3.70 (br s, 1H), 1.96 (m, 2H), 1.60 (m, 4H), 1.41 (m, 2H) | | | | | |
| 10 | H | C | H | OEt | H | c-Pen |
| | (400 MHz, CDCl$_3$); δ 9.86 (br s, 1H), 8.56 (d, J = 4.8 Hz, 1H), 7.81 (d, J = 8.0 Hz, 1H), 7.74 (m, 1H), 7.17 (m, 1H), 6.94 (d, J = 2.0 Hz, 1H), 6.54 (d, J = 2.0 Hz, 1H), 6.22 (d, J = 2.oHz, 1H), 4.11 (q, 2H), 3.91(m, 1H), 2.05 (m, 2H), 1.76~1.63 (m, 4H), 1.54~1.46 (m, 5H) | | | | | |
| 11 | H | C | H | Me | H | c-Hex |
| | (500 MHz, CDCl$_3$); δ 10.46 (br s, 1H), 8.48 (d, J = 4.9 Hz, 1H), 7.79 (d, J = 8.0 Hz, 1H), 7.70 (m, 1H), 7.11 (m, 1H), 6.92 (d, J = 1.8 Hz, 1H), 6.85 (s, 1H), 3.30 (m, 1H), 2.39 (s, 3H), 1.98 (m, 2H), 1.70 (m, 2H), 1.60 (m, 1H), 1.31 (m, 2H), 1.39 (m, 2H), 0.95 (m, 1H) | | | | | |
| 12 | H | C | H | Me | H | 1-acetyl-piperidin-4-yl |
| | (500 MHz, CDCl$_3$ & MeOH-$d_4$); δ 8.42 (d, J = 4.9 Hz, 1H), 7.71(d, J = 8.0 Hz, 1H), 7.65 (m, 1H), 7.08 (m, 1H), 6.83 (s, 1H), 6.78 (s, 1H), 6.22 (s, 1H), 4.33 (m, 1H), 3.77 (m, 1H), 3.60 (m, 1H), 3.52 (s, 3H), 3.17 (m, 1H), 2.91 (m, 1H), 2.31 (s, 3H), 2.13 (m, 1H), 2.06 (m, 1H), 1.39 (m, 2H) | | | | | |
| 13 | H | C | H | Me | H | 4-Me-piperidin-4-yl |
| | (400 MHz, CDCl$_3$); δ 10.75(br s, 1H), 8.45 (d, J = 4.8 Hz, 1H), 7.77 (d, J = 8.0 Hz, 1H), 7.68 (m, 1H), 7.08 (m, 1H), 6.90 (d, J = 2.0 Hz, 1H), 6.85 (s, 1H), 6.24 (s, 1H), 3.30 (m, 1H), 2.73 (m, 2H), 2.38 (s, 3H), 2.24 (s, 3H), 2.08 (m, 2H), 1.97 (m, 2H), 1.33 (m, 2H) | | | | | |

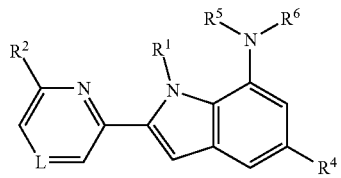

| Example | R¹ | L | R² | R⁴ | R⁵ | R⁶ |
|---------|----|----|----|----|----|-----|
| | | | | H¹ NMR | | |
| 14 | H | C | H | Me | H | 1-benzyl-pyrrolidin-3-yl |
| | (400 MHz, CDCl₃); δ 10.72 (br s, 1H), 8.49 (m, 1H), 7.76 (d, J = 8.0 Hz, 1H), 7.66 (m, 1H), 7.31~7.21 (m, 5H), 7.08 (m. 1H), 6.89 (d, J = 2.0 Hz, 1H), 6.83 (s, 1H), 6.22 (s, 1H), 4.09 (br s, 1H), 3.61 (m, 2H), 2.79 (m, 1H), 2.64 (m, 1H), 2.44 (m, 2H), 2.38 (s, 3H), 2.25 (m, 1H), 1.61 (m, 1H) | | | | | |
| 15 | H | C | H | Me | H | (c-Pen)methyl |
| | (500 MHz, CDCl₃); δ 10.54 (br s, 1H), 8.48 (m, 1H), 7.79 (d, J = 8.0 Hz, 1H), 7.71 (m, 1H), 7.12 (m, 1H), 6.93 (d, J = 2.5 Hz, 1H), 6.88 (s, 1H), 6.28 (s, 1H), 3.07 (d, J = 7.3 Hz, 1H), 2.41 (s, 3H), 2.05 (m, 1H), 1.69~1.51 (m, 6H), 1.19(m, 2H) | | | | | |
| 16 | H | C | H | Me | —(CH₂)₅— | |
| | ¹H-NMR (500 MHz, CDCl₃); δ 9.44 (br s, 1H), 8.59 (d, 1H), 7.76 (d, 1H), 7.68 (t, 1H), 7.14 (m, 2H), 6.93 (d, 1H), 6.68 (s, 1H), 3.11 (m, 4H), 2.44 (s, 3H), 1.84 (m, 4H) 1.64 (m, 2H) | | | | | |
| 17 | H | C | H | Me | Me | Me |
| | (400 MHz, CDCl₃); δ 8.48 (d, 2H), 7.55 (m, 1H), 7.45 (d, 1H), 7.04 (m, 1H), 6.65 (s, 1H), 6.61 (d, 1H(, 2.90 (s, 6H), 2.34 (s, 3H) | | | | | |
| 18 | Me | C | H | Me | H | c-Pen |
| | (400 MHz, CDCl₃); δ 8.67 (m, 1H), 7.72 (m, 1H), 7.66 (m, 1H), 7.19 (m, 1H), 6.86 (s, 1H), 6.67 (s, 1H), 6.35 (s, 1H), 4.12 (s, 3H), 3.90 (m, 1H), 3.83 (br s, 1H), 2.389s, 3H), 2.05 (m, 2H), 1.80~1.55 (m, 6H) | | | | | |
| 19 | H | C | Me | Me | H | c-Pen |
| | (400 MHz, CDCl₃); δ 11.26 (br s, 1H), 7.59 (m, 2H), 6.94 (m, 1H), 6.89 (d, 1H), 6.82 (s, 1H), 6.19 (s, 1H), 3.73 (m, 1H), 2.37 (s, 3H), 2.31 (s, 3H), 1.80 (m, 2H), 1.42 (m, 4H), 1.45 (m, 2H) | | | | | |

EXAMPLE 20

(1-Cyclohexanon-4-yl)-[5-methyl-2-(pyridin-2-yl)-1H-indol-7-yl]-amine

Step A: (1,4-Dioxa-[4.5]dec-8-yl)-[5-methyl-2-(pyridin-2-yl)-1H-indol-7-yl)amine 7-Amino-5-methyl-2-(pyridin-2-yl)-1H-indole prepared in Step A of Example 1 and 1,4-cyclohexanedione monoethylene acetal were reacted according to the same procedure as Step B of Example 1 to give the title compound.

Step B: (1-Cyclohexanon-4-yl)-[5-methyl-2-(pyridin-2-yl)-1H-indol-7-yl]-amine (1,4-Dioxa-[4.5]dec-8-yl)-[5-methyl-2-(pyridin-2-yl)-1H-indol-7-yl)amine (30 mg, 0.13 mmol) prepared in Step A was dissolved in acetone (10 mL) and water (5 mL). 1N hydrochloric acid solution (1 mL) was added thereto, and the mixture was stirred for 8 h at 80° C. After completion of the reaction, saturated aqueous NaHCO₃ solution was added. The reaction mixture was extracted with EtOAc, and dried over anhydrous MgSO₄. The solvent was removed under reduced pressure, and the residue was purified by column chromatography (eluent EtOAc/n-Hex=1/5) to give the title compound (10 mg, Yield 23%).

¹H-NMR (400 HMz, CDCl₃); δ 10.72 (br s, 1H), 8.48 (d, J=4.4 Hz, 1H), 7.81 (d, J=8.0 Hz, 1H), 7.73 (m, 1H), 7.13 (m, 1H), 6.92 (d, J=2.0 Hz, 1H), 6.91 (s, 1H), 6.32 (s, 1H), 3.78 (m, 1H) 2.41 (s, 3H), 2.35 (m, 4H), 2.20 (m, 2H), 1.52 (m, 2H)

EXAMPLE 21

4-[(5-Chloro-2-phenyl-1H-indol-7-yl)amino]-cyclohexan-1-one

7-Amino-5-chloro-2-phenyl-1H-indole prepared in Example 3 was reacted according to the same procedure as Example 20 to give the title compound.

¹H-NMR (500 MHz, DMSO-d₆); δ 11.09 (s, 1H), 7.76 (d, J=6.7 Hz, 2H), 7.45 (t, J=7.3 Hz, 2H), 7.30 (t, J=7.3 Hz, 1H), 6.79 (d J=1.25 Hz, 1H), 6.74 (d, J=1.8 Hz, 1H), 6.32 (d, J=1.85 Hz, 1H), 5.66 (m, 1H), 3.92 (m, 1H), 2.55 (m, 2H), 2.38-2.21 (m, 4H), 1.72 (m, 2H)

EXAMPLE 22

N-(5-methyl-2-(pyridin-2-yl)-1H-indol-7-yl)-benzamide

7-Amino-5-methyl-2-(pyridin-2-yl)-1H-indole (45 mg, 0.20 mmol) prepared in Step A of Example 1 was dissolved in dichloromethane (10 mL). Et₃N (0.56 mL, 0.4 mmol) and benzoyl chloride (0.03 mL, 0.22 mmol) were added thereto, and the mixture was stirred for 2 h at room temperature. After completion of the reaction, the reaction mixture was diluted with water, extracted with EtOAc, and dried over anhydrous MgSO₄. The solvent was removed under reduced pressure, and the residue was purified by column chromatography (eluent EtOAc/n-Hex=1/5) to give the title compound (18 mg, Yield 27%).

¹H-NMR (500 HMz, CDCl₃); δ 10.98 (br s, 1H), 8.61 (s, 1H), 8.50 (d, J=4.9 Hz, 1H), 7.90 (d, J=7.4 Hz, 2H), 7.77 (d,

J=8.0 Hz, 1H), 7.69 (m, 1H), 7.50 (m, 1H), 7.43 (m, 2H), 7.31 (s, 1H), 7.26 (s, 1H), 7.14 (m, 1H), 6.95 (d, J=1.8 Hz, 1H), 2.41 (s, 3H)

EXAMPLE 23

1-Ethyl-3-[5-methyl-2-(pyridin-2-yl)-1H-indol-7-yl]-urea

7-Amino-5-methyl-2-(pyridin-2-yl)-1H-indole prepared in Step A of Example 1 and ethylisocyanate were reacted according to the same procedure as Example 22 to give the title compound.
$^1$H-NMR (400 MHz, MeOH-d$_4$); δ 8.53 (d, 1H), 7.77 (d, 1H), 7.72 (m, 1H), 7.21 (s, 1H), 7.17 (m, 1H), 7.02 (s, 1H), 6.95 (s, 1H), 3.27 (q, 2H), 2.41 (s, 3H), 1.14 (t, 3H)

EXAMPLE 24

1-Phenyl-3-[5-methyl-2-(pyridin-2-yl)-1H-indol-7-yl]-urea

7-Amino-5-methyl-2-(pyridin-2-yl)-1H-indole prepared in Step A of Example 1 and phenylisocyanate were reacted according to the same procedure as Example 22 to give the title compound.
$^1$H-NMR (400 MHz, CDCl$_3$/MeOH-d$_4$); δ 8.52 (d, 1H), 7.79 (d, 1H), 7.73 (m, 1H), 7.45 (d, 2H), 7.30 (t, 2H), 7.21 (s, 1H), 7.18 (m, 1H), 7.13 (s, 1H), 7.04 (m, 1H), 6.96 (s, 1H), 2.42 (s, 3H)

EXAMPLE 25

Thiophene-2-sulfonic acid (2-pyridin-2-yl-1H-indol-7-yl)-amide

2-Pyridin-2-yl-7-nitro-1H-indole prepared in Preparation 9 and 2-thiophenesulfonylchloride were reacted according to the same procedures as Step A of Example 1 and Example 22 sequentially to give the title compound.
$^1$H-NMR (400 MHz, CDCl$_3$); δ 10.25 (br s, 1H), 7.71 (d, 1H), 7.66 (m, 1H), 7.60 (br s, 1H), 7.47 (d, 1H), 7.43~7.40 (m, 2H), 7.13 (m, 1H), 6.97 (d, 1H), 6.94~6.86 (m, 2H), 6.74 (d, 1H)

EXAMPLE 26

Thiophene-2-sulfonic acid [5-methyl-2-(pyridin-2-yl)-1H-indol-7-yl]-amide

7-Amino-5-methyl-2-(pyridin-2-yl)-1H-indole prepared in Step A of Example 1 and 2-thiophenesulfonylchloride were reacted according to the same procedure as Example 22 to give the title compound.
$^1$H-NMR (400 MHz, CDCl$_3$); δ 9.13 (br s, 1H), 8.51 (d, 1H), 7.81 (m, 2H), 7.68 (m, 3H), 7.48 (s, 1H), 7.10 (m, 2H), 6.88 (d, 1H), 6.69 (s, 1H), 2.36 (s, 3H)

EXAMPLE 27

Cyclopentyl-methyl-[5-methyl-2-(pyridin-2-yl)-1H-indol-7-yl]-amine

Cyclopentyl-[5-methyl-2-(pyridin-2-yl)-1H-indol-7-yl] amine prepared in Example 1 and formaldehyde were reacted according to the same procedure as Step B of Example 1 to give the title compound.
$^1$H-NMR (400 MHz, CDCl$_3$); δ 9.53 (br s, 1H), 8.63 (d, 1H), 7.80 (m, 1H), 7.73 (m, 1H), 7.79 (m, 2H), 6.96 (s, 1H), 6.81 (s, 1H), 3.73 (m, 1H), 2.84 (s, 3H), 2.47 (s, 3H), 1.91~1.21 (m, 8H)

EXAMPLE 28

7-(Cyclopentyl)amino-2-phenyl-1H-indole-5-carboxylic acid ethyl ester

Step A: 2-Phenyl-7-nitro-1H-indole-5-carboxylic acid ethyl ester

2-Phenyl-7-nitro-1H-indole-5-carboxylic acid (14.1 g, 50 mmol) prepared in Preparation 30 was dissolved in ethanol (40 mL). Conc. sulfuric acid (10 mL) was added thereto, and the mixture was stirred for 2 h at 50° C. After completion of the reaction, 1N NaOH was added to the reaction mixture, which was then extracted with EtOAc, dried over anhydrous magnesium sulfate, and filtered. The solvent was removed under reduced pressure, and the residue was recrystallized from EtOAc and hexane to give the title compound (14.1 g, Yield 95%).

Step B: 7-(Cyclopentyl)amino-2-phenyl-1H-indole-5-carboxylic acid ethyl ester

2-Phenyl-7-nitro-1H-indole-5-carboxylic acid ethyl ester prepared in Step A and cyclopentanone were reacted according to the same procedure as Example 1 to give the title compound.
$^1$H-NMR (400 MHz, CDCl$_3$); δ 9.47 (brs, 1H), 7.90 (s, 1H), 7.67 (m, 2H), 7.34 (m, 2H), 7.24 (m, 1H), 7.18 (s, 1H), 6.83 (s, 1H), 4.41 (q, 2H), 3.87 (m, 1H), 1.95 (m, 2H), 1.62 (m, 2H), 1.49 (m, 4H), 1.39 (t, 3H)

EXAMPLE 29

Cyclopentyl-[5-hydroxymethyl-2-phenyl-1H-indol-7-yl]-amine

Step A:
5-Hydroxymethyl-2-phenyl-7-nitro-1H-indole

2-Phenyl-7-nitro-1H-indole-5-carboxylic acid ethyl ester (10 g, 29 mmol) prepared in Step A of Example 28 was dissolved in methanol (100 mL), and LiBH$_4$ (1M THF solution, 4 mL) was added thereto at 0° C. After warming to room temperature, the mixture was stirred for 3 h. A small amount of water was added to quench the reaction. Methanol was removed under reduced pressure. 1N HCl was added to the residue, which was then extracted with EtOAc, dried, and used in the next reaction without further purification.
Step B: Cyclopentyl-[5-hydroxymethyl-2-phenyl-1H-indol-7-yl]-amine
5-Hydroxymethyl-2-phenyl-7-nitro-1H-indole prepared in Step A was reacted according to the same procedure as Example 1 to give the title compound.
$^1$H-NMR (400 MHz, MeOH-d$_4$); δ 7.88 (s, 1H), 7.75 (m, 2H), 7.42 (m, 2H), 7.30 (m, 1H), 7.16 (s, 1H), 6.85 (s, 1H), 4.03 (m, 1H), 2.13 (m, 2H), 1.77 (m, 2H), 1.66 (m, 4H)

EXAMPLE 30

7-(Cyclopentyl)amino-2-phenyl-1H-indole-5-carboxylic acid 7-(Cyclopentyl)amino-2-phenyl-1H-indole-5-carboxylic acid ethyl ester (5 g, 14.3 mmol) prepared in Example 28 was added to a solvent mixture of MeOH (20 mL) and water (20 mL). NaOH (1.3 g, 33.8 mmol) was added thereto, and the mixture was stirred for 4 h at room temperature. After completion of the reaction, MeOH was removed under reduced pressure, and 1N HCl was added to the residue. The resulting mixture was extracted with EtOAc, dried over anhydrous magnesium sulfate, and filtered. The solvent was removed under reduced pressure, and the residue was recrystallized from EtOAc and n-Hex to give the title compound.

$^1$H-NMR (400 MHz, MeOH-d$_4$); δ 7.88 (s, 1H), 7.75 (m, 2H), 7.42 (m, 2H), 7.30 (m, 1H), 7.16 (s, 1H), 6.85 (s, 1H), 4.03 (m, 1H), 2.13 (m, 2H), 1.77 (m, 2H), 1.66 (m, 4H)

EXAMPLE 31

2-[7-(Cyclopentyl)amino-2-phenyl-1H-indol-5-yl]-acetic acid ethyl ester 2-(2-Phenyl-7-nitro-1H-indol-5-yl)acetic acid prepared in Preparation 29 was reacted according to the same procedure as Example 28 to give the title compound.

$^1$H-NMR (400 MHz, CDCl$_3$); δ 8.12 (brs, 1H), 7.67 (m, 2H), 7.42 (m, 2H), 7.30 (m, 1H), 6.99 (s, 1H), 6.74 (s, 1H), 6.46 (s, 1H), 4.16 (q, 2H), 3.93 (m, 1H), 3.66 (s, 2H), 2.10 (m, 2H), 1.77 (m, 2H), 1.66 (m, 2H), 1.59 (t, 3H), 1.26 (t, 3H)

EXAMPLE 32

2-[7-(Cyclopentylamino)-2-phenyl-1H-indol-5-yl] ethanol

2-[7-(Cyclopentyl)amino-2-phenyl-1H-indol-5-yl]acetic acid ethyl ester prepared in Example 31 and cyclopentanone were reacted according to the same procedure as Example 29 to give the title compound (257 mg, Yield 80%).

$^1$H-NMR (400 MHz, CDCl$_3$+MeOH-d$_4$); δ 7.71 (m, 2H), 7.40 (m, 2H), 7.28 (m, 1H), 6.89 (s, 1H), 6.72 (s, 1H), 6.32 (s, 1H), 3.97 (m, 1H), 3.87 (m, 2H), 3.43 (m, 1H), 2.91 (m, 2H), 2.09 (m, 2H), 1.77 (m, 2H), 1.62 (m, 4H)

EXAMPLE 33

2-[7-(Cyclopentyl)amino-2-phenyl-1H-indol-5-yl] acetic acid

2-[7-(Cyclopentyl)amino-2-phenyl-1H-indol-5-yl]acetic acid ethyl ester prepared in Example 31 was reacted according to the same procedure as Example 30 to give the title compound.

$^1$H-NMR (400 MHz, CDCl$_3$+MeOH-d$_4$); δ 11.31 (s, 1H), 7.81 (m, 2H), 7.37 (m, 2H), 7.25 (m, 1H), 7.05 (s, 1H), 6.65 (s, 1H), 3.89 (m, 1H), 1.88 (m, 7H), 1.41 (m, 3H)

EXAMPLE 34

2-[2-Phenyl-7-(tetrahydropyran-4-yl)amino-1H-indol-5-yl]-acetic acid 2-(2-Phenyl-7-amino-1H-indol-5-yl)-acetic acid ethyl ester prepared as an intermediate in the process of Example 31 and 4-oxo-tetrahydropyran were reacted according to the same procedures as Step B of Example 1 and Example 30 to give the title compound.

$^1$H-NMR (400 MHz, DMSO-d$_6$, Na salt); δ 10.88 (br s, 1H), 7.81 (d, J=8 Hz, 2H), 7.43 (m, 2H), 7.28 (m, 1H), 6.67 (s, 1H), 6.62 (s, 1H), 6.29 (s, 1H), 5.23 (m, 1H), 3.92 (d, J=8 Hz, 2H), 3.67 (m, 1H), 3.47 (m, 2H), 3.14 (s, 2H), 2.06 (m, 2H), 1.48 (m, 2H)

EXAMPLE 35

2-[2-Phenyl-7-(1,1-dioxo-tetrahydro-thiopyran-4-yl) amino-1H-indol-5-yl]-acetic acid 2-(2-Phenyl-7-amino-1H-indol-5-yl)acetic acid ethyl ester prepared as an intermediate in the process of Example 31 and 1,1-dioxo-tetrahydro-thiopyran-4-one were reacted according to the same procedures as Step B of Example 1 and Example 30 to give the title compound.

$^1$H-NMR (400 MHz, DMSO-d$_6$, Na salt); δ 10.90 (s, 1H), 7.80 (d, J=8 Hz, 2H), 7.43 (t, 2H), 7.29 (m, 1H), 6.69 (q, 2H), 6.28 (s, 1H), 5.35 (m, 1H), 3.81 (m, 1H), 3.31 (m, 2H), 3.20 (m, 2H), 3.16 (s, 2H), 2.33 (m, 2H), 2.02 (m, 2H)

EXAMPLE 36

(Tetrahydropyran-4-yl)[2-phenyl-5-(1,1-dioxo-thiomorpholin-4-yl)methyl-1H-indol-7-yl]amine Step A: 5-Iodomethyl-2-phenyl-7-nitro-1H-indole 5-Hydroxymethyl-2-phenyl-7-nitro-1H-indole (804 mg, 3 mmol) prepared in Step A of Example 29 was dissolved in THF (10 mL), and imidazole (408 mg, 6 mmol) and triphenylphosphine (1.52 g, 6 mmol) were added thereto. Iodine (453 mg, 3.9 mmol) was added to the mixture, which was then stirred for 2 h. After completion of the reaction, the reaction mixture was filtered through a cellite, and the product was used in the next reaction without further purification.

Step B: 5-(1,1-Dioxo-thiomorpholin-4-yl)methyl-2-phenyl-7-nitro-1H-indole

5-Iodomethyl-2-phenyl-7-nitro-1H-indole (850 mg, 2.5 mmol) prepared in Step A was dissolved in THF (10 mL). 1,1-Dioxo-thiomorpholine (405 mg, 2.25 mmol) was added thereto, and the mixture was stirred for 2 h. After completion of the reaction, the reaction mixture was diluted with water, extracted with EtOAc, dried over anhydrous magnesium sulfate, and filtered. The residue was recrystallized from DCM and hexane to give the title compound (625 mg, Yield 65%).

Step C: (Tetrahydropyran-4-yl)-[2-phenyl-5-(1,1-dioxo-thiomorpholin-4-yl)methyl-1H-indol-7-yl] amine 5-(1,1-Dioxo-thiomorpholin-4-yl)methyl-2-phenyl-7-nitro-1H-indole prepared in Step B and tetrahydropyran-4-one were reacted according to the same procedure as Example 1 to give the title compound.

$^1$H-NMR (500 MHz, CDCl$_3$); δ 8.38 (br s, 1H), 7.69 (d, J=7.3 Hz, 1H), 7.44 (t, J=7.3 Hz, 2H), 7.32 (t, J=7.3 Hz, 1H), 7.00 (s, 1H), 6.75 (d, J=1.85 Hz, 1H), 6.47 (d, J=1.85 Hz, 1H), 4.07 (m, 2H), 3.65 (m, 3H), 3.57 (m, 2H), 3.02 (m, 8H), 2.12 (m, 2H), 1.61 (m, 2H)

EXAMPLE 37

(Tetrahydropyran-4-yl)-[2-phenyl-5-(2-oxo-piperazin-4-yl)methyl-1H-indol-7-yl]amine 5-Hydroxymethyl-2-phenyl-7-nitro-1H-indole prepared in Step A of Example 29, 2-oxopiperazine and 4-oxo-tetrahydropyran were sequentially reacted according to the same procedure as Example 36 to give the title compound.

$^1$H-NMR (500 MHz, CDCl$_3$); δ 8.96 (br s, 1H), 7.67 (d, J=7.3 Hz, 1H), 7.41 (t, J=7.3 Hz, 2H), 7.29 (t, J=7.3 Hz, 1H), 6.98 (s, 1H), 6.73 (d, J=1.85 Hz, 1H), 6.44 (d, J=1.85 Hz, 1H), 6.07 (brs, 1H), 4.00 (m, 2H), 3.61 (m, 3H), 3.53 (m, 2H), 3.33 (m, 2H), 3.21 (m, 2H), 2.66 (m, 2H), 1.51 (m, 2H)

EXAMPLE 38

Cyclopentyl-[2-(3-fluoro)phenyl-5-(2-oxo-piperazin-4-yl)methyl-1H-indol-7-yl]amine 2-(3-Fluorophenyl)-7-nitro-1H-indole-5-carboxylic acid prepared in Preparation 39 was reacted according to the same procedures as Step A of Example 28, Examples 32 and 36 to give the title compound.

$^1$H-NMR (400 MHz, CDCl$_3$); δ 8.46 (s, 1H), 7.50 (d, 1H), 7.42 (m, 2H), 7.06 (t, 1H), 7.02 (s, 1H), 6.80 (d, 1H), 6.54 (s, 1H), 4.03 (m, 1H), 3.72 (s, 2H), 3.07 (m, 8H), 2.16 (m, 2H), 1.85 (m, 2H), 1.74 (m, 2H), 1.67 (m, 2H)

EXAMPLE 39

(Tetrahydropyran-4-yl)-[2-(4-methoxy)phenyl-5-(1,1-dioxo-thiomorpholin-4-yl)methyl-1H-indol-7-yl]amine 2-(4-Methoxy-phenyl)-7-nitro-1H-indole-5-carboxylic acid prepared in Preparation 40 was reacted according to the same procedures as Step A of Example 28, Examples 32 and 36 to give the title compound.

$^1$H-NMR (500 MHz, DMSO-d$_6$); δ 10.79 (s, 1H), 7.67 (d, 2H), 7.01 (d, 2H), 6.68 (s, 1H), 6.57 (s, 1H), 6.24 (d, 1H), 5.26 (d, 1H), 3.90 (m, 2H), 3.77 (s, 3H), 3.61 (m, 1H), 3.58 (s, 2H), 3.46 (t, 2H), 3.04 (m, 4H), 2.83 (m, 4H), 2.01 (d, 2H), 1.43 (m, 2H)

EXAMPLES 40 to 78

The compounds prepared in Preparations 24 to 40, 43, 44 and 47 and commercially available ketone or aldehyde were reacted according to a method selected from Examples 26 to 37 to synthesize the Example Compounds in the following table.

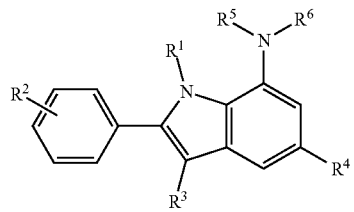

| Example | R$^1$ | R$^2$ | R$^3$ | R$^4$ | R$^5$ | R$^6$ |
|---|---|---|---|---|---|---|
| | | | H$^1$ NMR | | | |
| 40 | H | H | Me | Me | H | c-Pen |
| | (400 MHz, CDCl$_3$); δ 7.68 (br s, 1H), 7.59 (m, 2H), 7.45 (m, 2H), 7.32 (m, 1H), 6.87 (s, 1H), 6.40 (s, 1H), 3.97 (m, 1H), 2.45 (s, 3H), 2.40 (s, 3H), 2.09 (m, 2H), 1.78~1.56 (m, 4H) | | | | | |
| 41 | H | H | H | Me | H | THP-4-yl |
| | (500 MHz, MeOH-d$_4$); δ 7.74 (m, 2H), 7.39 (m, 2H), 7.24 (m, 1H), 6.71 (s, 1H), 6.63 (s, 1H), 6.28 (s, 1H), 4.01 (m, 2H), 3.68 (m, 1H), 3.58 (m, 2H), 2.32 (s, 3H), 2.12 (m, 2H), 1.56 (m, 2H) | | | | | |
| 42 | H | H | H | Me | H | (c-Pen)methyl |
| | (500 MHz, MEOH-d$_4$); δ 7.73 (m, 2H), 7.37 (m, 2H), 7.22 (m, 1H), 6.68 (2, 1H), 6.62 (s, 1H), 6.18 (s, 1H), 3.14 (d, J = 7.35 Hz, 2H), 2.32 (s, 3H), 2.30 (m, 1H), 1.91 (m, 2H), 1.69 (m, 2H), 1.59 (m, 2H), 1.36 (m, 2H) | | | | | |
| 43 | H | H | H | Me | H | (THP-4-yl)methyl |
| | (500 MHz, MEOH-d$_4$); δ 7.73 (m, 2H), 7.38 (m, 2H), 7.23 (m, 1H), 6.68 (2, 1H), 6.63 (s, 1H), 6.19 (s, 1H), 3.97 (m, 2H), 3.44 (m, 2H), 3.16 (m, 2H), 2.32 (s, 3H), 1.99 (m, 1H), 1.83 (m, 2H), 1.40 (m, 2H) | | | | | |
| 44 | H | H | H | Me | H | 1-Me-Pid-4-yl |
| | (500 MHz, MeOH-d$_4$); δ 7.73 (m, 2H), 7.38 (m, 2H), 7.24 (m, 1H), 6.70 (s, 1H), 6.63 (s, 1H), 6.24 (s, 1H), 3.47 (m, 1H), 2.96 (m, 2H), 2.34 (s, 3H), 2.32 (s, 3H), 2.26 (m, 2H), 2.17 (m, 2H), 1.59 (m, 2H) | | | | | |
| 45 | H | H | H | Me | H | 1-Ac-Pid-4-yl |
| | (500 MHz, DMSO-d$_6$); δ 10.77 (brs, 1H), 7.74 (m, 2H), 7.42 (m, 2H), 7.26 (m, 1H), 6.66 (d, J = 1.85 Hz, 1H), 6.56 (s, 1H), 6.14 (s, 1H), 5.22 (d, J = 7.95, 1H), 4.28 (m, 1H), 3.82 (m, 1H), 3.62 (m, 1H), 3.13(m, 1H), 2.83 (m, 1H), 2.26 (s, 3H), 2.05 (m, 2H), 2.00 (s, 3H), 1.31 (m, 2H) | | | | | |
| 46 | H | H | H | Cl | H | c-Pen |
| | (500 MHz, DMSO-d$_6$); δ 11.04 (brs, 1H), 7.75 (m, 2H), 7.45 (m, 2H), 7.30 (m, 1H), 6.76 (d, J = 1.8 Hz, 1H), 6.72 (d, J = 2.45 Hz, 1H), 6.14 (d, J = 1.8 Hz, 1H), 3.84 (m, 1H), 2.00 (m, 2H), 1.71(m, 2H), 1.60 (m, 2H), 1.52 (m, 2H) | | | | | |
| 47 | H | H | H | Cl | H | c-Hex |
| | (500 MHz, CDCl$_3$); δ 8.18 (brs, 1H), 7.65 (m, 2H), 7.44 (m, 5H), 7.31(m, 2H), 7.03 (s, 1H), 6.70 (s, 1H), 6.47 (d, 1H), 3.38 (m, 1H), 2.16 (m, 2H), 1.81 (m, 2H), 1.71 (m, 1H), 1.42 (m, 2H), 1.24 (m, 4H) | | | | | |
| 48 | H | H | H | Cl | H | THP-4-yl |
| | (500 MHz, DMSO-d$_6$); δ 11.09 (brs, 1H), 7.74 (m, 2H), 7.43 (m, 2H), 7.29 (m, 1H), 6.77 (s, 1H), 6.72 (s, 1H), 6.24 (s, 1H), 5.60 (m, 1H), 4.28 (m, 1H), 3.86 (m, 2H), 3.43 (m, 2H), 1.96 (m, 2H), 1.41 (m, 2H) | | | | | |

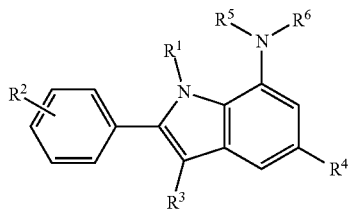

| Example | R¹ | R² | R³ | R⁴ | R⁵ | R⁶ |
|---|---|---|---|---|---|---|
| | | | | H¹ NMR | | |
| 49 | H | H | H | Cl | H | (c-Pen)methyl |
| | (500 MHz, CDCl₃); 8.22 (brs, 1H), 7.65 (m, 2H), 7.43 (m, 2H), 7.32 (m, 1H), 7.05 (m, 1H), 6.71 (m, 1H), 6.46 (m, 1H), 3.16 (m, 2H), 2.27 (m, 1H), 1.89 (m, 2H), 1.72-1.48 (m, 4H), 1.32 (m, 2H) | | | | | |
| 50 | H | H | H | Cl | H | (THP-4-yl)methyl |
| | (500 MHz, DMSO-d₆); δ 11.08 (s, 1H), 7.75 (d, J = 7.3 Hz, 2H), 7.44 (t, J = 7.3 Hz, 2H), 7.29 (t, J = 7.3 Hz, 1H), 6.77 (d, J = 1.85 Hz, 1H), 6.72 (d, J = 1.85 Hz, 1H), 6.15 (d, J = 1.85 Hz, 1H), 5.71 (m, 1H), 3.86 (m, 2H), 3.07 (m, 2H), 1.87 (m, 1H), 1.72 (m, 2H), 1.28 (m, 2H) | | | | | |
| 51 | H | H | H | Cl | H | 1-benzyl-Pyd-3-yl |
| | (500 MHz, CDCl₃); δ 10.33 (brs, 1H), 7.83 (m, 2H), 7.47 (m, 5H), 7.41 (m, 2H), 7.28 (m, 1H), 7.00 (d, J = 1.85 Hz, 1H), 6.69 (d, J = 1.85 Hz, 1H), 6.19 (d, J = 1.8, 1H), 4.49 (m, 1H), 4.36 (d, J = 12.8 Hz, 2H), 4.09 (d, J = 12.8 Hz, 2H), 3.82 (m, 1H), 3.59 (m, 1H), 3.18 (m, 1H), 3.11 (m, 1H), 2.41 (m, 2H) | | | | | |
| 52 | H | H | H | Cl | H | 1-Me-Pid-4-yl |
| | (500 MHz, DMSO-d₆); δ 11.06 (brs, 1H), 9.57 (brs, 1H), 7.75 (m, 2H), 7.45 (m, 2H), 7.31 (m, 1H), 6.80 (s, 1H), 6.74 (s, 1H), 6.29 (s, 1H), 3.66 (m, 1H), 3.49 (m, 2H), 3.11 (m, 2H), 2.78 (s, 3H), 2.23 (m, 2H), 1.61 (m, 2H) | | | | | |
| 53 | H | H | H | Cl | H | 1,5-dioxa-spiro[4,5]decan-8-yl |
| | (500 MHz, DMSO-d₆); δ 11.04 (s, 1H), 7.76 (d, J = 6.7 Hz, 2H), 7.44 (t, J = 7.3 Hz, 2H), 7.30 (t, J = 7.3 Hz, 1H), 6.73 (m, 2H), 6.22 (d, J = 1.85 Hz, 1H), 5.56 (m, 1H), 3.85 (m, 4H), 3.50 (m, 1H), 1.98 (m, 2H), 1.73 (m, 2H), 1.65 (m, 2H), 1.51 (m, 2H) | | | | | |
| 54 | H | H | H | Cl | H | CH₂—CH(CH₂OH)₂ |
| | (500 MHz, DMSO-d₆); δ 11.44 (s, 1H), 7.82 (d, J = 7.3 Hz, 2H), 7.42 (t, J = 7.3 Hz, 2H), 7.28 (t, J = 7.3 Hz, 1H), 6.76 (d, J = 1.85 Hz, 1H), 6.73 (d, J = 1.85 Hz, 1H), 6.24 (d, J = 1.85 Hz, 1H), 3.57 (m, 4H), 3.42 (m, 1H), 3.50 (m, 1H), 1.98 (m, 2H), 1.73 (m, 2H), 1.65 (m, 2H), 1.51 (m, 2H) | | | | | |
| 55 | H | H | H | Me | Me | THP-4-yl |
| | (400 MHz, CDCl₃); δ 8.42 (br s, 1H), 7.67 (d, J = 8 Hz, 2H), 7.46 (t, J = 7.3 Hz, 1H), 7.35 (t, 1H), 6.90 (s, 1H), 6.74 (s, 1H), 4.15 (d, J = 8 Hz, 2H), 3.41 (t, 2H), 3.25 (m, 1H), 2.80 (s, 3H), 1.76 (m, 4H) | | | | | |
| 56 | H | H | H | ![thiomorpholine-S,S-dioxide] | H | (THP-4-yl)methyl |
| | (500 MHz, CDCl₃); δ 8.54 (br s, 1H), 7.67 (d, J = 7.3 Hz, 1H), 7.43 (t, J = 7.3 Hz, 2H), 7.32 (t, J = 7.3 Hz, 1H), 6.98 (s, 1H), 6.75 (d, J = 1.85 Hz, 1H), 6.42 (d, J = 1.85 Hz, 1H), 4.07 (m, 2H), 3.67 (s, 2H), 3.46 (m, 2H), 3.19 (m, 2H), 3.04 (m, 8H), 1.97 (m, 1H), 1.80 (m, 2H), 1.50 (m, 2H) | | | | | |
| 57 | H | H | H | ![thiomorpholine-S,S-dioxide] | (THP-4-yl)methyl | (THP-4-yl)methyl |
| | (400 MHz, CDCl₃); δ 8.37 (br s, 1H), 7.62 (d, J = 7.3 Hz, 1H), 7.46 (t, J = 7.3 Hz, 2H), 7.35 (t, J = 7.3 Hz, 1H), 6.90 (s, 1H), 6.77 (d, J = 1.85 Hz, 1H), 3.95 (m, 4H), 3.72 (s, 2H), 3.32 (m, 4H), 2.99 (m, 8H), 1.83 (m, 2H), 1.78 (m, 2H), 1.31 (m, 4H) | | | | | |
| 58 | H | H | H | ![thiomorpholine-S,S-dioxide] | THP-4-yl | THP-4-yl |
| | (400 MHz, DMSO-d₆); δ 10.79 (s, 1H), 7.93 (d, 2H), 7.45 (t, 2H), 7.32 (t, 1H), 7.31 (s, 1H), 7.00 (s, 1H), 6.80 (s, 1H), 3.81 (d, 4H), 3.75 (s, 2H), 3.49 (m, 2H), 3.28 (m, 2H), 3.11 (m, 4H), 2.89 (m, 4H), 1.81 (m, 4H), 1.31 (m, 4H) | | | | | |

-continued

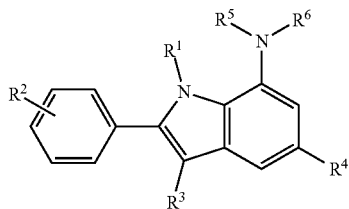

| Example | R¹ | R² | R³ | R⁴ | R⁵ | R⁶ |
|---|---|---|---|---|---|---|
| | | | H¹ NMR | | | |
| 59 | H | H | H | F | H | 1-methyl-Pid-4-yl |
| | (400 MHz, DMSO-d₆); δ 7.87 (d, 2H), 7.45 (t, 2H), 7.31 (m, 1H), 6.76 (s, 1H), 6.51 (s, 1H), 6.14 (s, 1H), 3.65 (br s, 1H), 3.41 (br s, 2H), 2.99 (br s, 2H), 2.69 (s, 1H), 2.17 (br s, 2H), 1.79 (br s, 2H) | | | | | |
| 60 | H | H | H | F | H | Pid-(CH₂)₂—OH |
| | (400 MHz, DMSO-d₆); δ 7.78 (d, 2H), 7.45 (t, 2H), 7.30 (t, 1H), 6.75 (s, 1H), 6.46 (d, 1H), 6.07 (d, 1H), 3.37 (t, 2H), 3.36 (t, 1H), 2.90 (d, 2H), 2.45 (t, 2H), 2.20 (t, 2H), 2.03 (t, 2H), 1.09 (t, 2H) | | | | | |
| 61 | H | H | H | F | H | 1-(THP-4-yl)Pid-4-yl |
| | (400 MHz, CDCl₃); δ 7.78 (br s, 2H), 7.36 (br s, 2H), 7.26 (br s, 1H), 6.71 (s, 1H), 6.68 (d, 1H), 6.12 (s, 1H), 3.90 (br s, 2H), 3.46 (br s, 2H), 3.20 (br s, 2H), 3.09 (br s, 2H), 2.61 (br s, 1H), 2.45 (br s, 2H), 2.23 (d, 2H), 1.87 (br sm 2H), 1.61 (br s, 2H), 1.58 (br s, 2H) | | | | | |
| 62 | H | H | H | OPh | H | THP-4-yl |
| | (400 MHz, CDCl₃); δ 8.12 (brs, 1H), 7.68 (d, 2H), 7.44 (t, 2H), 7.34~7.27 (m, 3H), 7.01 (m, 3H), 6.74 (m, 2H), 6.35 (d, J = 2.0 Hz, 1H), 4.05 (m, 2H), 3.62~3.49 (m, 4H), 2.12 (m, 2H), 1.57 (m, 2H) | | | | | |
| 63 | H | H | H | 4-(piperazin-2-one-yl)methyl | H | (THP-4-yl)methyl |
| | (500 MHz, CDCl₃); δ 9.10 (br s, 1H), 7.67 (d, J = 7.3 Hz, 1H), 7.40 (t, J = 7.3 Hz, 2H), 7.28 (t, J = 7.3 Hz, 1H), 6.95 (s, 1H), 6.72 (d, J = 1.85 Hz, 1H), 6.38 (d, J = 1.85 Hz, 1H), 6.01 (brs, 1H), 4.00 (m, 2H), 3.60 (s, 2H), 3.38 (m, 2H), 3.32 (m, 2H), 3.20 (m, 2H), 3.11 (m, 2H), 2.66 (m, 2H), 1.89 (m, 1H), 1.74 (m, 2H), 1.44 (m, 2H) | | | | | |
| 64 | (Me)₂N(CH₂)₂— | H | H | Cl | H | THP-4-yl |
| | (400 MHz, CDCl₃); δ 7.49 (m, 4H), 7.44 (t, 1H), 6.96 (s, 1H), 6.49 (s, 1H), 6.42 (s, 1H), 5.59 (d, 1H), 4.37 (d, 2H), 3.88 (d, 2H), 3.54 (m, 1H), 3.46 (t, 2H), 2.27 (t, 2H), 2.17 (m, 4H), 1.96 (br s, 2H) 1.51 (m, 2H), 0.67 (m, 6H), | | | | | |
| 65 | Me | H | H | Cl | Me | Me |
| | (400 MHz, CDCl₃); δ 7.79 (m, 2H), 7.46 (m, 2H), 7.41 (m, 1H), 7.27 (s, 1H), 6.84 (s, 1H), 6.49 (s, 1H), 3.93 (s, 3H), 2.81 (s, 6H) | | | | | |
| 66 | Me | H | H | Cl | Me | THP-4-yl |
| | (400 MHz, CDCl₃); δ 7.79 (m, 2H), 7.46 (m, 2H), 7.41 (m, 1H), 7.27 (s, 1H), 6.96 (m, 1H), 6.47 (s, 1H), 3.98 (s, 3H), 3.97 (m, 2H), 3.48 (m, 2H), 3.21 (m, 1H), 2.76 (s, 3H), 1.92 (m, 1H), 1.69 (m, 3H) | | | | | |
| 67 | H | H | morpholin-4-yl-methyl | Cl | H | c-Pen |
| | (400 MHz, CDCl₃); δ 7.77 (d, 2H), 7.49 (t, 2H), 7.38 (t, 1H), 7.22 (s, 1H), 6.51 (s, 1H), 3.69 (m, 4H), 3.61 (s, 2H), 2.50 (br s, 4H), 3.92 (m, 1H), 2.11 (m, 2H), 1.78 (m, 2H), 1.68 (m, 2H), 1.58 (m, 2H) | | | | | |
| 68 | H | H | morpholin-4-yl-methyl | Cl | H | THP-4-yl |
| | (400 MHz, CDCl₃); δ 7.77 (d, 2H), 7.47 (t, 2H), 7.41 (t, 1H), 7.26 (s, 1H), 6.51 (s, 1H), 4.03 (d, 2H), 3.69 (br s, 4H), 3.61 (d, 2H), 2.50 (d, 2H), 2.49 (br s, 1H), 2.11 (d, 2H), 1.57 (d, 2H) | | | | | |
| 69 | H | H | 4-(piperazin-2-one-yl)methyl | Cl | H | THP-4-yl |

-continued

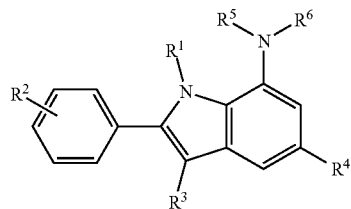

| Example | R¹ | R² | R³ | R⁴ | R⁵ | R⁶ |
|---|---|---|---|---|---|---|
| | | | H¹ NMR | | | |

(400 MHz, DMSO-d$_6$); δ 11.09 (s, 1H), 7.83 (d, J = 8 Hz, 2H), 7.70 (s, 1H), 7.54 (t, 2H), 7.40 (t, 1H), 6.96 (s, 1H), 6.31 (s, 1H), 5.64 (d, J = 8 Hz, 1H), 3.90 (d, J = 12 Hz, 2H), 3.62 (m, 1H), 3.61 (s, 3H), 3.50 (m, 2H), 3.31 (s, 2H), 2.96 (s, 2H), 2.59 (s, 2H), 2.00 (d, J = 12 Hz, 2H), 1.46 (m, 2H)

| 70 | H | H | 4-ethyl-3-oxopiperazin-1-yl | Cl | H | c-Pen |

(400 MHz, DMSO-d$_6$); δ 11.07 (s, 1H), 7.82 (d, J = 8 Hz, 2H), 7.71 (s, 1H), 7.53 (t, 2H), 7.40 (t, 1H), 6.94 (s, 1H), 6.20 (s, 1H), 5.70 (d, J = 8 Hz, 1H), 3.88 (m, 1H), 3.61 (s, 2H), 3.31 (s, 2H), 2.96 (s, 2H), 2.59 (m, 2H), 2.03 (m, 2H), 1.74 (m, 2H), 1.64 (m, 2H), 1.54 (m, 2H)

| 71 | H | H | 4-ethyl-3-oxopiperazin-1-yl | Cl | H | (THP-4-yl)methyl |

(400 MHz, DMSO-d$_6$); δ 11.12 (s, 1H), 7.83 (d, J = 8 Hz, 2H), 7.71 (s, 1H), 7.54 (t, 2H), 7.40 (t, 1H), 6.96 (s, 1H), 6.21 (s, 1H), 5.73 (m, 1H), 3.91 (d, J = 12 Hz, 2H), 3.89 (s, 2H), 3.36 (m, 2H), 3.31 (s, 2H), 3.10 (m, 2H), 2.96 (s, 2H), 2.59 (m, 2H), 1.90 (m, 1H), 1.74 (d, J = 12 Hz, 2H), 1.34 (m, 2H)

| 72 | H | H | Br | (1,1-dioxothiomorpholin-4-yl)methyl | H | THP-4-yl |

(500 MHz, CDCl$_3$); δ 8.57 (br s, 1H), 7.82 (d, J = 7.3 Hz, 1H), 7.49 (t, J = 7.3 Hz, 2H), 7.39 (t, J = 7.3 Hz, 1H), 6.95 (s, 1H), 6.49 (d, J = 1.85 Hz, 1H), 4.04 (m, 2H), 3.67 (s, 2H), 3.64 (m, 1H), 3.56 (m, 2H), 3.00 (m, 8H), 2.09 (m, 2H), 1.56 (m, 2H)

| 73 | H | H | Br | (1,1-dioxothiomorpholin-4-yl)methyl | H | c-Pen |

(500 MHz, CDCl$_3$); δ 8.29 (br s, 1H), 7.82 (d, J = 7.3 Hz, 1H), 7.49 (t, J = 7.3 Hz, 2H), 7.39 (t, J = 7.3 Hz, 1H), 6.93 (s, 1H), 6.53 (d, J = 1.85 Hz, 1H), 3.95 (m, 1H), 3.70 (s, 2H), 3.02 (m, 8H), 2.10 (m, 2H), 1.77 (m, 2H), 1.68 (m, 2H), 1.56 (m, 2H)

| 74 | H | H | Br | (1,1-dioxothiomorpholin-4-yl)methyl | H | (THP-4-yl)methyl |

(500 MHz, CDCl$_3$); δ 8.20 (br s, 1H), 7.80 (d, J = 7.3 Hz, 1H), 7.49 (t, J = 7.3 Hz, 2H), 7.40 (t, J = 7.3 Hz, 1H), 6.97 (s, 1H), 6.50 (d, J = 1.85 Hz, 1H), 4.03 (m, 2H), 3.71 (s, 2H), 3.42 (m, 2H), 3.18 (m, 2H), 3.03 (m, 8H), 1.94 (m, 1H), 1.78 (m, 2H), 1.47 (m, 2H)

| 75 | H | m-F | H | (1,1-dioxothiomorpholin-4-yl)methyl | H | THP-4-yl |

(400 MHz, CDCl$_3$); δ 8.31 (s, 1H), 7.46 (m, 3H), 7.07 (m, 2H), 6.82 (d, 1H), 6.55 (s, 1H), 4.12 (m, 2H), 3.72 (m, 3H), 3.64 (t, 2H), 3.07 (m, 8H), 2.18 (d, 2H), 1.66 (m, 2H)

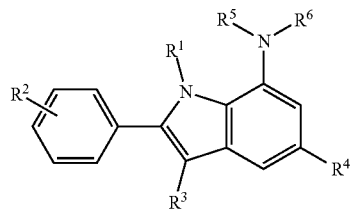

| Example | R¹ | R² | R³ | R⁴ H¹ NMR | R⁵ | R⁶ |
|---|---|---|---|---|---|---|
| 76 | H | p-MeO— | H | ![morpholine sulfone CH2] | H | c-Pen |
| | | | | (400 MHz, DMSO-d₆); δ 10.85 (s, 1H), 7.73 (d, 2H), 7.05 (d, 2H), 6.71 (s, 1H), 6.61 (d, 1H), 6.24 (s, 1H), 5.40 (d, 1H), 3.90 (m, 1H), 3.82 (s, 3H), 3.64 (s, 1H), 3.10 (m, 4H), 2.89 (m, 4H), 2.05 (m, 2H), 1.77 (m, 2H), 1.64 (m, 2H), 1.58 (m, 2H) | | |
| 77 | H | p-MeO— | H | ![morpholine sulfone CH2] | H | isobutyl |
| | | | | (400 MHz, CDCl₃); δ 8.33 (s, 1H), 7.67 (d, 2H), 7.43 (t, 2H), 7.31 (t, 1H), 6.98 (s, 1H), 6.75 (s, 1H), 6.47 (s, 1H), 3.68 (s, 1H), 3.28 (t, 2H), 3.03 (m, 8H), 2.63 (s, 1H), 1.82 (m, 1H), 1.65 (m, 2H), 1.00 (d, 6H) | | |
| 78 | H | p-BOC—NH | H | Cl | H | c-Pen |
| | | | | (400 MHz, CDCl₃); δ 8.62 (br s, 1H), 7.489d, 2H), 7.33 (d, 2H), 6.98 (d, 1H), 6.61 (s, 1H), 6.58 (d, 1H), 6.42 (d, 1H), 3.83 (m, 1H), 2.08 (m, 2H), 1.76~1.59 (m, 6H), 1.49 (s, 9H) | | |

EXAMPLE 79

(Tetrahydropyran-4-yl)-(5-chloro-3-phenyl-1H-indol-7-yl)-amine

5-Chloro-7-nitro-3-phenyl-1H-indole prepared in Preparation 41 and tetrahydropyran-4-one were reacted according to the same procedure as Example 1 to give the title compound.

$^1$H-NMR (400 MHz, CDCl$_3$); δ 8.10 (br s, 1H), 7.61 (d, J=8 Hz, 2H), 7.43 (t, 2H), 7.38 (s, 1H), 7.31 (m, 2H), 6.56 (s, 1H), 4.05 (m, 2H), 3.65 (m, 1H), 3.62 (t, 2H), 2.15 (d, J=12 Hz, 2H), 1.62 (m, 5H)

EXAMPLE 80

Cyclopentyl-(5-chloro-3-phenyl-1H-indol-7-yl)-amine

5-Chloro-7-nitro-3-phenyl-1H-indole prepared in Preparation 41 and cyclopentanone were reacted according to the same procedure as Example 1 to give the title compound.

$^1$H-NMR (400 MHz, CDCl$_3$); δ 8.06 (br s, 1H), 7.58 (d, J=8 Hz, 2H), 7.39 (t, 2H), 7.33 (s, 1H), 7.26 (m, 1H), 7.17 (s, 1H), 6.51 (s, 1H), 3.91 (m, 1H), 2.08 (m, 2H), 1.74 (m, 2H), 1.66 (m, 2H), 0.54 (m, 2H)

EXAMPLE 81

(Tetrahydropyran-4-yl)methyl-(5-chloro-3-phenyl-1H-indol-7-yl)-amine

5-Chloro-7-nitro-3-phenyl-1H-indole prepared in Preparation 41 and tetrahydropyran-4-carboxyaldehyde were reacted according to the same procedure as Example 1 to give the title compound.

$^1$H-NMR (400 MHz, CDCl$_3$); δ 8.08 (br s, 1H), 7.61 (d, J=8 Hz, 2H), 7.44 (t, 2H), 7.37 (s, 1H), 7.29 (m, 2H), 6.52 (s, 1H), 4.04 (dd, 2H), 3.44 (t, 2H), 3.19 (d, J=4 Hz, 2H), 1.97 (m, 1H), 1.79 (d, J=12 Hz, 2H), 1.41 (m, 2H)

EXAMPLE 82

Cyclopentyl-[2-(4-aminophenyl)-5-chloro-1H-indol-7-yl]-amine

Cyclopentyl-[2-(4-BOC-aminophenyl)-5-chloro-1H-indol-7-yl]-amine (430 mg, 1 mmol) prepared in Example 78 was added to DCM (5 mL). TFA (5 mL) was added thereto, and the mixture was stirred for 2 h. After completion of the reaction, TFA was removed under reduced pressure, and the residue was purified by column chromatography to give the title compound (310 mg, Yield 95%).

$^1$H-NMR (400 MHz, DMSO-d$_6$); δ 10.76 (br s, 1H), 7.47 (d, 1H), 6.70 (d, 1H), 6.63 (d, 1H), 6.43 (d, 1H), 6.11 (d, 1H), 5.61 (d, 1H), 5.30 (br s, 2H), 3.68 (m, 1H), 2.03 (m, 2H), 1.74~1.52 (m, 6H)

EXAMPLE 83

Cyclopentyl-{5-chloro-2-[4-(1-methyl-piperidin-4-yl)aminophenyl]-1H-indol-7-yl}-amine Cyclopentyl-[2-(4-aminophenyl)-5-chloro-1H-indol-7-yl]-amine prepared in Example 82 and 1-methyl-piperidin-4-one were reacted according to the same procedure as Step B of Example 1 to give the title compound.

¹H-NMR (400 MHz, MeOH-d₄/CDCl₃); δ 7.51 (d, 2H), 6.89 (d, 1H), 6.62 (d, 2H), 6.49 (s, 1H), 6.33 (d, 1H), 3.91 (m, 1H), 3.37 (m, 1H), 3.04 (m, 2H), 2.49~2.39 (m, 4H), 2.08 (m, 2H), 1.78~1.64 (m, 6H)

EXAMPLE 84

N-[4-(5-chloro-7-cyclopentylamino-1H-indol-2-yl)-phenyl]methanesulfonamide

Cyclopentyl-[2-(4-aminophenyl)-5-chloro-1H-indol-7-yl]amine prepared in Example 82 and methanesulfonylchloride were reacted according to the same procedure as Example 22 to give the title compound.
¹H-NMR (500 MHz, MeOH-d₄/CDCl₃); δ 7.63 (d, 2H), 7.26 (d, 2H), 6.93 (s, 1H), 6.59 (s, 1H), 6.36 (s, 1H), 3.86 (m, 1H), 2.96 (s, 3H), 2.06 (m, 2H), 1.74~1.58 (m, 6H)

EXAMPLE 85

Cyclopentyl-{5-(1,1-dioxo-thiomorpholin-4-yl)methyl-2-[4-(acetyl)aminophenyl]-1H-indol-7-yl}-amine 2-(4-BOC-amino-phenyl)-7-nitro-1H-indole-5-carboxylic acid prepared in Preparation 40 was reacted according to the same procedures as Example 28, Step A of Example 29 and Example 36 sequentially to give the title compound.
¹H-NMR (400 MHz, MeOH-d₄/CDCl₃); δ 9.08 (s, 1H), 7.48 (d, J=8 Hz, 2H), 7.39 (dd, J1=8 Hz, J2=4 Hz, 2H), 6.89 (s, 1H), 6.60 (d, J=4 Hz, 1H), 3.96 (m, 1H), 3.67 (s, 2H), 3.00 (m, 8H), 2.18 (s, 3H), 2.06 (m, 2H), 1.26~1.77 (m, 6H)

EXAMPLES 86 to 89

7-Amino-5-(1,1-dioxo-thiomorpholin-4-yl)methyl-2-[4-(acetyl)aminophenyl]-1H-indole prepared as an intermediate in the process of Example 85 and commercially available ketone or aldehyde were reacted according to the same procedure as Step B of Example 1 to synthesize the Example Compounds in the following table.

EXAMPLE 90

(5-Methyl-2-phenyl-1H-indol-7-yl)-piperidin-4-yl-amine

Step A: 1-BOC-(5-methyl-2-phenyl-1H-indol-7-yl)-piperidin-4-yl-amine

7-Amino-5-methyl-2-phenyl-1H-indole prepared in Example 2 and 1-BOC-piperidinone were reacted according to the same procedure as Preparation 23 to give the title compound.

Step B: (5-Methyl-2-phenyl-1H-indol-7-yl)-piperidin-4-yl-amine

1-BOC-(5-methyl-2-phenyl-1H-indol-7-yl)-piperidin-4-yl-amine prepared in Step A was reacted according to the same procedure as Example 82 to give the title compound.
¹H-NMR (500 MHz, DMSO-d6); δ 11.33 (brs, 1H), 8.68 (m, 2H), 7.83 (m, 2H), 7.41 (m, 2H), 7.26 (m, 1H), 6.72 (m, 2H), 6.29 (s, 1H), 3.74 (m, 1H), 3.47 (m, 2H), 3.01 (m, 2H), 2.28 (s, 3H), 2.13 (m, 2H), 1.77 (m, 2H)

EXAMPLE 91

[1-(Methanesulfonyl)piperidin-4-yl]-(5-methyl-2-phenyl-1H-indol-7-yl)-amine (5-Methyl-2-phenyl-1H-indol-7-yl)-piperidin-4-yl-amine prepared in Example 90 and methanesulfonylchloride were reacted according to the same procedure as Example 22 to give the title compound.
¹H-NMR (500 MHz, DMSO-d₆); δ 10.79 (brs, 1H), 7.74 (m, 2H), 7.42 (m, 2H), 7.26 (m, 1H), 6.66 (s, 1H), 6.57 (s, 1H), 6.11 (s, 1H), 5.27 (m, 1H), 3.57 (m, 2H), 3.13 (m, 1H), 2.93 (m, 1H), 2.87 (s, 3H), 2.25 (s, 3H), 2.14 (m, 2H), 1.46 (m, 2H)

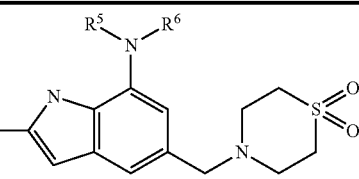

| Example | R⁵ | R⁶ | ¹H NMR |
|---|---|---|---|
| 86 | c-Pen | c-Pen | (400 MHz, MeOH-d₄/CDCl₃); δ 8.66 (s, 1H), 7.60 (m, 4H), 7.34 (s, 1H), 7.26 (s, 1H), 7.02 (s, 1H), 6.67 (s, 1H), 3.75 (m, 4H), 2.98~3.04 (m, 8H), 2.20 (s, 1H), 1.79~1.82 (m, 4H), 1.49 (m, 8H), 1.25 (m, 4H) |
| 87 | H | (THP-4-yl)methyl | (400 MHz, MeOH-d₄/CDCl₃); δ 8.95 (s, 1H), 7.57 (d, J = 4 Hz, 2H), 7.49 (d, J = 4 Hz, 2H), 7.33 (s, 1H), 7.00 (s, 1H), 6.65 (s, 1H), 6.40 (s, 1H), 4.02 (m, 4H), 3.74 (s, 2H), 3.42 (t, 2H), 3.17 (d, J = 4 Hz, 2H), 3.02 (m, 8H), 2.21 (s, 3H), 1.97 (m, 1H), 1.78 (m, 2H), 1.47 (m, 2H). |
| 88 | (THP-4-yl)methyl | (THP-4-yl)methyl | (400 MHz, MeOH-d₄/CDCl₃); δ 8.33 (s, 1H), 7.56~7.62 (m, 4H), 7.49 (s, 1H), 7.23 (s, 1H), 6.89 (s, 1H), 6.71 (s, 1H), 3.96 (m, 4H), 3.71 (s, 1H), 3.30 (m, 4H), 2.86~3.03 (m, 12H), 2.20 (s, 3H), 1.63~1.81 (m, 6H), 1.05~1.37 (m, 4H). |
| 89 | H | THP-4-yl | (400 MHz, MeOH-d₄/CDCl₃); δ 9.28 (s, 1H), 7.55 (d, J = 4 hz, 2H), 7.47 (d, J = 4 Hz, 2H), 7.37 (s, 1H), 6.94 (s, 1H), 6.63 (s, 1H), 6.42 (s, 1H), 4.10 (m, 2H), 3.58~3.69 (m, 5H), 3.02 (m, 8H), 2.17 (s, 3H), 2.12 (m, 2H), 1.58 (m, 3H) |

EXAMPLE 92

2-Hydroxy-1-[4-(5-methyl-2-phenyl-1H-indol-7-yl) amino-piperidin-1-yl]-ethanone (5-Methyl-2-phenyl-1H-indol-7-yl)-piperidin-4-yl-amine (305 mg, 1 mmol) prepared in Example 90 was dissolved in DMF (5 mL). Hydroxyacetic acid (76 mg, 1 mmol), EDC (232 mg, 1.3 mmol), HOBT (229 mg, 1.5 mmol) and $Et_3N$ (280 uL, 2 mmol) were added thereto, and the mixture was stirred for 4 h at room temperature. After completion of the reaction, saturated aqueous $NaHCO_3$ solution was added to the reaction mixture, which was then extracted with EtOAc, washed with saturated aqueous NaCl solution and 1N HCl, dried over anhydrous magnesium sulfate, and filtered. The solvent was removed under reduced pressure, and the residue was purified by column chromatography to give the title compound.
$^1$H-NMR (500 MHz, MeOH-$d_4$); δ 7.72 (m, 2H), 7.38 (m, 2H), 7.23 (m, 1H), 6.71 (2, 1H), 6.63 (s, 1H), 6.30 (s, 1H), 4.40 (m, 1H), 4.23 (m, 2H), 3.74 (m, 2H), 3.24 (m, 1H), 3.02 (m, 1H), 2.33 (s, 3H), 2.19 (m, 2H), 1.45 (m, 2H)

EXAMPLE 93

(5-Chloro-2-phenyl-1H-indol-7-yl)-piperidin-4-yl-amine

7-Amino-5-chloro-2-phenyl-1H-indole prepared in Example 3 and 1-BOC-4-piperidinone were reacted according to the same procedure as Step B of Example 1 to give the title compound.
$^1$H-NMR (500 MHz, DMSO-d6); δ 11.57 (s, 1H), 8.66 (brs, 2H), 7.87 (d, J=6.7 Hz, 2H), 7.42 (t, J=7.3 Hz, 2H), 7.28 (t, J=7.3 Hz, 1H), 6.75 (m, 2H), 6.26 (m, 1H), 3.76 (m, 1H), 3.36 (m, 2H), 3.05 (m, 2H), 2.12 (m, 2H), 1.70 (m, 2H)

EXAMPLE 94

4-(5-Chloro-2-phenyl-1H-indol-7-yl)amino-piperidin-1-yl-carboxylic acid phenylamide (5-Chloro-2-phenyl-1H-indol-7-yl)-piperidin-4-yl-amine prepared in Example 93 and phenylisocyanate were reacted according to the same procedure as Example 22 to give the title compound.
$^1$H-NMR (500 MHz, DMSO-d6); δ 11.05 (s, 1H), 8.53 (s, 1H), 7.76 (d, J=7.3 Hz, 2H), 7.44 (m, 4H), 7.30 (t, J=7.3 Hz, 1H), 7.20 (t, J=7.3 Hz, 1H), 6.91 (t, J=7.3 Hz, 1H), 6.77 (d, J=1.85 Hz, 1H), 6.73 (d, J=1.85 Hz, 1H), 6.29 (d, J=1.85 Hz, 1H), 5.62 (m, 1H), 4.08 (m, 2H), 3.65 (m, 1H), 3.04 (m, 2H), 2.05 (m, 2H), 1.36 (m, 2H)

EXAMPLE 95

1-[4-(5-Chloro-2-phenyl-1H-indol-7-yl)amino-piperidin-1-yl]-2-dimethylamino-ethanone Step A: 1-[4-(5-Chloro-2-phenyl-1H-indol-7-yl) amino-piperidin-1-yl]-2-BOC-amino-ethanone (5-Chloro-2-phenyl-1H-indol-7-yl)-piperidin-4-yl-amine prepared in Example 93 and N-BOC-Gly-OH were reacted according to the same procedure as Example 92 to give the title compound.

Step B: 1-[4-(5-Chloro-2-phenyl-1H-indol-7-yl) amino-piperidin-1-yl]-2-amino-ethanone 1-[4-(5-Chloro-2-phenyl-1H-indol-7-yl)amino-piperidin-1-yl]-2-BOC-amino-ethanone prepared in Step A was reacted according to the same procedure as Example 82 to give the title compound.

Step C: 1-[4-(5-Chloro-2-phenyl-1H-indol-7-yl) amino-piperidin-1-yl]-2-dimethylamino-ethanone 1-[4-(5-Chloro-2-phenyl-1H-indol-7-yl)amino-piperidin-1-yl]-2-amino-ethanone prepared in Step B and formaldehyde were reacted according to the same procedure as Step B of Example 1 to give the title compound.
$^1$H-NMR (500 MHz, DMSO-d6); δ 11.97 (s, 1H), 9.54 (brs, 1H), 7.95 (d, J=6.7 Hz, 2H), 7.40 (t, J=7.3 Hz, 2H), 7.26 (t, J=7.3 Hz, 1H), 6.74 (m, 2H), 6.25 (m, 1H), 4.41-4.22 (m, 3H), 3.69 (m, 2H), 3.22 (m, 1H), 3.02 (m, 1H), 2.79 (m, 6H), 2.03 (m, 2H), 1.51 (m, 2H)

EXAMPLE 96

[5-(1,1-Dioxo-thiomorpholin-4-yl)methyl-2-phenyl-1H-indol-7-yl]-(piperidin-4-yl)methyl-amine 5-(1,1-Dioxo-thiomorpholin-4-yl)methyl-2-phenyl-7-nitro-1H-indole prepared in Step B of Example 36 and 1-BOC-piperidine-4-carboxyaldehyde were reacted according to the same procedures as Examples 1 and 90 sequentially to give the title compound.
$^1$H-NMR (400 MHz, DMSO-$d_6$, 2TFA salt); δ 11.10 (s, 1H), 8.57 (m, 1H), 8.28 (m, 1H), 7.82 (d, 2H), 7.50 (t, 2H), 7.34 (t, 1H), 6.90 (s, 1H), 6.84 (s, 1H), 6.35 (s, 1H), 3.52 (m, 2H), 3.39 (m, 8H), 3.18 (m, 4H), 2.90 (m, 2H), 2.02 (m, 3H), 1.42 (m, 2H)

EXAMPLE 97

(5-(1,1-Dioxo-thiomorpholin-4-yl)methyl-2-phenyl-1H-indol-7-yl)-(1-methanesulfonyl-piperidin-4-yl)-amine (5-(1,1-Dioxo-thiomorpholin-4-yl)methyl-2-phenyl-1H-indol-7-yl)-(piperidin-4-yl)methyl-amine prepared in Example 96 and methanesulfonylchloride were reacted according to the same procedure as Example 22 to give the title compound.
$^1$H-NMR (500 MHz, DMSO-$d_6$); δ 10.92 (s, 1H), 7.76 (d, 2H), 7.43 (t, 2H), 7.27 (t, 1H), 6.72 (m, 2H), 6.26 (s, 1H), 5.35 (d, 1H), 3.57 (m, 5H), 3.05 (m, 4H), 2.95 (t, 2H), 2.88 (s, 3H), 2.84 (m, 4H), 2.14 (d, 2H), 1.47 (m, 2H)

EXAMPLE 98

{4-[5-(1,1-Dioxo-thiomorpholin-4-yl)methyl-2-phenyl-1H-indol-7-yl]amino-piperidin-1-yl}-(tetrahydrofuran-2-yl)-methanone (5-(1,1-Dioxo-thiomorpholin-4-yl)methyl-2-phenyl-1H-indol-7-yl)-(piperidin-4-yl)methyl-amine prepared in Example 96 and tetrahydrofuran-2-carboxylic acid were reacted according to the same procedure as Example 92 to give the title compound.
$^1$H-NMR (500 MHz, DMSO-$d_6$); δ 10.87 (s, 1H), 7.75 (d, 2H), 7.43 (t, 2H), 7.27 (t, 1H), 6.72 (s, 2H), 6.29 (s, 1H), 5.30 (d, 1H), 4.27 (d, 1H), 3.95 (d, 1H), 3.86 (m, 1H), 3.68 (m, 4H), 3.59 (s, 2H), 3.37 (m, 1H), 3.27 (m, 1H), 3.06 (m, 4H), 2.92 (m, 1H), 2.84 (m, 4H), 2.02 (m, 4H), 1.29 (m, 2H)

EXAMPLE 99

(5-Fluoro-2-phenyl-1H-indol-7-yl)-[1-(1,1-dioxo-tetrahydrothiopyran-4-yl)-piperidin-4-yl]-amine Step A: (5-Fluoro-2-phenyl-1H-indol-7-yl)-piperidin-4-yl-amine 5-Fluoro-7-nitro-2-phenyl-1H-indole prepared in Preparation 25 and 1-BOC-piperidinone were reacted according to the same procedure as Example 90 to give the title compound.

Step B: (5-Fluoro-2-phenyl-1H-indol-7-yl)-[1-(1,1-dioxo-tetrahydrothiopyran-4-yl)-piperidin-4-yl]-amine (5-Fluoro-2-phenyl-1H-indol-7-yl)-piperidin-4-yl-amine prepared in Step A and 1,1-dioxo-tetrahydro-thiopyranone were reacted according to the same procedure as Step B of Example 1 to give the title compound.
$^1$H-NMR (400 MHz, CDCl$_3$); δ 7.66 (d, 2H), 7.44 (t, 2H), 7.33 (t, 1H), 6.74 (d, 1H), 6.72 (d, 1H), 6.26 (d, 1H), 3.39 (m, 1H), 3.22 (m, 2H), 2.92 (m, 4H), 2.57 (t, 1H), 2.33 (m, 4H), 2.28 (m, 4H), 1.53 (m, 2H)

EXAMPLE 100

N-(5-chloro-2-phenyl-1H-indol-7-yl)-N',N'-dimethyl-cyclohexane-1,4-diamine

7-Amino-5-chloro-2-phenyl-1H-indole prepared in Example 3 and 4-dimethylaminohexanone were reacted according to the same procedure as Step B of Example 1 to give the title compound.
$^1$H-NMR (500 MHz, DMSO-d6); δ 11.05 (s, 1H), 7.75 (d, J=6.7 Hz, 2H), 7.44 (t, J=7.3 Hz, 2H), 7.29 (t, J=7.3 Hz, 1H), 6.73 (m, 2H), 6.17 (m, 1H), 5.52 (m, 1H), 4.55 (m, 1H), 3.46 (m, 1H), 3.29 (m, 6H), 2.05 (m, 2H), 1.86 (m, 2H), 1.33 (m, 2H), 1.23 (m, 2H)

EXAMPLE 101

N-(5-chloro-2-phenyl-1H-indol-7-yl)-N'-methyl-cyclohexane-1,4-diamine

During the process of Example 100, the monoalkylated title compound was obtained.
$^1$H-NMR (500 MHz, DMSO-d6); δ 11.05 (s, 1H), 7.75 (d, J=6.7 Hz, 2H), 7.44 (t, J=7.3 Hz, 2H), 7.30 (t, J=7.3 Hz, 1H), 6.73 (m, 2H), 6.17 (m, 1H), 5.51 (m, 1H), 4.55 (m, 1H), 3.45 (m, 1H), 3.28 (m, 3H), 3.13 (m, 1H), 2.05 (m, 2H), 1.86 (m, 2H), 1.33 (m, 2H), 1.23 (m, 2H)

EXAMPLE 102

4-(5-Chloro-2-phenyl-1H-indol-7-yl)amino-cyclohexane-1-carboxylic acid

7-Amino-5-chloro-2-phenyl-1H-indole prepared in Example 3 and 4-oxo-cyclohexane-1-carboxylic acid methyl ester were reacted according to the same procedures as Step B of Example 1 and Example 30 sequentially to give the title compound.
$^1$H-NMR (500 MHz, DMSO-d6); δ 11.08 (m, 1H), 7.76 (d, J=6.7 Hz, 2H), 7.44 (t, J=7.3 Hz, 2H), 7.30 (t, J=7.3 Hz, 1H), 6.74 (d J=1.25 Hz, 1H), 6.72 (d, J=1.8 Hz, 1H), 6.18 (m, 1H), 5.55 (m, 1H), 3.50 (m, 1H), 3.34 (m, 1H), 2.11 (m, 1H), 1.95 (m, 2H), 1.81 (m, 1H), 1.65 (m, 1H), 1.53 (m, 2H), 1.23 (m, 1H)

EXAMPLE 103

4-(5-Methyl-2-phenyl-1H-indol-7-yl)amino-cyclohexane-1-carboxylic acid

5-Methyl-7-nitro-2-phenyl-1H-indole prepared in Preparation 24 and 4-oxo-cyclohexyl-1-carboxylic acid were reacted according to the same procedures as Examples 1 and 30 sequentially to give the title compound.
$^1$H-NMR (500 MHz, DMSO-d$_6$); δ 10.81 (brs, 1H), 7.74 (m, 2H), 7.42 (m, 2H), 7.25 (m, 1H), 6.64 (d, J=2.45 Hz, 1H), 6.53 (s, 1H), 6.05 (s, 1H), 5.17 (m, 1H), 3.50 (m, 2H), 2.24 (s, 3H), 1.95 (m, 1H), 1.81 (m, 2H), 1.64 (m, 2H), 1.57 (m, 2H)

EXAMPLE 104

4-(5-Chloro-2-phenyl-1H-indol-7-yl)amino-cyclohexane-1-carboxylic acid amide 4-(5-Chloro-2-phenyl-1H-indol-7-yl)amino-cyclohexane-1-carboxylic acid prepared in Example 102 and NH$_4$Cl were reacted according to the same procedure as Example 92 to give the title compound.
$^1$H-NMR (500 MHz, DMSO-d6); δ 11.20 (s, 1H), 7.76 (d, J=6.7 Hz, 2H), 7.44 (t, J=7.3 Hz, 2H), 7.29 (t, J=7.3 Hz, 1H), 7.21 (brs, 1H), 6.73 (m, 3H), 6.14 (m, 1H), 5.55 (m, 1H), 3.54 (m, 1H), 2.26 (m, 1H), 1.87 (m, 2H), 1.72 (m, 4H), 1.59 (m, 2H)

EXAMPLE 105

4-(5-Chloro-2-phenyl-1H-indol-7-yl)amino-cyclohexanecarboxylic acid methylamide 4-(5-Chloro-2-phenyl-1H-indol-7-yl)amino-cyclohexane-1-carboxylic acid prepared in Example 102 and methylamine (HCl salt) were reacted according to the same procedure as Example 92 to give the title compound.
$^1$H-NMR (500 MHz, DMSO-d6); δ 11.26 (s, 1H), 7.77 (d, J=6.7 Hz, 2H), 7.66 (m, 1H), 7.44 (t, J=7.3 Hz, 2H), 7.30 (t, J=7.3 Hz, 1H), 6.76 (d J=1.25 Hz, 1H), 6.72 (d, J=1.8 Hz, 1H), 6.15 (m, 1H), 3.57 (m, 1H), 2.55 (m, 3H), 2.24 (m, 1H), 1.88 (m, 2H), 1.80-1.65 (m, 4H), 1.57 (m, 2H)

EXAMPLE 106

2-(5-Fluoro-2-phenyl-1H-indol-7-yl)amino-acetic acid methyl ester

7-Nitro-5-fluoro-2-phenyl-1H-indole prepared in Preparation 27 and methyl bromoacetate were reacted according to the same procedures as Step A of Example 1 and Example 22 sequentially to give the title compound.
$^1$H-NMR (400 MHz, CDCl$_3$); δ 7.56 (d, 2H), 7.41 (t, 2H), 7.34 (t, 1H), 6.80 (d, 1H), 6.71 (s, 1H), 6.19 (d, 1H), 4.09 (s, 2H), 3.85 (s, 3H)

EXAMPLE 107

2-(5-Fluoro-2-phenyl-1H-indol-7-yl)amino-acetic acid 2-(5-Fluoro-2-phenyl-1H-indol-7-yl)amino-acetic acid methyl ester prepared in Example 106 was reacted according to the same procedure as Example 30 to give the title compound.

$^1$H-NMR (400 MHz, DMSO-d$_6$); δ 7.91 (d, 2H), 7.41 (t, 2H), 7.26 (t, 1H), 6.73 (s, 1H), 6.41 (d, 1H), 5.78 (d, 1H), 6.17 (br s, 1H), 3.48 (s, 2H)

EXAMPLE 108

2-(5-Phenoxy-2-phenyl-1H-indol-7-yl)amino-acetic acid methyl ester

7-Nitro-5-phenoxy-2-phenyl-1H-indole prepared in Preparation 27 and methyl bromoacetate were reacted according to the same procedures as Step A of Example 1 and Example 22 sequentially to give the title compound.

$^1$H-NMR (400 MHz, DMSO-d$_6$); δ 8.46 (brs, 1H), 7.66 (d, 2H), 7.44 (t, 2H), 7.35~7.28 (m, 3H), 7.09~6.99 (m, 3H), 6.80 (d, J=2.0 Hz, 1H), 6.73 (d, J=2.0 Hz, 1H), 6.24 (d, J=2.0 Hz, 1H), 5.38 (m, 1H), 4.47 (brs, 1H), 4.04 (s, 2H), 3.82 (s, 3H).

EXAMPLE 109

2-[(5-Phenoxy-2-phenyl-1H-indol-7-yl)amino]-acetic acid (5-Phenoxy-2-phenyl-1H-indol-7-yl)amino-acetic acid methyl ester prepared in Example 108 was reacted according to the same procedure as Example 30 to give the title compound.

$^1$H-NMR (500 MHz, MeOH-d4); δ 7.76 (d, J=7.3 Hz, 2H), 7.39 (t, J=7.3 Hz, 2H), 7.25 (m, 3H), 6.96 (t, J=7.3 Hz, 1H), 6.90 (d, J=7.3 Hz, 2H), 6.68 (m, 1H), 6.53 (d, J=1.85 Hz, 1H), 6.00 (d, J=1.85 Hz, 1H), 3.96 (s, 2H)

EXAMPLE 110

2[(5-Phenoxy-2-phenyl-1H-indol-7-yl)amino]-propionic acid methyl ester

2-Phenyl-5-phenoxy-7-nitro-1H-indole prepared in Preparation 27 and methyl 2-bromopropionic acid ester were reacted according to the same procedures as Step A of Example 1 and Example 22 sequentially to give the title compound.

$^1$H-NMR (500 MHz, MeOH-d4); δ 8.56 (brs, 1H), 7.66 (d, 2H), 7.43 (t, 2H), 7.32~7.26 (m, 3H), 7.09~6.61 (m, 3H), 6.77 (d, J=1.8 Hz, 1H), 6.71 (d, J=1.8 Hz, 1H), 6.23 (d, J=1.8 Hz, 1H), 5.33 (m, 1H), 4.23 (q, 1H), 3.73 (s, 3H) 1.53 (d, 3H).

EXAMPLE 111

2-(5-Phenoxy-2-phenyl-1H-indol-7-yl)amino-propionic acid 2-(5-Phenoxy-2-phenyl-1H-indol-7-yl)amino-propionic acid methyl ester prepared in Example 110 was reacted according to the same procedure as Example 30 to give the title compound.

$^1$H-NMR (500 MHz, MeOH-d4); δ 7.76 (d, J=7.3 Hz, 2H), 7.40 (t, J=7.3 Hz, 2H), 7.24 (m, 3H), 6.94 (t, J=7.3 Hz, 1H), 6.89 (d, J=7.3 Hz, 2H), 6.68 (m, 1H), 6.52 (d, J=1.85 Hz, 1H), 4.57 (m, 1H), 1.55 (m, 3H)

EXAMPLE 112

2-(5-Chloro-2-phenyl-1H-indol-7-yl)amino-propionic acid

7-Amino-5-chloro-2-phenyl-1H-indole prepared in Example 3 and methyl 2-bromopropionic acid ester were reacted according to the same procedures as Examples 22 and 30 sequentially to give the title compound.

$^1$H-NMR (400 MHz, CDCl$_3$); δ 8.62 (br s, 1H), 7.55 (d, J=8 Hz, 2H), 7.38 (t, 2H), 7.30 (t, 1H), 7.00 (s, 1H), 6.60 (s, 1H), 6.31 (s, 1H), 4.47 (br s, 1H), 4.27 (m, 1H), 1.58 (d, J=8 Hz, 3H)

EXAMPLE 113

(5-Chloro-2-phenyl-1H-indol-7-yl)-pyridin-2-yl-amine

7-Amino-5-chloro-2-phenyl-1H-indole (200 mg, 0.82 mmol) prepared in Example 3 was dissolved in toluene (30 mL). 2-Bromopyridine (182 mg, 1.15 mmol), Pd$_2$(dba)$_3$, Xantphos (42 mg, 0.07 mmol) and Na$_2$CO$_3$ were added thereto. The mixture was degassed, and stirred for 12 h at 100° C. After completion of the reaction, the reaction mixture was filtered through a cellite. The solvent was removed under reduced pressure, and the residue was purified by column chromatography (eluent: EtOAc/n-Hex=1/3) to give the title compound (25 mg, Yield 13%).

$^1$H-NMR (400 MHz, CDCl$_3$); δ 8.06 (m, 1H), 7.68 (d, J=7.2 Hz, 2H), 7.50 (t, 1H), 7.37 (m, 3H), 7.29 (d, J=8 Hz, 1H), 6.90 (d, J=2 Hz, 1H), 6.74 (m, 3H)

EXAMPLE 114

(5-Chloro-2-phenyl-1H-indol-7-yl)-5-methyl-pyridin-2-yl-amine

7-Amino-5-chloro-2-phenyl-1H-indole prepared in Example 3 and 2-bromo-5-methyl-pyridine were reacted according to the same procedure as Example 113 to give the title compound.

$^1$H-NMR (400 MHz, CDCl$_3$); δ 10.64 (s, 1H), 7.75 (d, J=8 Hz, 2H), 7.47 (m, 4H), 7.36 (m, 1H), 6.91 (s, 1H), 6.80 (s, 1H), 6.67 (d, J=8 Hz, 1H), 6.59 (d, J=8 Hz, 1H), 2.47 (s, 3H)

EXAMPLE 115

(5-Chloro-3-phenyl-1H-indol-7-yl)-(5-methyl-pyridin-2-yl)-amine

5-Chloro-3-phenyl-7-nitro-1H-indole prepared in Preparation 41 was reacted according to the same procedures as Step A of Example 1 and Example 113 to give the title compound.

EXAMPLE 116

(2S)-1-(7-cyclopentylamino-2-phenyl-1H-indole-5-carbonyl)-pyrrolidine-2-carboxylic acid methylester 7-Cyclopentylamino-2-phenyl-1H-indole-5-carboxylic acid prepared in Example 30 and (2S)-Pro-OMe were reacted according to the same procedure as Example 92 to give the title compound.

¹H-NMR (500 MHz, CDCl₃); δ 9.76 (brs, 1H), 7.67 (d, 2H), 7.37 (t, 2H), 7.26~7.22 (m, 2H), 6.72 (d, 1H), 6.59 (d, 1H), 4.68 (m, 1H), 3.81 (m, 3H), 3.65 (s, 3H), 2.31 (m, 1H), 2.01 (m, 3H), 1.81 (m, 3H), 1.56 (m, 2H), 1.43 (m, 2H), 1.33 (m, 2H)

EXAMPLE 117

(2S)-1-(7-cyclopentylamino-2-phenyl-1H-indole-5-carbonyl)-pyrrolidine-2-carboxylic acid (2S)-1-(7-cyclopentylamino-2-phenyl-1H-indole-5-carbonyl)-pyrrolidine-2-carboxylic acid methylester prepared in Example 116 was reacted according to the same procedure as Example 30 to give the title compound.

¹H-NMR (500 MHz, MeOH-d4); δ 7.75 (d, J=7.3 Hz, 2H), 7.39 (t, J=7.3 Hz, 2H), 7.26 (t, J=7.3 Hz, 1H), 7.15 (m, 1H), 6.78 (m, 1H), 6.55 (m, 1H), 4.58 (m, 1H), 3.97 (m, 1H), 3.69 (m, 2H), 2.37 (m, 1H), 2.08 (m, 2H), 1.98 (m, 2H), 1.82 (m, 3H), 1.65 (m, 4H)

EXAMPLE 118

(2S)-1-[2-phenyl-7-(tetrahydropyran-4-yl)amino-1H-indole-5-carbonyl]-pyrrolidine-2-carboxylic acid 2-Phenyl-7-nitro-1H-indole-5-carboxylic acid prepared in Preparation 28, (2S)-Pro-OMe and tetrahydropyran-4-one were reacted according to the same procedures as Examples 92, 1 and 30 sequentially to give the title compound.

¹H-NMR (500 MHz, MeOH-d4); δ 7.75 (d, J=7.3 Hz, 2H), 7.39 (t, J=7.3 Hz, 2H), 7.27 (t, J=7.3 Hz, 1H), 7.17 (m, 1H), 6.79 (m, 1H), 6.62 (m, 1H), 4.56 (m, 1H), 4.00 (m, 2H), 3.71 (m, 2H), 3.66-3.55 (m, 3H), 2.36 (m, 1H), 2.12 (m, 2H), 1.99 (m, 2H), 1.84 (m, 1H), 1.55 (m, 2H)

EXAMPLE 119

2-(7-Cyclopentylamino-2-phenyl-1H-indol-5-yl]-1-pyrrolidin-1-yl-ethanone

2-[7-(Cyclopentyl)amino-2-phenyl-1H-indol-5-yl]-acetic acid prepared in Example 33 and pyrrolidine were reacted according to the same procedure as Example 92 to give the title compound.

¹H-NMR (400 MHz, CDCl₃); δ 9.92 (br s, 1H), 7.69 (d, 1H), 7.32 (t, 1H), 7.20 (t, 1H), 6.80 (s, 1H), 6.63 (d, 1H), 6.22 (d, 1H), 3.69 (s, 2H), 3.59 (m, 1H), 3.46 (m, 4H), 1.91 (m, 4H), 1.77 (m, 2H), 1.63 (m, 2H), 1.43 (m, 4H)

EXAMPLE 120

Cyclopentyl-[2-phenyl-5-(2-pyrrolidin-1-yl-ethyl)-1H-indol-7-yl]-amine

2-[7-Cyclopentylamino-2-phenyl-1H-indol-5-yl]-ethanol prepared in Example 32 and pyrrolidine were reacted according to the same procedures as Steps A and B of Example 36 to give the title compound.

¹H-NMR (500 MHz, MeOH-d4); δ 7.75 (d, J=7.3 Hz, 2H), 7.38 (t, J=7.3 Hz, 2H), 7.24 (t, J=7.3 Hz, 1H), 6.76 (m, 1H), 6.67 (m, 1H), 3.98 (m, 1H), 3.07 (m, 2H), 2.92 (m, 6H), 2.08 (m, 2H), 1.91 (m, 4H), 1.80 (m, 2H), 1.66 (m, 4H)

EXAMPLE 121

2-[(R)-2-(7-cyclopentylamino-2-phenyl-1H-indol-5-yl)-4,5-dihydro-thiazol-4-yl]-acetic acid Step A: (R)-4-(4-methoxy-benzylsulfanyl)-3-[(7-nitro-2-phenyl-1H-indole-5-carbonyl)-amino]-butyric acid methyl ester 2-Phenyl-7-nitro-1H-indole-5-carboxylic acid prepared in Preparation 28 and (R)-3-amino-4-(4-methoxy-benzylsulfanyl)-butyric acid methyl ester hydrochloride prepared in Preparation 47 were reacted according to the same procedure as Example 92 to give the title compound.

Step B: 2-[(R)-2-(7-nitro-2-phenyl-1H-indol-5-yl)-4,5-dihydro-thiazol-4-yl]-acetic acid methyl ester (R)-4-(4-methoxy-benzylsulfanyl)-3-[(7-nitro-2-phenyl-1H-indole-5-carbonyl)-amino]-butyric acid methyl ester (533 mg, 1 mmol) prepared in Step A was dissolved in DCM (10 mL). Phosphorus pentachloride (406 mg, 2 mmol) was added thereto, and the mixture was stirred for 5 h at room temperature. The reaction was quenched by saturated aqueous sodium bicarbonate solution. The reaction mixture was extracted with ethyl acetate. The extract was dried over anhydrous magnesium sulfate, filtered, and distilled under reduced pressure. The residue was purified by column chromatography to give the title compound (240 mg, Yield 60%).

Step C: 2-[(R)-2-(7-cyclopentylamino-2-phenyl-1H-indol-5-yl)-4,5-dihydro-thiazol-4-yl]-acetic acid 2-[(R)-2-(7-nitro-2-phenyl-1H-indol-5-yl)-4,5-dihydro-thiazol-4-yl]-acetic acid methyl ester prepared in Step B and cyclopentanone were reacted according to the same procedures as Examples 1 and 30 to give the title compound.

¹H-NMR (400 MHz, DMSO-d₆); δ 11.81 (s, 1H), 7.92 (m, 2H), 7.60 (m, 2H), 7.50 (m, 2H), 7.34 (m, 1H), 6.83 (m, 1H), 4.99 (m, 1H), 3.95 (m, 1H), 3.70 (m, 2H), 2.87 (m, 1H), 2.71 (m, 1H), 2.08 (m, 2H), 1.77 (m, 2H), 1.64 (m, 4H)

EXAMPLE 122

2-[(R)-2-(2-phenyl-7-(tetrahydropyran-4-yl)methylamino-1H-indol-5-yl)-4,5-dihydro-thiazol-4-yl]-acetic acid 2-[(R)-2-(7-nitro-2-phenyl-1H-indol-5-yl)-4,5-dihydro-thiazol-4-yl]-acetic acid methyl ester prepared in Step B of Example 121 and tetrahydropyran-4-one were reacted according to the same procedures as Examples 1 and 30 sequentially to give the title compound.

¹H-NMR (400 MHz, DMSO-d₆); δ 11.79 (m, 1H), 7.91 (m, 2H), 7.51 (m, 2H), 7.39 (m, 2H), 7.01 (m, 1H), 6.80 (m, 1H), 4.96 (m, 1H), 3.93 (m, 1H), 3.33 (m, 3H), 3.15 (m, 2H), 2.87 (m, 2H), 2.75 (m, 1H), 1.95 (m, 1H), 1.79 (m, 2H), 1.36 (m, 2H)

EXAMPLE 123

3-(7-Cyclopentylamino-5-chloro-1H-indol-2-yl)-benzoic acid methyl ester

Step A: 3-(5-Chloro-7-amino-1H-indol-2-yl)benzoic acid methyl ester

3-(5-Chloro-7-nitro-1H-indol-2-yl)benzoic acid prepared in Preparation 32 was reacted according to the same procedure as Example 28 to give the title compound.

Step B: 3-(7-Cyclopentylamino-5-chloro-1H-indol-2-yl)-benzoic acid methylester

3-(5-Chloro-7-amino-1H-indol-2-yl)benzoic acid methyl ester prepared in Step A was reacted according to the same procedure as Example 1 to give the title compound.
$^1$H-NMR (400 MHz, CDCl$_3$); δ 8.78 (br s, 1H), 8.31 (s, 1H), 7.94 (m, 1H), 7.85 (m, 1H), 7.46 (t, 1H), 7.03 (s, 1H), 6.76 (s, 1H), 6.47 (s, 1H), 3.93 (m, 4H), 2.16~1.63 (m, 3H)

EXAMPLE 124

3-(7-Cyclopentylamino-5-chloro-1H-indol-2-yl)-benzoic acid 3-(7-Cyclopentylamino-5-chloro-1H-indol-2-yl)-benzoic acid methyl ester prepared in Example 123 was reacted according to the same procedure as Example 30 to give the title compound.
$^1$H-NMR (400 MHz, DMSO-d$_6$); δ 13.20 (br s, 1H), 11.21 (br s, 1H), 8.37 (s, 1H), 8.06 (d, 1H), 7.91 (d, 1H), 7.60 (t, 1H), 6.85 (d, 1H), 6.82 (d, 1H), 6.20 (d, 1H), 5.80 (br s, 1H), 3.88 (m, 1H), 2.51~1.58 (m, 8H)

EXAMPLE 125

[3-(5-Chloro-7-cyclopentylamino-1H-indol-2-yl)-phenyl]-methanol 3-(7-Cyclopentylamino-5-chloro-1H-indol-2-yl)-benzoic acid methyl ester prepared in Example 123 was reacted according to the same procedure as Example 32 to give the title compound.

EXAMPLEs 126 to 146

Indole derivatives prepared in Preparations 31 to 37 were reacted according to a method selected from Examples 123 to 125 to synthesize the Example Compounds in the following table.

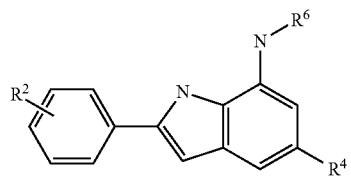

| Example | R$^2$ | R$^4$ | R$^6$ | $^1$H-NMR |
|---|---|---|---|---|
| 126 | m-CH$_2$OH | Cl | THP-4-yl | (400 MHz, DMSO-d$_6$); δ 11.08 (s, 1H), 7.76 (s, 1H), 7.67 (d, J = 8 Hz, 1H), 7.43 (t, 1H), 7.27 (d, J = 8 Hz, 1H), 6.81 (s, 1H), 6.75 (s, 1H), 6.29 (s, 1H), 5.74 (br s, 1H), 4.59 (s, 2H), 3.92 (d, J = 8 Hz, 2H), 3.65 (m, 1H), 3.50 (t, 2H), 2.03 (d, J-12 Hz, 2H), 1.52 (m, 2H) |
| 127 | m-CH$_2$CO$_2$H | Cl | (THP-4-yl)methyl | (400 MHz, DMSO-d$_6$, Na salt); δ 12.51 (s, 1H), 7.86 (s, 1H), 7.56 (d, J = 8 Hz, 1H), 7.24 (t, 1H), 7.12 (d, J = 8 Hz, 1H), 6.76 (s, 1H), 6.72 (s, 1H), 6.65 (s, 1H), 6.07 (s, 1H), 3.87 (dd, 2H), 3.41 (s, 2H), 3.28 (m, 2H), 3.04 (m, 2H), 1.94 (m, 1H), 1.76 (d, J = 12 Hz, 2H), 1.32 (m, 2H) |
| 128 | m-CH$_2$CO$_2$H | Cl | c-Pen | $^1$H-NMR (400 MHz, DMSO-d$_6$, Na salt); δ 12.09 (s, 1H), 7.76 (s, 1H), 7.53 (d, J = 8 Hz, 1H), 7.26 (t, 1H), 7.10 (d, J = 8 Hz, 1H), 6.72 (s, 1H), 6.65 (s, 1H), 6.38 (m, 1H), 6.09 (s, 1H), 3.85 (m, 1H), 3.33 (m, 2H), 1.98 (m, 2H), 1.76 (m, 2H), 1.61 (m, 4H) |
| 129 | m-CH$_2$CO$_2$H | Cl | THP-4-yl | (400 MHz, DMSO-d$_6$, Na salt); δ 11.90 (s, 1H), 7.75 (s, 1H), 7.53 (d, J = 8 Hz, 1H), 7.25 (t, 1H), 7.12 (d, J = 8 Hz, 1H), 6.74 (s, 1H), 6.66 (s, 1H), 6.30 (m, 1H), 6.20 (s, 1H), 3.92 (d, J = 12 Hz, 2H), 3.52 (m, 1H), 3.33 (m 2H), 2.00 (d, J = 12 Hz, 2H), 1.56 (m, 2H) |
| 130 | m-CH$_2$CO$_2$Me | Cl | (THP-4-yl)methyl | (400 MHz, CDCl$_3$); δ 8.38 (s, 1H), 7.55 (m, 2H), 7.36 (t, 1H), 7.22 (d, J = 8 hz, 1H), 7.05 (s, 1H), 6.70 (s, 1H), 6.43 (s, 1H), 4.03 (dd, 2H), 3.79 (m, 1H), 3.73 (s, 3H), 3.69 (s, 2H), 3.48 (t, 2H), 3.17 (d, J = 4 Hz, 2H), 1.98 (m, 1H), 1.80 (d, J = 8 Hz, 2H), 1.48 (m, 2H) |
| 131 | m-CH$_2$CO$_2$Me | Cl | c-Pen | (400 MHz, CDCl$_3$); δ 8.78 (br s, 1H), 7.55 (s, 1H), 7.50 (d, J = 8 Hz, 1H), 7.28 (t, 1H), 7.17 (d, J = 8 Hz, 1H), 6.99 (s, 1H), 6.64 (s, 1H), 6.45 (s, 1H), 3.91 (m, 1H), 3.73 (s, 3H), 3.68 (s, 2H), 2.10 (m, 2H), 1.87 (m, 2H), 1.63 (m, 4H) |

-continued

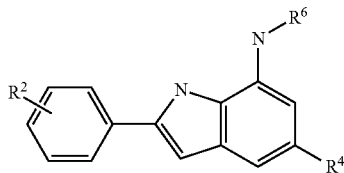

| Example | R² | R⁴ | R⁶ | ¹H-NMR |
|---|---|---|---|---|
| 132 | m-CH₂CO₂Me | Cl | THP-4-yl | (400 MHz, CDCl₃); δ 8.83 (br s, 1H), 7.54 (s, 1H), 7.53 (s, 1H), 7.34 (t, 1H), 7.20 (m, 1H), 7.05 (s, 1H), 6.67 (s, 1H), 6.44 (s, 1H), 4.06 (d, J-12 Hz, 2H), 3.74 (s, 3H), 3.71 (s, 2H), 3.57 (t, 2H), 3.56 (m, 1H), 2.14 (d, J = 12 Hz, 2H), 1.64 (m, 2H) |
| 133 | o-CH₂OH | Cl | c-Pen | (400 MHz, CDCl₃); δ 11.37 (brs, 1H), 7.69 (d, J = 8 Hz, 1H), 7.47 (m, 2H), 7.42 (m, 2H), 7.21 (s, 1H), 6.69 (s, 1H), 4.78 (s, 2H), 3.97 (m, 1H), 1.96 (m, 4H), 1.86 (m, 2H), 1.56 (m, 2H) |
| 134 | o-CO₂H | Cl | c-Pen | ¹H-NMR (400 MHz, DMSO-d₆); δ 11.57 (brs, 1H), 7.71 (m, 2H), 7.61 (m, 2H), 7.50 (m, 1H), 7.07 (s, 1H), 6.53 (s, 1H), 6.48 (s, 1H), 3.97 (m, 1H), 2.00 (m, 2H), 1.76 (m, 2H), 1.67 (m, 4H) |
| 135 | o-CO₂Me | Cl | c-Pen | ¹H-NMR (400 MHz, CDCl₃); δ 9.81 (brs, 1H), 7.71 (d, J = 4 Hz, 1H), 7.59 (d, J = 4 Hz, 1H), 7.43 (t, 1H), 7.30 (t, 1H), 6.97 (s, 1H), 6.50 (d, J = 2 Hz, 1H), 6.36 (d, J = 2 Hz, 1H), 3.89 (s, 3H), 3.86 (m, 1H), 2.12 (m, 2H), 1.77 (m, 2H), 1.67 (m, 2H), 1.60 (m, 2H) |
| 136 | p-CH₂OH | Cl | c-Pen | (400 MHz, DMSO-d₆); δ11.04 (brs, 1H), 7.75 (d, J = 8 Hz, 2H), 7.42 (d, J = 8 Hz, 2H), 6.78 (s, 1H), 6.73 (s, 1H), 6.17 (s, 1H), 5.71 (d, J = 3 Hz, 1H), 5.23 (t, 1H), 4.54 (d, J = 4 Hz, 1H), 4.02 (m, 1H), 2.02 (m, 2H), 1.75 (m, 2H), 1.63 (m, 2H), 1.55 (m, 2H) |
| 137 | p-(CH₂)₂OH | Cl | THP-4-yl | ¹H-NMR (400 MHz, DMSO-d₆); δ 11.27 (s, 1H), 7.75 (d, J = 4 Hz, 2H), 7.32 (d, J-8 Hz, 2H), 6.84 (m, 1H), 6.73 (s, 1H), 6.33 (m, 2H), 3.88 (d, 2H), 3.64 (m, 3H), 3.38 (t, 2H), 2.76 (t, 2H), 1.99 (s, 2H), 1.53 (m, 2H) |
| 138 | p-CO₂H | Cl | c-Pen | ¹H-NMR (400 MHz, DMSO-d₆); δ 11.59 (brs, 1H), 8.01 (m, 4H), 6.94 (d, J = 12 Hz, 2H), 6.31 (s, 1H), 3.91 (m, 1H), 2.01 (m, 2H), 1.77 (m, 2H), 1.62 (m, 4H) |
| 139 | p-CH₂CO₂H | Cl | (THP-4-yl)methyl | (400 MHz, DMSO-d₆, Na salt); δ 12.83 (s, 1H), 7.76 (d, J = 8 Hz, 2H), 7.35 (d, J = 8 Hz, 2H), 7.00 (s, 1H), 6.71 (s, 1H), 6.59 (s, 1H), 6.04 (s, 1H), 3.90 (d, 2H), 3.35 (s, 2H), 3.33 (m, 2H), 3.03 (m, 2H), 1.98 (m, 1H), 1.80 (d, J = 12 Hz, 2H), 1.32 (m, 2H) |
| 140 | p-CH₂CO₂H | Cl | c-Pen | (400 MHz, DMSO-d₆, Na salt); δ 12.55 (s, 1H), 7.79 (d, J = 8 Hz, 2H), 7.30 (d, J = 8 Hz, 2H), 6.81 (s, 1H), 6.60 (s, 2H), 6.07 (s, 1H), 3.83 (m, 1H), 3.31 (s, 2H), 1.98 (m, 2H), 1.77 (m, 2H), 1.62 (m, 4H) |
| 141 | p-CH₂CO₂H | Cl | THP-4-yl | ¹H-NMR (400 MHz, DMSO-d₆, Na salt); δ 12.53 (s, 1H), 7.70 (d, J = 8 Hz, 2H), 7.30 (d, J = 8 Hz, 2H), 6.72 (s, 1H), 6.60 (s, 2H), 6.19 (s, 1H), 3.90 (d, J = 12 Hz, 2H), 3.60 (m, 1H), 3.48 (m, 2H), 3.35 (s, 2H), 1.96 (d, J = 12 Hz, 2H), 1.59 (m, 2H) |
| 142 | p-CO₂Me | Cl | c-Pen | (400 MHz, DMSO-d₆); δ 11.25(s, 1H), 8.07 (d, J = 8 Hz, 2H), 7.94 (d, J = 8 Hz, 2H), 6.95 (s, 1H), 6.84 (s, 1H), 6.22 (s, 1H), 5.64 (d, J = 8 Hz, 1H), 3.88 (s, 3H), 2.07 (m, 2H), 1.75 (m, 2H), 1.67 (m, 2H), 1.57 (m, 2H) |
| 143 | p-CO₂Me | Me | c-Pen | (400 MHz, CDCl₃); 8.18 (br s, 1H), 8.06 (d, J = 8 Hz, 2H), 7.70 (d, J =12 Hz, 2H), 6.91 (s, 1H), 6.84 (s, 1H), 6.40(s, 1H), 3.97 (m, 1H), 3.93 (s, 3H), 2.42 (s, 3H), 2.13(m, 2H), 1.79 (m, 2H), 1.68 (m, 2H), 1.61 (m, 2H) |
| 144 | p-CH₂CO₂Me | Cl | (THP-4-yl)methyl | (400 MHz, CDCl₃); δ 8.40 (br s, 1H), 7.70 (d, J = 8 Hz, 2H), 7.32 (d, J = 8 Hz, 2H), 7.05 (s, 1H), 6.67 (s, 1H), 6.43 (s, 1H), 3.95 (d, 2H), 3.73 (s, 3H), 3.67 (S, 2h), 3.44 (T, 2H), 3.16 (D, j = 8 Hz, 2H), 1.98 (m, 1H), 1.79 (d, J = 12 Hz, 2H), 1.42 (m, 2H) |
| 145 | p-CH₂CO₂Me | Cl | c-Pen | (400 MHz, CDCl₃); δ 8.34 (br s, 1H), 7.48 (d, J = 8 Hz, 2H), 7.25 (d, J = 8 Hz, 2H), 7.02 (s, 1H), 6.64 (s, 1H), 6.45 (s, 1H), 3.94 (m, 1H), 3.74 (s, 3H), 3.66 (s, 2H), 2.11 (m, 2H), 1.81 (m, 2H), 1.68 (m, 2H), 1.59 (m, 2H) |
| 146 | p-CH₂CO₂Me | Cl | THP-4-yl | (400 MHz, CDCl₃); δ 8.74 (br s, 1H), 7.53 (d, J = 8 hz, 2H), 7.35 (d, J = 8 Hz, 2H), 7.05 (s, 1H), 6.46 (s, 1H), 6.44 (s, 1H), 3.94 (d, 2H), 3.75 (m, 1H), 3.72 (s, 3H), 3.67 (s, 2H), 3.61 (m, 2H), 2.13 (d, j + 8 Hz, 2H), 1.58 (m, 2H) |

EXAMPLE 147

[5-Chloro-2-(3-dimethylaminomethylphenyl)-1H-indol-7-yl]-(tetrahydropyran-4-yl)-amine

[3-(5-Chloro-7-(tetrahydropyran-4-yl)-phenyl)]methanol prepared in Example 126 and dimethylamine (HCl salt) were reacted according to the same procedure as Example 36 to give the title compound.

$^1$H-NMR (400 MHz, CDCl$_3$); δ 10.77 (br s, 1H), 7.95 (br s, 1H), 7.75 (d, J=8 Hz, 1H), 7.37 (t, 1H), 7.06 (m, 1H), 6.94 (s, 1H), 6.71 (s, 1H), 6.36 (s, 1H), 4.05 (d, J=12 Hz, 2H), 3.85 (m, 1H), 3.84 (s, 2H), 3.66 (m, 4H), 3.56 (t, 2H), 2.74 (m, 4H), 2.11 (m, 2H), 2.08 (s, 3H), 1.62 (m, 2H)

EXAMPLE 148

[5-Chloro-2-(3-morpholin-4-ylmethylphenyl)-1H-indol-7-yl]-(tetrahydropyran-4-yl)-amine

[3-(5-Chloro-7-(tetrahydropyran-4-yl)-phenyl)]methanol prepared in Example 126 and morpholine were reacted according to the same procedure as Example 36 to give the title compound.

$^1$H-NMR (400 MHz, DMSO-d$_6$); δ 11.12 (s, 1H), 7.77 (m, 2H), 7.43 (t, 1H), 7.28 (d, J=8 Hz, 1H), 6.80 (s, 1H), 6.76 (s, 1H), 6.31 (s, 1H), 5.73 (d, J=8 Hz, 1H), 3.94 (d, J=12 Hz, 2H), 3.64 (m, 1H), 3.59 (m, 4H), 3.53 (s, 2H), 3.48 (m, 2H), 2.39 (m, 4H), 2.02 (d, J=12 Hz, 2H), 1.48 (m, 2H)

EXAMPLE 149

[5-Chloro-2-(3-pyrrolidin-4-ylmethylphenyl)-1H-indol-7-yl]-(tetrahydropyran-4-yl)-amine

[3-(5-Chloro-7-(tetrahydropyran-4-yl)-phenyl)]methanol prepared in Example 126 and 1-BOC-piperazine were reacted according to the same procedures as Examples 36 and 82 to give the title compound.

$^1$H-NMR (400 MHz, CDCl$_3$); δ 11.18 (s, 1H), 8.26 (s, 1H), 7.82 (d, J=8 Hz, 1H), 7.37 (t, 1H), 7.02 (d, J=8 Hz, 1H), 6.91 (s, 1H), 6.71 (s, 1H), 6.33 (s, 1H), 5.65 (m, 1H), 4.15 (m, 2H), 4.09 (s, 2H), 3.63 (m, 2H), 3.56 (t, 2H), 2.14 (m, 4H), 2.09 (m, 2H), 1.79 (m, 2H)

EXAMPLE 150

1-{4-[3-(5-Chloro-7-tetrahydropyran-4-ylamino-1H-indol-2-yl)-benzyl]-piperazin-1-yl}-ethanone

[3-(5-Chloro-7-(tetrahydropyran-4-yl)-phenyl)]-methanol prepared in Example 126 and 1-acetyl-piperazine were reacted according to the same procedure as Example 36 to give the title compound.

$^1$H-NMR (400 MHz, CDCl$_3$); δ 10.77 (br, 1H), 7.95 (s, 1H), 7.74 (d, J=8 Hz, 1H), 7.59 (t, 1H), 7.06 (d, J=8 Hz, 1H), 6.94 (s, 1H), 6.71 (s, 1H), 6.36 (s, 1H), 4.06 (d, 2H), 4.03 (m, 1H), 3.82 (s, 2H), 3.66 (m, 4H), 3.53 (t, 2H), 2.74 (m, 4H), 2.08 (s, 3H), 2.04~2.11 (m, 2H), 1.64 (m, 2H).

EXAMPLE 151

{5-Chloro-2-[3-(2-oxo-piperazin-4-yl)ethylphenyl]-1H-indol-7-yl}-(tetrahydropyran-4-yl)-amine 2-[3-(7-Tetrahydropyran-4-ylamino-5-chloro-1H-indol-2-yl)-phenyl]-acetic acid methyl ester prepared in Example 132 and 2-oxo-piperazine were reacted according to the same procedures as Example 32 and Steps A and B of Example 36 sequentially to give the title compound.

$^1$H-NMR (400 MHz, DMSO-d$_6$); δ 11.04 (s, 1H), 7.71 (d, J=8 Hz, 2H), 7.35 (d, J=8 Hz, 2H), 6.79 (s, 1H), 6.72 (s, 1H), 6.28 (s, 1H), 5.62 (d, J=8 Hz, 1H), 3.93 (d, J=12 Hz, 2H), 3.65 (m, 1H), 3.50 (t, 2H), 3.15 (s, 2H), 3.00 (s, 2H), 2.79 (m, 2H), 2.63 (m, 4H), 2.03 (m, 2H), 1.47 (m, 2H)

EXAMPLE 152

{5-Chloro-2-[3-(1,1-dioxo-thiomorpholin-4-yl)ethylphenyl]-1H-indol-7-yl}-(tetrahydropyran-4-yl)-amine 2-[3-(7-Tetrahydropyran-4-ylamino-5-chloro-1H-indol-2-yl)-phenyl]-acetic acid methyl ester prepared in Example 132 and 1,1-dioxo-thiomorpholine were reacted according to the same procedures as Example 32 and Steps A and B of Example 36 sequentially to give the title compound.

$^1$H-NMR (400 MHz, DMSO-d$_6$); δ 7.70 (d, 2H), 7.34 (d, 2H), 6.79 (s, 1H), 6.72 (s, 1H), 6.28 (s, 1H), 3.91 (d, 2H), 3.65 (m, 1H), 3.53 (t, 2H), 3.16 (d, 4H), 3.00 (d, 4H), 2.77 (br s, 4H), 2.02 (d, 2H), 1.45 (d, 2H)

EXAMPLEs 153 to 161

Indole and indazole derivatives prepared in Preparations 44, 48 and 49 were reacted according to the same procedure as Example 1 to synthesize the Example Compounds in the following table.

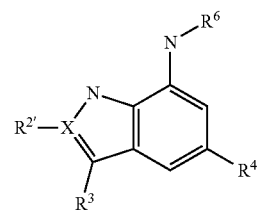

| Example | X | R$^{2'}$ | R$^3$ | R$^4$ | R$^6$ | $^1$H-NMR (400 MHz, CDCl$_3$); |
|---|---|---|---|---|---|---|
| 153 | N | — | H | H | c-Pen | δ 8.03 (s, 1H), 7.11 (d, J = 8 Hz, 1H), 7.05 (t, 1H), 6.55 (d, J = 8 Hz, 1H), 3.97 (m, 1H), 2.06 (m, 2H), 1.72 (m, 2H), 1.62 (m, 2H), 1.52 (m, 2H) |
| 154 | N | — | H | H | THP-4-yl | δ 8.05 (s, 1H), 7.15 (d, J = 8 Hz, 1H), 7.04 (t, 1H), 6.55 (d, J = 8 Hz, 1H), 4.03 (m, 2H), 3.75 (m, 1H), 3.57 (t, 2H), 2.10 (m, 2H), 1.51 (m, 2H) |

-continued

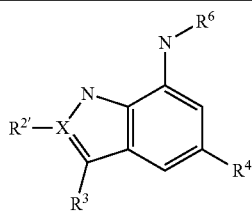

| Example | X | R²' | R³ | R⁴ | R⁶ | ¹H-NMR (400 MHz, CDCl₃); |
|---|---|---|---|---|---|---|
| 155 | N | — | H | Me | c-Pen | δ 7.89 (s, 1H), 6.83 (s, 1H), 6.32 (s, 1H), 3.87 (m, 1H), 2.39 (s, 3H), 1.96 (m, 2H), 1.60 (m, 4H), 1.44 (m, 2H) |
| 156 | N | — | H | Me | THP-4-yl | δ 7.92 (s, 1H), 6.85 (s, 1H), 6.32 (s, 1H), 3.97 (m, 2H), 3.65 (m, 1H), 3.54 (t, 2H), 2.39 (s, 3H), 2.04 (d, J = 12 Hz, 2H), 1.46 (m, 2H) |
| 157 | N | — | p-MeO—Ph— | H | c-Pen | δ 7.83 (d, J = 12 Hz, 2H), 7.31 (d, J = 8 Hz, 1H), 7.10 (t, 1H), 7.00 (dd, 2H), 6.53 (d, J = 8 Hz, 1H), 3.91 (m, 1H), 3.86 (s, 1H), 2.03 (m, 2H), 1.69 (m, 2H), 1.59 (m, 2H), 1.25 (m, 2H) |
| 158 | N | — | p-MeO—Ph— | H | THP-4-yl | δ 7.78 (d, J = 12 Hz, 2H), 7.24 (d, J = 8 Hz, 1H), 7.06 (t, 1H), 6.98 (d, J = 8 Hz, 2H), 6.45 (d, J = 8 Hz, 1H), 3.93 (m, 2H), 3.86 (s, 1H), 3.46 (t, 2H), 3.44 (m, 1H), 1.92 (d, J = 12 Hz, 2H), 1.39 (m, 2H) |
| 159 | N | — | p-MeO—Ph— | H | (THP-4-yl)methyl | δ 7.78 (d, J = 8 Hz, 2H), 7.29 (d, J = 8 Hz, 1H), 7.07 (t, 1H), 6.97 (d, J = 8 Hz, 2H), 6.45 (d, J = 8 Hz, 1H), 3.89 (m, 2H), 3.86 (s, 1H), 3.24 (t, 2H), 3.04 (d, J = 8 Hz, 2H), 1.73 (m, 1H), 1.57 (d, J = 12 Hz, 2H), 1.30 (m, 2H) |
| 160 | C | (Me)₃Si— | Ph | ![thiomorpholine dioxide] | THP-4-yl | δ 8.00 (br s, 1H), 7.43 (m, 4H), 7.36 (m, 1H), 6.92 (s, 1H), 6.55 (s, 1H), 4.08 (d, J = 12 Hz, 2H), 3.67 (m, 1H), 3.66 (s, 2H), 3.60 (t, 2H), 3.01 (d, 8H), 2.13 (d, J = 12 Hz, 2H), 1.64 (m, 2H) |
| 161 | C | H | Ph | ![thiomorpholine dioxide] | THP-4-yl | δ 8.53 (br s, 1H), 7.62 (d, 2H), 7.45 (t, 3H), 7.26~7.32 (m, 3H), 6.55 (s, 1H), 4.04~4.07 (d, J = 12 Hz, 2H), 3.71 (s, 2H), 3.67 (m, 1H), 3.57 (t, 2H), 3.02 (d, 8H), 2.10 (m, 2H), 1.60 (m, 2H) |

EXAMPLE 162

(Tetrahydropyran-4-yl)-[3-bromo-5-(morpholin-4-yl)methyl-2-phenyl-1H-indol-7-yl]-amine 4-[3-Bromo-2-phenyl-7-nitro-1H-indol-5-yl]-morpholine prepared in Preparation 48 and tetrahydropyran-4-one were reacted according to the same procedure as Example 1 to give the title compound.

¹H-NMR (500 MHz, CDCl₃); δ 8.12 (br, 1H), 7.81 (d, J=7.3 Hz, 2H0, 7.49 (t, J=7.3 Hz, 2H), 7.40 (t, J=7.3 Hz, 1H), 7.02 (s, 1H), 6.64 (s, 1H), 4.04 (m, 2H), 3.73~3.66 (m, 5H), 3.60~3.54 (m, 4H), 2.47 (m, 4H), 2.10 (m, 2H), 1.56 (m, 2H)

EXPERIMENTAL EXAMPLE 1

Measurements and Analysis of the Example Compounds for the Hepatocyte Protective Effect Against the Substances Deriving Hepatocyte Toxicity Various endogenous/exogenous attacks on the cells trigger the mechanisms of cell death which is broadly classified into two types, i.e. apoptosis or necrosis. Using these cell death mechanisms, in the present experimental example, primary hepatocytes isolated from rats were treated with drugs which were clinically shown to result in serious side-effects of hepatocyte toxicity or various chemicals which derive cell death, and the compounds synthesized in the Examples were estimated for their hepatocyte protective effects, after 24-48 h. The substances used to derive hepatocyte death include CCl₄, ActD, H₂O₂, doxorubicin, anti-Fas Ab/Actinomycin D, acetaminophen, EtOH, CdCl₂, palmitate, stearate, cyclophosphamide, terfenadine, diclofenac, simvastatin, and adefovir. Primary hepatocytes were isolated using the method of Seglen PO (Experimental Cell Research 74 (1972) pp 450-454). Briefly, hepatocytes were isolated according to the two-step collagenase perfusion method, and dead cells were removed by low speed (500 rpm) centrifugation for 10 min using percoll gradient (Kreamer B L etc, In Vitro Cellular & Developmental Biology 22 (1986) pp 201-211). During this step, the viability of cells was maintained 90% or above. The cells were suspended in HepatoZYME media (Gibco BRL), and the number of cells was counted. 1.5×10⁴ cells in 100 μl were placed into the collagen-coated 96-well plate (BD biocoat), and adhered on the bottom for 3-4 h.

In order to assess the hepatocyte protective effect, above adhered cells were pretreated with the Example compounds for 30 min. At this time, the concentration of the Example compounds were serially diluted by 2-fold or 3-fold over 5 steps starting from 30 uM, 10 uM or 1 uM depending on the experiments, and the final concentration of DMSO was adjusted to 0.2%. 30 min after the treatment by compounds, cells were treated by the substances deriving hepatocyte death or hepatotoxic drugs at the concentrations indicated in Table 1. After 24-48 h, the viability of cells was determined to estimate the hepatocyte protective effects. The viability of cells was determined using WST-1 (MK-400, Takeda) method by the absorbance at 440 nm. Hepatocyte protective effects of the Example compounds were represented by "$EC_{50}$," which was calculated from measured values. "$EC_{50}$" herein means the concentration of the compound at which 50% of maximum protective effect is observed in the experiment.

Preferably, $EC_{50}$ of the Example compound is 30 uM or less, more preferably, 10 uM or less, and especially preferably, 1.0 uM or less.

Table 1 shows the treatment concentrations of various substances deriving hepatotoxicity and the hepatocyte protective effect of the compound of Example 41. Table 2 shows the cell protective effects of the Example compounds against a substance which results in hepatotoxicity, doxorubicin.

TABLE 1

Protective effect of the compound of Example 41 against the substances deriving hepatotoxicity

| Substances deriving hepatocyte toxicity | Treatment concentration | $EC_{50}$ (μM) | Note on the substances deriving hepatocyte toxicity |
|---|---|---|---|
| Doxorubicin | 5 uM | 0.06 | Anti-cancer drug |
| $CCl_4$ | 10 mM | 0.8 | Xenobiotics/liver damage |
| Actinomycin D | 100 ng/mL | 0.17 | Anti-biotics/liver damage |
| EtOH | 2.5% | 9 | Steatohepatitis |
| $H_2O_2$ | 10 mM | 0.8 | Reactive oxygen species/liver damage |
| Palmitic acid | 700 uM | <0.6 | Fatty liver |
| Stearic acid | 700 uM | <0.6 | Fatty liver |
| Anti-Fas Ab/Actinomycin D | 1 ug/mL 5 ng/mL | <0.6 | Hepatotoxicity |
| $CdCl_2$ | 1 uM | 1.9 | Xenobiotics/liver damage |
| Cyclophosphamide | 3 mM | <0.2 | Anti-leukemic drug |
| Tacrine | 0.5 mM | 50% viability at 3-100 uM | Anti-alzheimer drug |

TABLE 2

Cell protective effects against doxorubicin in hepatocytes

| Example | EC50 (uM) |
|---|---|
| 1 | 0.1 |
| 5 | 0.5 |
| 6 | 0.3 |
| 7 | 0.5 |
| 8 | 2.5 |
| 9 | 0.2 |
| 10 | 0.2 |
| 11 | 0.1 |
| 12 | 0.4 |
| 13 | 0.4 |
| 14 | 0.3 |
| 15 | 0.1 |
| 17 | 0.54 |

TABLE 2-continued

Cell protective effects against doxorubicin in hepatocytes

| Example | EC50 (uM) |
|---|---|
| 19 | 0.07 |
| 20 | 0.3 |
| 21 | 0.04 |
| 24 | 0.9 |
| 27 | 2.4 |
| 28 | 0.17 |
| 29 | 0.07 |
| 30 | 0.14 |
| 31 | 0.16 |
| 32 | 0.13 |
| 33 | 0.15 |
| 34 | >2 |
| 35 | 0.63 |
| 36 | 0.063 |
| 37 | 0.15 |
| 38 | 0.11 |
| 39 | 0.33 |
| 40 | 0.2 |
| 41 | 0.06 |
| 42 | 0.04 |
| 43 | 0.046 |
| 44 | 0.17 |
| 45 | 0.21 |
| 46 | 0.05 |
| 47 | 0.05 |
| 48 | 0.044 |
| 49 | 0.133 |
| 50 | 0.043 |
| 51 | 0.23 |
| 52 | 0.14 |
| 53 | 0.04 |
| 54 | 0.22 |
| 55 | 0.3 |
| 56 | 0.13 |
| 57 | 0.27 |
| 58 | 0.26 |
| 59 | 0.2 |
| 60 | 0.17 |
| 61 | 0.26 |
| 62 | 0.11 |
| 63 | 0.17 |
| 64 | 0.26 |
| 65 | 0.6 |
| 67 | <0.13 |
| 68 | 0.32 |
| 69 | 0.355 |
| 70 | 0.256 |
| 71 | 0.254 |
| 72 | 0.06 |
| 73 | 0.12 |
| 74 | 0.35 |
| 75 | 0.12 |
| 76 | 0.14 |
| 77 | 0.14 |
| 78 | 0.21 |
| 79 | 0.14 |
| 80 | 0.1 |
| 81 | 0.11 |
| 82 | 0.07 |
| 83 | 0.05 |
| 84 | 0.09 |
| 85 | 0.36 |
| 86 | 1.44 |
| 87 | 0.6 |
| 88 | >2 |
| 89 | 0.3 |
| 90 | 0.146 |
| 91 | 0.042 |
| 92 | 0.036 |
| 93 | 0.16 |
| 94 | 0.08 |
| 95 | 0.21 |
| 96 | 0.12 |
| 97 | 0.09 |
| 98 | 0.11 |
| 99 | 0.2 |

TABLE 2-continued

Cell protective effects against doxorubicin in hepatocytes

| Example | EC50 (uM) |
|---|---|
| 100 | 0.08 |
| 101 | 0.08 |
| 102 | 0.3 |
| 103 | 0.106 |
| 104 | 0.08 |
| 105 | 0.07 |
| 106 | 0.45 |
| 107 | 0.35 |
| 109 | 0.257 |
| 111 | 0.257 |
| 112 | 0.45 |
| 113 | 0.35 |
| 114 | 0.37 |
| 115 | >2 |
| 117 | 0.26 |
| 118 | 1.1 |
| 119 | 0.14 |
| 121 | 0.2 |
| 122 | 0.2 |
| 123 | 0.19 |
| 124 | 0.15 |
| 125 | 0.111 |
| 126 | 0.2 |
| 127 | 0.59 |
| 128 | 0.17 |
| 129 | 1.16 |
| 130 | 0.38 |
| 131 | 0.36 |
| 132 | 0.43 |
| 133 | 0.15 |
| 134 | >1 |
| 135 | 0.15 |
| 136 | 0.05 |
| 137 | 0.16 |
| 138 | 0.1 |
| 139 | 0.33 |
| 140 | 0.13 |
| 141 | 0.46 |
| 142 | 0.05 |
| 143 | 0.066 |
| 144 | 0.3 |
| 146 | 0.33 |
| 147 | 0.46 |
| 148 | 0.16 |
| 149 | 0.55 |
| 150 | 0.16 |
| 151 | >2 |
| 152 | 0.24 |
| 153 | 2.1 |
| 154 | 4.2 |
| 155 | 1.3 |
| 156 | >10 |
| 157 | 0.9 |
| 158 | 2.77 |
| 159 | 0.11 |
| 161 | 0.36 |
| 162 | 0.7 |

EXPERIMENTAL EXAMPLE 2

Protective Effects when tBHP (Tert-Butyl Hydroxy Peroxide; t-BuOOH) was Treated on Hepatocytes and Other Cells Derived from Various Tissues 1) Protective Effect when tBHP was Treated on Primary Hepatocytes Hepatocytes were isolated according to the same procedure as Experimental Example 1, suspended in DMEM (Gibco+10% FBS+1× antibiotics) media, and distributed to the plate. After 24 h from the distribution of hepatocytes, the compounds were serially diluted by 3-fold to the final concentration of 30, 10, 3, 1, 0.3, 0.1 uM, by which the cells were pretreated for 30 min. Cells were treated with tBHP at the final concentration of 300 uM, and the protective effects were determined after 1 h. As in Experimental Example 1, after the treatment with WST-1 (Takeda, 10 uL) for 1.5 h, $EC_{50}$ values were calculated by absorbance measurements at 440 nm using SpectraMax (Molecular Device).

Preferably, $EC_{50}$ of the Example compound is 30 uM or less, more preferably, 10 uM or less, and especially preferably, 1.0 uM or less.

2) Protective Effect when tBHP was Treated on Pancreatic Cells (Linm5F)

In order to determine the protective effect on pancreatic cells, Linm5F cells, a sort of the beta cells, were distributed into the 96-well plate in the amount of $2 \times 10^4$ cells/well, and incubated for 24 h. The Example compounds were serially diluted by 3-fold to the final concentration of 30, 10, 3, 1, 0.3, 0.1 uM, by which each well was treated for 1 h. Cells were treated with tBHP at the final concentration of 400 uM, and further incubated for 5 h. Protective effects were determined using SRB (Sulforhodamine B Protein) method in which total amount of cellular protein is stained. Briefly, cells were incubated for 5 h, 50 uL of 4% formaldehyde solution was added to each well to fix the cells, and stored for about 30 min at room temperature. After discarding the media, each well was washed with distilled water 2-3 times, and the plate was dried in an oven at 50° C. 50 uL of SRB solution was added to each well, and placed for about 30 min at room temperature. After removing SRB solution, the plate was washed with 1% acetic acid solution 2-3 times. After drying the plate in an oven at 50° C., 100 uL of 10 mM Tris was added to elute SRB which was staining the intracellular protein. Absorbance was measured at 590 nm and 650 nm using SpectrMax, and the absorbance at 650 nm was subtracted from the absorbance at 590 nm to calculate $EC_{50}$ value.

Preferably, $EC_{50}$ of the Example compound is 30 uM or less, more preferably, 10 uM or less, and especially preferably, 1.0 uM or less. The compounds of Examples 56, 106, and 107 as representative compounds showed excellent activities in the present experiment, and their $EC_{50}$ values were 0.1 uM or less.

3) Protective Effect when tBHP was Treated on Cardiac Cells (H9C2, White Rat Cardiomyocyte)

In order to assess the protective effect on cardiac cells, H9C2 cells were distributed in the amount of $1.5 \times 10^4$ cells/well, and incubated for 24 h. The Example compounds were serially diluted by 3-fold to the final concentration of 30, 10, 3, 1, 0.3, 0.1 uM, by which each well was treated for 45 min. Cells were treated with tBHP at the final concentration of 400 uM, and incubated for 2 h. Protective effect of each compound was determined using the same SRB method as in Linm5F of above mentioned 2).

Preferably, $EC_{50}$ of the Example compound is 30 uM or less, more preferably, 10 uM or less, and especially preferably, 1.0 uM or less. As representative compounds, for example, $EC_{50}$ of the compound of Example 86 was 0.5 uM. Also, the compounds of Examples 39, 74, 86, 97 and 117 showed excellent activities in the present experiment, and their $EC_{50}$ values were 0.2 uM or less.

4) Protective Effect when tBHP was Treated on Kidney Cells (LLC-PK1)

In order to determine the protective effect on kidney cells, $4 \times 10^4$ cells were distributed into each well, and incubated for 24 h. Cells were treated with the Example compounds at the final concentration of 30, 10, 3, 1, 0.3, 0.1 uM, and incubated for 30 min. Cells were treated with 400 uM tBHP, and further incubated for 6 h. Protective effect of each compound was determined using the same SRB method as in Linm5F of above mentioned 2).

Preferably, $EC_{50}$ of the Example compound is 30 uM or less, more preferably, 10 uM or less, and especially preferably, 1.0 uM or less. Representatively, $EC_{50}$ of the compound of Example 56 was 0.66 uM.

5) Protective Effect when tBHP was Treated on Chondrocytes

In order to determine the protective effect on chondrocytes, chondrocytes were isolated from 2 hind legs of 16 week-old SD rats (body weight: 450-460 g). Isolation method is as follows. Cartilage isolated from the knee regions of rat hind legs was transferred to a 100 pi plate containing PBS (+1× antibiotics). PBS was maintained 4° C. in an ice-bath. PBS was exchanged with fresh one, and centrifuged at 1000 rpm. After removal of PBS, 3 mL of 1× trypsin (Gibco) at the temperature of 37° C. was added and followed by the treatment for 15 min. Supernatant was discarded after centrifugation, and washed again with PBS. Supernatant was discarded after centrifugation. After the addition of 0.2% collagenase (Worthington, type II) thereto, the cells were isolated by the overnight incubation in a rotating 37° C. incubator. Filtered cell solution was centrifuged, and the supernatant was discarded. Following the washing with PBS, cells were suspended in 10 mL of DMEM/F-12 (Gibco, 10% FBS). $2\times10^4$ cells were distributed to each well, and incubated for 24 h. The Example compounds were serially diluted by 3-fold to the final concentration of 30, 10, 3, 1, 0.3, 0.1 uM, by which each well was treated for 1 h. Cells were treated with tBHP at the final concentration of 500 uM, and incubated for 3 h. Protective effect of each compound was determined using the same SRB staining method as in Linm5F of above mentioned 2).

Preferably, $EC_{50}$ of the Example compound is 30 uM or less, more preferably, 10 uM or less, and especially preferably, 1.0 uM or less. Representatively, the compounds of Examples 56 and 63 showed excellent activities in the present experiment, and their $EC_{50}$ values were 0.1 uM or less.

6) Protective Effect when tBHP was Treated on Brain Cells (SK-N-MC)

In order to assess the protective effect on brain cells, $2\times10^4$ brain cells were distributed into the 96-well plate using DMEM media (Gibco, 10% FBS), and incubated for 24 h. The Example compounds were serially diluted by 3-fold to the final concentration of 30, 10, 3, 1, 0.3, 0.1 uM, by which each well was treated for 1 h. Cells were treated with tBHP at the final concentration of 400 uM, and incubated for 6 h. 50 uL of media was taken from each well to proceed with LDH assay (Promega). In LDH assay, 50 uL of media was mixed with 50 uL of assay solution. After the reaction for 30 min at room temperature, absorbance was measured at 490 nm using SpectraMax (Molecular Device).

Preferably, $EC_{50}$, of the Example compound is 30 uM or less, more preferably, 10 uM or less, and especially preferably, 1.0 uM or less. Representatively, $EC_{50}$, value of the compound of Example 115 was 0.26 uM. Also, the compounds of Examples 37, 55 and 63 showed excellent activities in the present experiment, and their $EC_{50}$ values were 0.1 uM or less.

[Industrial Applicability]

As is demonstrated in above results, the novel compounds according to the present invention not only exhibit the effects for hepatoprotection and hepatic functional improvement, but also can be useful for the prevention and treatment of chronic hepatic diseases such as fatty liver, hepatic fibrosis, hepatocirrhosis, etc. and acute/chronic hepatic diseases such as hepatitis, etc. caused by virus or drugs. The compounds of the present invention also exhibit the necrosis inhibitory efficacy in the cells from pancreas, kidney, brain, cartilage, and heart.

Thus, the compounds of the present invention can be useful in the prevention and treatment of necrosis and associated diseases.

It will be within the ability of those skilled in the art, to conduct various applications and modifications without departing from the scope of the present invention.

The invention claimed is:

1. A method of inhibiting necrosis in tissue selected from the group consisting of liver, pancreas and cartilage, comprising: administering an effective amount of a compound of formula (1) or pharmaceutically acceptable salt or enantiomer or diastereomer thereof to a subject in need thereof, wherein the compound is an indole compound of the following formula (1):

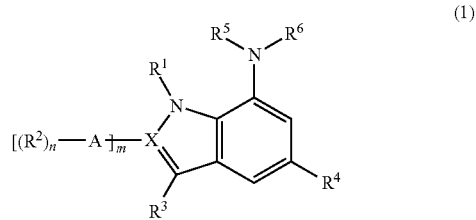

in which n denotes a number of 1 to 3, m denotes 0 or 1,

A represents phenyl,

X represents C or CH, with the proviso that m is 1 when X is C, $R^1$ represent hydrogen, alkyl, —$(CH_2)_r NR^7 R^8$, or —$(CH_2)_r CO_2 H$, wherein r denotes a number of 1 to 5, and $R^7$ and $R^8$ independently of one another represent hydrogen, alkyl or alkylcarbonyl, or may together form an optionally alkyl-substituted alkylene chain wherein optionally one methylene is replaced by N atom, $R^2$ represents hydrogen, halogen, cyano, nitro, hydroxy, alkyl, alkoxy or trialkylsilyl, represents —$(CH_2)_p CO_2 R^7$, —$(CH_2)_p OR^7$, —$(CH_2)_p NR^7 R^8$, —$NHR^{10}$, —$N(H)S(O)_2 R^7$, —$NHC(O)R^{10}$, —$(CH_2)_p S(O)_2 R^7$ or $(CH_2)_p$-heterocycle-$R^{10}$, wherein p denotes a number of 0 to 3, $R^7$ and $R^8$ are as defined above, $R^{10}$ represents hydrogen, oxo, alkylsulfonyl, alkylcarbonyl, alkyloxycarbonyl, alkylaminocarbonyl, alkoxy, alkyl or heterocycle, $R^3$ represents hydrogen, cyano, halogen, alkyl or phenyl, or represents —$(CH_2)_n$-heterocycle or —$(CH_2)_n$-aryl, wherein n denotes a number of 0 to 3, $R^4$ represents —$YR^{11}$, wherein Y represents a direct bond or —$(CR^7 R^8)_p Y'$—, wherein p denotes a number of 0 to 3, $R^7$ and $R^8$ are as defined above, Y' is selected from the group consisting of —O—, —S—, —$NR^{12}$—, —$NR^{12}C(O)$—, —C(O)—, —C(O)O—, —C(O)$NR^{12}$—, —$S(O)_q$—, and —$S(O)_q NR^{12}$—, wherein $R^{12}$ represents hydrogen, alkyl, aryl or heteroaryl, q denotes a number of 0 to 2, $R^{11}$ is selected from the group consisting of hydrogen, cyano, halogen, hydroxy, thiol, carboxy, alkyl and —$(CH_2)_t B$—$R^{13}$, wherein t denotes a number of 0 to 3, B represents heterocycle, heteroaryl or aryl, $R^{13}$ represents hydrogen, cyano, halogen, hydroxy, oxo, thiol, carboxy, carboxyalkyl, alkylcarbonyloxy, alkyl, alkoxy, alkylthio, alkylcarbonyl or alkylsulfonyl, $R^5$ represents hydrogen, alkyl, cycloalkyl, heterocycle or heterocyclylalkyl, $R^6$ represents —$(CR^7R^8)_p$—Z-D-W—$R^{14}$, wherein Z represents a direct bond, or is selected from the group consisting of —C(O)—, —C(O)O—, —C(O)$NR^{12}$—, and —$S(O)_y$—, y denotes a number of 1 or 2, D represents a direct bond, or represents cycloalkyl, heteroaryl or heterocycle, W represents a direct bond, or represents —$NR^7$—, —C(O)—, —C(O)O—, —C(O)$NR^{12}$—, —$S(O)_y$—, —$S(O)_y NR^{12}$— or —$NR^{12}S(O)_y$—, wherein $R^{14}$ represents hydrogen, hydroxy, alkyl, alkoxy, heterocycle, heteroaryl, aryl or aralkyl, $R^5$ and $R^6$ together represent alkylene chain, where alkyl, alkoxy, aryl, cycloalkyl, heterocycle and heteroaryl may be optionally substituted, and the substituents are one or more selected from the group consisting of hydroxy, halogen, nitrile, amino, alkylamino, dialkylamino, carboxy, alkyl, alkoxy, carboxyalkyl, alkylcarbonyloxy, alkylthio, alkyloxycarbonyl, alkylaminocarbonyl, arylalkoxy and oxo, provided that $R^3$ is phenyl when X is CH, and provided that $R^6$ is not hydrogen when X is C, and pharmaceutically acceptable salts or enantiomers or diasteromers thereof.

2. The method of claim 1, wherein the tissue is liver tissue.

3. A method of inhibiting necrosis in a cell, comprising: contacting a compound with the cell, wherein the compound is an indole compound having the following formula (1):

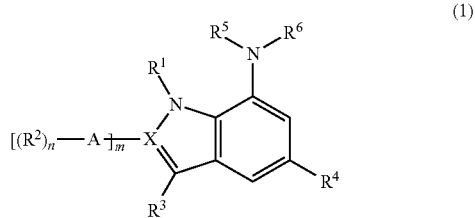

(1)

in which n denotes a number of 1 to 3, m denotes 0 or 1,

A represents phenyl,

X represents C or CH, with the proviso that m is 1 when X is C, $R^1$ represent hydrogen, alkyl, —$(CH_2)_r NR^7R^8$, or —$(CH_2)_r CO_2H$, wherein r denotes a number of 1 to 5, and $R^7$ and $R^8$ independently of one another represent hydrogen, alkyl or alkylcarbonyl, or may together form an optionally alkyl-substituted alkylene chain wherein optionally one methylene is replaced by N atom, $R^2$ represents hydrogen, halogen, cyano, nitro, hydroxy, alkyl, alkoxy or trialkylsilyl, represents —$(CH_2)_p CO_2R^7$, —$(CH_2)_p OR^7$, —$(CH_2)_p NR^7R^8$, —$NHR^{10}$, —$N(H)S(O)_2R^7$, —$NHC(O)R^{10}$, —$(CH_2)_p S(O)_2R^7$ or $(CH_2)_p$-heterocycle-$R^{10}$, wherein p denotes a number of 0 to 3, $R^7$ and $R^8$ are as defined above, $R^{10}$ represents hydrogen, oxo, alkylsulfonyl, alkylcarbonyl, alkyloxycarbonyl, alkylaminocarbonyl, alkoxy, alkyl or heterocycle, $R^3$ represents hydrogen, cyano, halogen, alkyl or phenyl, or represents —$(CH_2)_n$-heterocycle or —$(CH_2)_n$-aryl, wherein n denotes a number of 0 to 3, $R^4$ represents —$YR^{11}$, wherein Y represents a direct bond or —$(CR^7R^8)_p Y'$—, wherein p denotes a number of 0 to 3, $R^7$ and $R^8$ are as defined above, Y' is selected from the group consisting of —O—, —S—, —$NR^{12}$C(O)—, —C(O)—, —C(O)O—, —C(O)$NR^{12}$—, —$S(O)_q$—, and —$S(O)_q NR^{12}$—, wherein $R^{12}$ represents hydrogen, alkyl, aryl or heteroaryl, q denotes a number of 0 to 2, $R^{11}$ is selected from the group consisting of hydrogen, cyano, halogen, hydroxy, thiol, carboxy, alkyl and —$(CH_2)_t B$—$R^{13}$, wherein t denotes a number of 0 to 3, B represents heterocycle, heteroaryl or aryl, $R^{13}$ represents hydrogen, cyano, halogen, hydroxy, oxo, thiol, carboxy, carboxyalkyl, alkylcarbonyloxy, alkyl, alkoxy, alkylthio, alkylcarbonyl or alkylsulfonyl, $R^5$ represents hydrogen, alkyl, cycloalkyl, heterocycle or heterocyclylalkyl, $R^6$ represents —$(CR^7R^8)_p$—Z-D-W—$R^{14}$, wherein Z represents a direct bond, or is selected from the group consisting of —C(O)—, —C(O)O—, —C(O)$NR^{12}$—, and —$S(O)_y$—, y denotes a number of 1 or 2, D represents a direct bond, or represents cycloalkyl, heteroaryl or heterocycle, W represents a direct bond, or represents —$NR^7$—, —C(O)—, —C(O)O—, —C(O)$NR^{12}$—, $S(O)_y$—, —$S(O)_y NR^{12}$— or —$NR^{12}S(O)_y$—, wherein $R^{14}$ represents hydrogen, hydroxy, alkyl, alkoxy, heterocycle, heteroaryl, aryl or aralkyl, $R^5$ and $R^6$ together represent alkylene chain, where alkyl, alkoxy, aryl, cycloalkyl, heterocycle and heteroaryl may be optionally substituted, and the substituents are one or more selected from the group consisting of hydroxy, halogen, nitrile, amino, alkylamino, dialkylamino, carboxy, alkyl, alkoxy, carboxyalkyl, alkylcarbonyloxy, alkylthio, alkyloxycarbonyl, alkylaminocarbonyl, arylalkoxy and oxo, provided that $R^3$ is phenyl when X is CH, and provided that $R^6$ is not hydrogen when X is C.

* * * * *